United States Patent
Hori et al.

(10) Patent No.: US 11,299,465 B2
(45) Date of Patent: Apr. 12, 2022

(54) CARBOXYLIC ACID COMPOUNDS

(71) Applicant: Sumitomo Dainippon Pharma Co., Ltd., Osaka (JP)

(72) Inventors: Seiji Hori, Osaka (JP); Futoshi Hasegawa, Osaka (JP); Daisuke Urabe, Osaka (JP); Hirotaka Kurebayashi, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/736,660

(22) Filed: Jan. 7, 2020

(65) Prior Publication Data
US 2020/0317623 A1 Oct. 8, 2020

Related U.S. Application Data

(63) Continuation of application No. 16/167,974, filed on Oct. 23, 2018, now Pat. No. 10,562,861, which is a continuation of application No. 15/152,497, filed on May 11, 2016, now Pat. No. 10,150,743, which is a continuation of application No. 14/401,366, filed as application No. PCT/JP2013/064420 on May 17, 2013, now Pat. No. 9,376,398.

(60) Provisional application No. 61/806,158, filed on Mar. 28, 2013, provisional application No. 61/648,816, filed on May 18, 2012.

(51) Int. Cl.
| C07D 239/48 | (2006.01) |
| C07D 403/12 | (2006.01) |
| C07D 403/10 | (2006.01) |
| C07D 239/47 | (2006.01) |
| C07D 239/49 | (2006.01) |
| A61K 31/505 | (2006.01) |
| A61K 31/506 | (2006.01) |

(52) U.S. Cl.
CPC ......... *C07D 239/48* (2013.01); *C07D 239/47* (2013.01); *C07D 239/49* (2013.01); *C07D 403/10* (2013.01); *C07D 403/12* (2013.01); *A61K 31/505* (2013.01); *A61K 31/506* (2013.01); *Y02P 20/55* (2015.11)

(58) Field of Classification Search
CPC .................................................. C07D 239/48
See application file for complete search history.

(56) References Cited

U.S. PATENT DOCUMENTS

| 4,179,562 A | 12/1979 | Ponsford |
| 4,689,338 A | 8/1987 | Gerster |
| 4,698,348 A | 10/1987 | Gerster |
| 4,714,701 A | 12/1987 | Beauchamp |
| 4,912,112 A | 3/1990 | Seydel et al. |
| 5,736,549 A | 4/1998 | Beasley et al. |
| 5,994,361 A | 11/1999 | Penney et al. |
| 6,028,076 A | 2/2000 | Hirota et al. |
| 6,110,923 A | 8/2000 | Ely |
| 6,329,381 B1 | 12/2001 | Kurimoto et al. |
| 6,376,501 B1 | 4/2002 | Isobe et al. |
| 6,458,798 B1 | 10/2002 | Fujita et al. |
| 6,593,326 B1 | 7/2003 | Bradbury et al. |
| 6,951,866 B2 | 10/2005 | Fujita et al. |
| 7,157,465 B2 | 1/2007 | Isobe et al. |
| 8,148,371 B2 | 4/2012 | Isobe et al. |
| 9,376,398 B2 | 6/2016 | Hori et al. |
| 10,150,743 B2 | 12/2018 | Hori et al. |
| 2002/0128264 A1 | 9/2002 | Taylor |

(Continued)

FOREIGN PATENT DOCUMENTS

| CN | 1335838 A | 2/2002 |
| CN | 101300235 A | 11/2008 |

(Continued)

OTHER PUBLICATIONS

McMahon et al. (2000).*
Pinedo et al. (2000).*
Cancer Drug Design and Discovery, Neidle, Stephen, ed. (Elsevier/Academic Press, 2008) p. 427.*
Aoki, M., et al., "Weekly Dosing of AZD8848/DSP-3025, A Novel TLR7 Agonist Antedrug, Demonstrates A Prolonged Period of Control Against Markers of Pulmonary Inflammation in An Alergen Challenge Model In The Mouse," ATS New Orleans May 2010.
Balchen, T., et al., "Pharmacokinetics, Safety and Tolerability of Single Ascending Intranasal Doses of AZD8848 in BChE-Deficient Volunteers," American Thoracic Society, San Francisco, May 18-23, 2012.

(Continued)

Primary Examiner — Paul V Ward
(74) Attorney, Agent, or Firm — Finnegan, Henderson, Farabow, Garrett & Dunner, LLP

(57) ABSTRACT

The present disclosure concerns at least one entity chosen from compounds of Formula (I) and pharmaceutically acceptable salts thereof:

(I)

wherein the variable groups X, $R^1$, $R^2$, $R^3$ m, n and p are as defined herein. The present disclosure also relates to methods for the preparation of at least one such entity, and intermediates useful in the preparation thereof, to pharmaceutical compositions containing at least one such entity, to the use of at least one such entity in the preparation of medicaments, and to the use of at least one such entity in the treatment of conditions such as, for example, allergic diseases, autoimmune diseases, viral diseases, and cancer.

18 Claims, 8 Drawing Sheets

(56) References Cited

U.S. PATENT DOCUMENTS

| | | |
|---|---|---|
| 2003/0191086 A1 | 10/2003 | Hanus et al. |
| 2004/0132748 A1 | 7/2004 | Isobe et al. |
| 2004/0214192 A1 | 10/2004 | Hashida et al. |
| 2005/0054590 A1 | 3/2005 | Averett |
| 2005/0119273 A1 | 6/2005 | Lipford et al. |
| 2006/0052403 A1 | 3/2006 | Isobe et al. |
| 2007/0190071 A1 | 8/2007 | Kurimoto et al. |
| 2007/0225303 A1 | 9/2007 | Ogita et al. |
| 2008/0269240 A1 | 10/2008 | Hashimoto et al. |
| 2008/0300244 A1 | 12/2008 | Bonnert et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0143400 A1 | 6/2009 | McInally et al. |
| 2009/0192153 A1 | 7/2009 | Hashimoto et al. |
| 2009/0209524 A1 | 8/2009 | Bennett et al. |
| 2009/0264447 A1 | 10/2009 | Dietz et al. |
| 2010/0087443 A1 | 4/2010 | Bonner et al. |
| 2010/0093998 A1 | 4/2010 | Isobe et al. |
| 2010/0099870 A1 | 4/2010 | Isobe et al. |
| 2010/0130491 A1 | 5/2010 | Bonnert et al. |
| 2010/0240623 A1 | 9/2010 | Cook et al. |
| 2010/0280001 A1 | 11/2010 | Bonnert et al. |
| 2010/0298364 A1 | 11/2010 | Bennett et al. |
| 2011/0028715 A1 | 2/2011 | Isobe et al. |
| 2011/0046369 A1 | 2/2011 | Hashimoto et al. |
| 2011/0054168 A1 | 3/2011 | Kurimoto et al. |
| 2011/0136801 A1 | 6/2011 | Isobe et al. |
| 2011/0294802 A1 | 12/2011 | Mcinally et al. |
| 2011/0298402 A1 | 12/2011 | Iwashita et al. |
| 2011/0306610 A1 | 12/2011 | Kurimoto et al. |
| 2012/0122867 A1 | 5/2012 | Bennet et al. |
| 2012/0189646 A1 | 7/2012 | Mcinally et al. |
| 2013/0045955 A1 | 2/2013 | Bennett et al. |
| 2013/0225555 A1 | 8/2013 | Bonnert et al. |
| 2013/0267532 A1 | 10/2013 | Tosaki et al. |
| 2013/0338174 A1 | 12/2013 | Abbott et al. |
| 2015/0080396 A1 | 3/2015 | Bennett et al. |
| 2015/0099770 A1 | 4/2015 | Hori et al. |

FOREIGN PATENT DOCUMENTS

| | | |
|---|---|---|
| EP | 1 110 951 | 6/2001 |
| EP | 1 550 662 | 7/2005 |
| EP | 1 728 793 | 12/2006 |
| GB | 1375162 | 11/1974 |
| JP | 08-165292 | 6/1996 |
| JP | 11-193282 | 7/1999 |
| JP | 2011-504497 | 2/2011 |
| RU | 2 343 148 C2 | 8/2005 |
| WO | WO 98/01448 A1 | 1/1998 |
| WO | WO 99/032122 A1 | 7/1999 |
| WO | WO 99/028321 A1 | 10/1999 |
| WO | WO 99/050249 A2 | 10/1999 |
| WO | WO 00/012487 A1 | 3/2000 |
| WO | WO 00/039101 A1 | 7/2000 |
| WO | WO 01/007027 A2 | 2/2001 |
| WO | WO 02/004449 A2 | 1/2002 |
| WO | WO 02/085905 A1 | 10/2002 |
| WO | WO 2004/029054 A1 | 4/2004 |
| WO | WO 2005/009978 A1 | 2/2005 |
| WO | WO 2005/092892 A1 | 10/2005 |
| WO | WO 2005/092893 A1 | 10/2005 |
| WO | WO 2006/137706 A1 | 12/2006 |
| WO | WO 2007/025901 A1 | 3/2007 |
| WO | WO 2007/031726 A1 | 3/2007 |
| WO | WO 2007/031829 A2 | 3/2007 |
| WO | WO 2007/034173 A1 | 3/2007 |
| WO | WO 2007/034817 A1 | 3/2007 |
| WO | WO 2007/034881 A1 | 3/2007 |
| WO | WO 2007/034882 A1 | 3/2007 |
| WO | WO 2007/034916 A1 | 3/2007 |
| WO | WO 2007/034917 A1 | 3/2007 |
| WO | WO 2008/001070 A1 | 1/2008 |
| WO | WO 2008/004948 A1 | 1/2008 |
| WO | WO 2008/015250 A1 | 2/2008 |
| WO | WO 2008/071976 A1 | 6/2008 |
| WO | WO 2008/083465 A1 | 7/2008 |
| WO | WO 2008/114006 A1 | 9/2008 |
| WO | WO 2008/114008 A1 | 9/2008 |
| WO | WO 2008/114817 A1 | 9/2008 |
| WO | WO 2008/114819 A1 | 9/2008 |
| WO | WO 2008/135791 A1 | 11/2008 |
| WO | WO 2009/067081 A1 | 5/2009 |
| WO | WO 2010/133882 A1 | 11/2010 |
| WO | WO 2010/133885 A1 | 11/2010 |
| WO | WO 2011/068233 A1 | 6/2011 |
| WO | WO 2012/066335 A1 | 5/2012 |
| WO | WO 2012/066336 A1 | 5/2012 |
| WO | WO 2012/067269 A1 | 5/2012 |
| WO | WO 2019/124500 A1 | 6/2019 |

OTHER PUBLICATIONS

Bell, JP., et al., "AZD8848/DSP-3025, A Novel Potent TLR7 Agonist Antedrug, Demonstrates Negligible Systemic Activity And A Prolonged Period of Control After Cessation of Weekly Dosing in A Brown Norway Rat Ovalbumin Challenge Model," ATS New Orleans, May 2010.

Biffen, M., et al., "Biological Activity of A Novel TLR7 Agonist Antedrug For The Treatment of Allergic Diseases," ATS New Orleans May 2010.

Biffen, M., et al., "Biological Characterization of a Novel Class of Toll-Like Receptor 7 Agonists Designed to Have Reduced Systemic Activity," British Journal of Pharmacology, 166 (2012) pp. 573-586.

Biffen, M., et al., "Novel TLR7 Agonists for the Treatment of Allergic Diseases,"m Toll 2011, Riva del Garda, Italy, May 4-7, 2011.

Brunton, Laurence et al., "Chemotherapy of Neoplastic Diseases," Goodman and Gilman's: The Pharmacological Basis of Therapeutics, $11^{th}$ Edition, 2008, pp. 853-908.

Eiho, K., et al., "Mechanism of Long-Lasting Suppression Against TH2 Immune Response in the Lung by a Novel Antedrug TLR7 Agonist," European Respiratory Society, Amsterdam, Sep. 24-28, 2011.

English language abstract for Russian Patent No. RU 2 343 148 C2, Aug. 27, 2005.

English translation of Japanese Patent Application No. 34722-1997.

English translation of Japanese Patent Application No. 367451-1997.

Falco, E.A., et al., "2,4-Diaminopyrimidines as Antimalarials. I. 5-Aroyloxyl and 5-Alkoxyl Derivatives," Journal of the American Chemical Society, vol. 73, No. 8 (1951) pp. 3753-3758.

Gorden, K.B., et al., Syntheic TLR Agonists Reveal Functional Differences Between Human TLR7 and TLR8, The Journal of Immunology 174 (2005) pp. 1259-1268.

Greiff, et al., "Efficacy and Tolerability of the Toll-like Receptor 7 (TLR7) Agonist AZD8848 in Patients with Seasonal Allergic Rhinitis," American Thoracic Society, San Francisco, May 18-23, 2012.

Greiff, et al., "Repeated Intranasal TLR7 Stimulation Reduces Allergen Responsiveness in Allergic Rhinitis," Respir Res., Jun. 22, 2012, 13(1):53 (27 pages).

Greiff, L., et al., "Repeated Intranasal TLR7 Stimulation Reduces Allergen Responsiveness in Allergic Rhinitis," European Respiratory Society, Amsterdam, Sep. 24-28, 2011.

Hirota, K. et al., "Discovery of 8-Hydroxyadenines as a Novel Type of Interferon Inducer," J. Med. Chem, (2002) pp. 5419-5422.

Huber, J.P., et al., "Cutting Edge: Type I IFN Reverses Human Th2 Commitment and Stability by Suppressing GATA3," The Journal of Immunology 185, (2010) pp. 813-817.

Ikeda, K., et al., "AZD8848/DSP-3025, A Novel Potent TLR7 Agonist Antedrug, Demonstrates Efficacy Against Airway Obstruction and Other Inflammatory Endpoints in Guinea Pig Models of Rhinitis and Asthma with Acute and Weekly Dosing," ATS New Orleans May 2010.

International Preliminary Report on Patentability and Written Opinion of the International Searching Authority for PCT-JP2013/064420, issued from the International Bureau of WIPO dated Nov. 18, 2014.

(56) References Cited

OTHER PUBLICATIONS

International search report for PCT/JP2013/064420, issued from the Japan Patent Office dated Jun. 12, 2013.
Isobe, Y., et al., "Synthesis and Biological Evaluation of Novel 9-Substituted-8-Hydroxyadenine Derivatives as Potent Interferon Inducers," J. Med. Chem. 49 (2006) pp. 2088-2095.
Isobe, Y., et al., "Synthesis and Structure-Activity Relationships of 2-Substituted-8-hydroxyadenine Derivatives as Orally Available Interferon Inducers without Emetic Side Effects," Bioorganic & Medicinal Chemistry 11 (2001) pp. 3641-3647.
Krueger, R.F., et al., "Tilorone Hydrochloride: An Orally Active Antiviral Agent," Science, vol. 169, Sep. 1970, pp. 1213-1215.
Kuhn, W., et al., "Impact of Dose and Dosing Frequency of Intranasal AZD8848 (a TLR7 agonist) on Biomarker Response in Healthy Volunteers," American Thoracic Society, San Francisco, May 18-23, 2012.
Kurimoto, A. et al., "Synthesis and Evaluation of 2-substituted 8-hydroxyadenines as Potent Interferon Inducers with Improved Oral Bioavailabilities," Bioorganic & Medicinal Chemistry 12 (2004) pp. 1091-1099.
Kurimoto, A. et al., "Synthesis and Structure—Activity Relationships of 2-Amino-8-hydroxyadenines as Orally Active Interferon Inducing Agents," Bioorganic & Medicinal Chemistry 11 (2003) pp. 5501-5508.
Kurimoto, A., et al., "Synthesis and Biological Evaluation of 8-Oxoadenine Derivatives as Toll-like Receptor 7 Agonists Introducing the Antedrug Concept," J. Med. Chem. vol. 53., No. 7 (2010) pp. 2964-2972.
Kurimoto, A. et al., "Prodrugs of 9-Benzyl-8-hydroxy-2-(2-hydroxyethylthio)adenine: Potent Interferon Inducing Agents in Monkeys," Chem. Pharm. Bull. vol. 52, No. 4 (2004) pp. 466-469.
Leaker, B., et al. "The Effects of the Novel Toll-like Receptor 7 (TLR7) Agonist AZD8848 on Allergen-Induced Responses in Patients with Mild Asthma," American Thoracic Society, San Francisco, May 18-23, 2012.
Leaker, B., et al., "Effects of the Novel Toll-Like Receptor 7 (TLR7) Agonist AZD8848 on Allergen-Induced Responses in Patients with Mild Asthma," European Respiratory Society, Vienna, Sep. 1-5, 2012.
Lee, J., et al., Molecular Basis for the Immunostimulatory Activity of Guanine Nucleoside Analogs: Activation of Toll-like Receptor 7, Proceedings of the National Academy of Sciences USA, vol. 11, No. 100, May 27, 2003, pp. 6646-6651.
Lee, J., et al., "Activation of Anti-Hepatitis C Virus Responses via Toll-like Receptor 7," Proceedings of the National Academy of Sciences USA, vol. 103, No. 6, Feb. 7, 2006, pp. 1828-1833.
Matsui, H., et al., "Mechanism of Action of Inhibition of Allergic Immune Responses by a Novel Antedrug TLR7 Agonist," The Journal of Immunology, vol. 189, No. 11, Nov. 2, 2012, pp. 5194-5205.
Matsui, H., et al., "Mechanisms of Inhibition of Type-2 Cytokines by Novel TLR7 Agonist Antedrugs," ATS New Orleans May 2010.
McInally, T. "Identification and Pharmacology of Novel TLR7 Agonist Antedrugs," RSC BMSC Inflammation Meeting, Nov. 18, 2010.
McInally, T., et al., "Identification of A Novel TLR7 Agonist Antedrug," EFMC-ISMC 201, Brussels, Belgium, Sep. 5-9, 2010.
Nichol, F.R., "Stimulation of Murine Interferon by a Substituted Pyrimidine," Antimicrobial Agents and Chemotherapy, Mar. 1967, pp. 433-439.
Reiter, M.J., et al., "Cytokine Induction in Mice by the Immunomodulator Imiquimod," Journal of Leukocyte Biology, vol. 55, Feb. 1994, pp. 234-240.
Stringfellow, D.A., "Antiviral and Interferon-Inducing Properties of 1,5-Diamino Anthraquinones," Antimicrobial Agents and Chemotherapy, Jan. 1979, pp. 111-118.
Supplementary European Search Report issued in the European Patent Application No. 13791057.6 dated Oct. 6, 2015.
Tojo, S., et al., "Synthesis and Biological Evaluation of A Novel TLR7 Agonist with an Antedrug Strategy," EFMC-ISMC 201, Brussels, Belgium, Sep. 5-9, 2010.
Yoshimoto, M., et al., "Correlation Analysis of Baker's Studies on Enzyme Inhibition. 2. Chymotrypsin, Trypsin, Thymidine Phosphorylase, uridine Phosphorylase, Thymidylate Synthetase, Cytosine Nucleoside Deaminase, Dihydrofolate Reductase, Malate Dehydrogenase, Glutamate Dehydrogenase, Lactate Dehydrogenase, and Glyceraldehyde-phosphate Dehydrogenase," Journal of Medicinal Chemistry, vol. 19, No. 1 (1976) pp. 71-98.

\* cited by examiner

CARBOXYLIC ACID COMPOUNDS

CROSS-REFERENCE TO RELATED APPLICATIONS

This application is a Continuation of application Ser. No. 16/167,974, filed on Oct. 23, 2018, which is a Continuation of application Ser. No. 15/152,497 filed on May 11, 2016, which is a Continuation of application Ser. No. 14/401,366, filed Nov. 14, 2014, now U.S. Pat. No. 9,376,398, which is a national phase application under 35 U.S.C. § 371 of International Application No. PCT/JP2013/064420, filed May 17, 2013, which claims the benefit of U.S. provisional application No. 61/648,816, filed May 18, 2012, and U.S. provisional application No. 61/806,158, filed Mar. 28, 2013, all of which are incorporated herein by reference.

JOINT RESEARCH AGREEMENT

The subject matter claimed in this application was made as a result of activities undertaken within the scope of a joint research agreement that was in effect before the effective filing date of the claimed invention between AstraZeneca AB and Dainippon Sumitomo Pharma Co., Ltd., named Sumitomo Dainippon Pharma Co., Ltd. on Jun. 19, 2014.

TECHNICAL FIELD

The present disclosure relates to novel carboxylic acid compounds and, more particularly, to certain carboxylic acid compounds that may act as TLR7 agonists and at the same time may exhibit advantageous selectivity over TLR8 and hERG. This disclosure also relates to methods for the preparation of such compounds and intermediates useful in the preparation thereof, to pharmaceutical compositions containing such compounds, to the use of such compounds in the preparation of medicaments, and to the use of such compounds in the treatment of conditions mediated by TLR7, such as allergic diseases, autoimmune diseases, viral diseases and, in particular, cancer.

BACKGROUND ART

Toll-like receptors (TLRs) are expressed on a variety of immune cells, including macrophages and dendritic cells (DCs). TLRs recognise molecular motifs on pathogens called pathogen-associated molecular patterns (PAMPs). To date, 13 TLRs have been identified in man, these include TLRs 1, 2, 4, 5 and 6, which are confined to the cell surface, and TLRs 3, 7, 8 and 9, which are expressed in endosomes. Different TLRs recognise different pathogen-derived ligands, for example: TLR2 (bacterial lipoproteins), TLR3 (double-stranded RNA/poly (I:C)), TLR4 (lipopolysaccharides), TLR5 (flagellin), TLR7 (single-stranded RNA), and TLR9 (CpG-containing DNA). Ligation of TLRs on antigen-presenting cells, such as DCs, leads to production of proinflammatory cytokines, DC maturation, and priming of the adaptive immune system. TLR7 and TLR9 are expressed by plasmacytoid dendritic cells (pDCs) and ligand recognition leads to the secretion of interferon-α (INF-α). Preclinical studies investigating the effects of activation of TLRs, using bacterial or viral components, dosed as monotherapy and/or combined with anti-tumor agents, have shown tumour growth inhibition in a variety of murine tumour models.

Several small molecule TLR7 agonists have been described, including the imidazoquinoline, imiquimod, which has been used to treat a number of dermatological conditions, e.g., genital warts, molluscum contagiosum, and melanoma. In the case of melanoma, topically applied imiquimod (ALDARA™, Graceway Pharmaceuticals, Bristol, Tenn.) demonstrated therapeutic responses in cutaneous metastatic melanoma and lentigo maligna and has been approved for the treatment of superficial basal cell carcinoma (BCC). Preclinical and clinical studies indicate that imiquimod is likely to function through the induction of type 1 IFN and IFN-inducible genes, which in turn can have direct effects on tumour cell growth and/or harness components of the adaptive immune system. 852A is another imidazoquinoline, which, unlike imiquimod, is suitable for systemic administration. Currently, 852A is in phase II clinical trials in a number of cancer indications, including melanoma.

SUMMARY OF INVENTION

Technical Problem

Nevertheless, there remains a need for developing further TLR7 agonists which are expected to be more effective in the treatment of disease, for example cancer, by reason of their superior potency and/or advantageous physical properties (for example, higher solubility, and/or lower plasma protein binding) and/or favourable toxicity profiles and/or favourable metabolic profiles in comparison with other known TLR7 agonists, for example 852A.

Solution to Problem

As demonstrated herein, the carboxylic acid compounds of the present disclosure may be capable of activating TLR7 in vitro. As a consequence of this activity, the compounds of the present disclosure may have value in the prevention and/or treatment of human disease, such as, for example cancer, either as a monotherapy or in combination with other chemotherapeutic agents or radiotherapy regimens.

Advantageous Effects of Invention

In addition, compounds of the present disclosure may have surprisingly advantageous selectivity for TLR7 over TLR8. TLR7 and TLR8 differ in their cellular expression and as a result stimulation with selective agonists induces different cytokine profiles. TLR8 stimulation (either as a TLR8 selective agonist or a TLR7/8 dual agonist) results in enhanced levels of pro-inflammatory cytokines including TNFα, IL-1B and IL-6 (Gorden et al (2005) J. Immunol. 174, 1259-1268). Conversely, TLR8 stimulation may result in lower levels of IFNα. Therefore, a TLR7 selective agonist may favor induction of IFNα, which is important in suppression of Th2 cytokines (Huber et al (2010) J. Immunol. 185; 813-817) that are elevated in allergic disease. In addition, by making compounds selective for TLR7 compared to TLR8 the induction of proinflammatory cytokines may be reduced thus avoiding inflammatory responses in man.

Furthermore, compounds of the present disclosure may have a surprisingly advantageous hERG profile. Compounds that have significant activity against the hERG ion channel are disfavored because such activity is implicated in the development of Torsades de Pointes and cardiac death.

DESCRIPTION OF EMBODIMENTS

Figure 1:
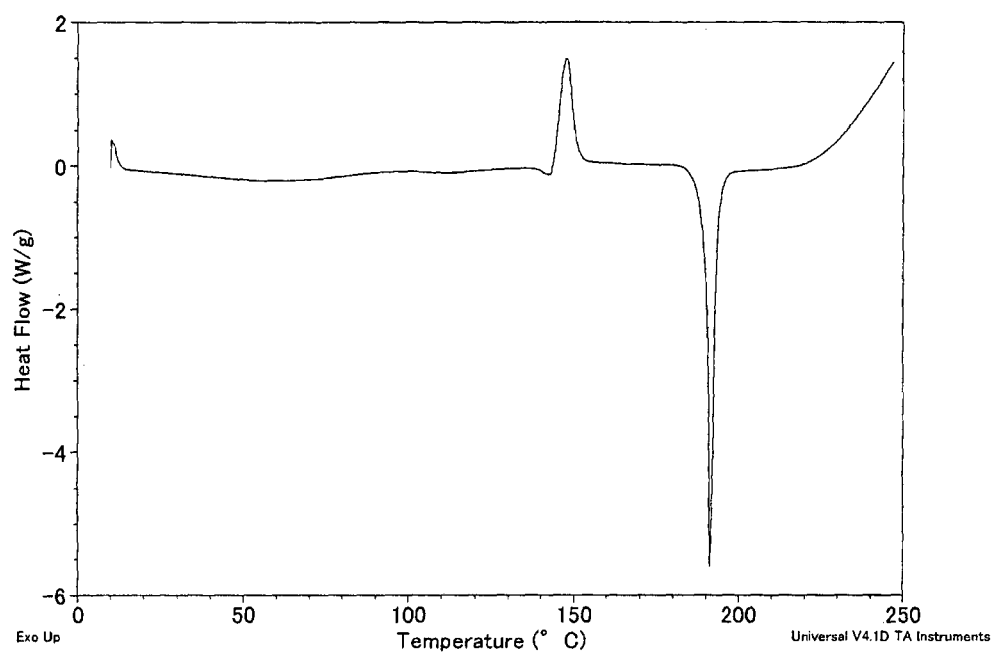
FIG. 1 is a differential scanning calorimetry (DSC) trace for Compound of Example 18 (Form B). The x-axis shows temperature (° C.) and the y-axis heat flow (watts/g).
Figure 2:
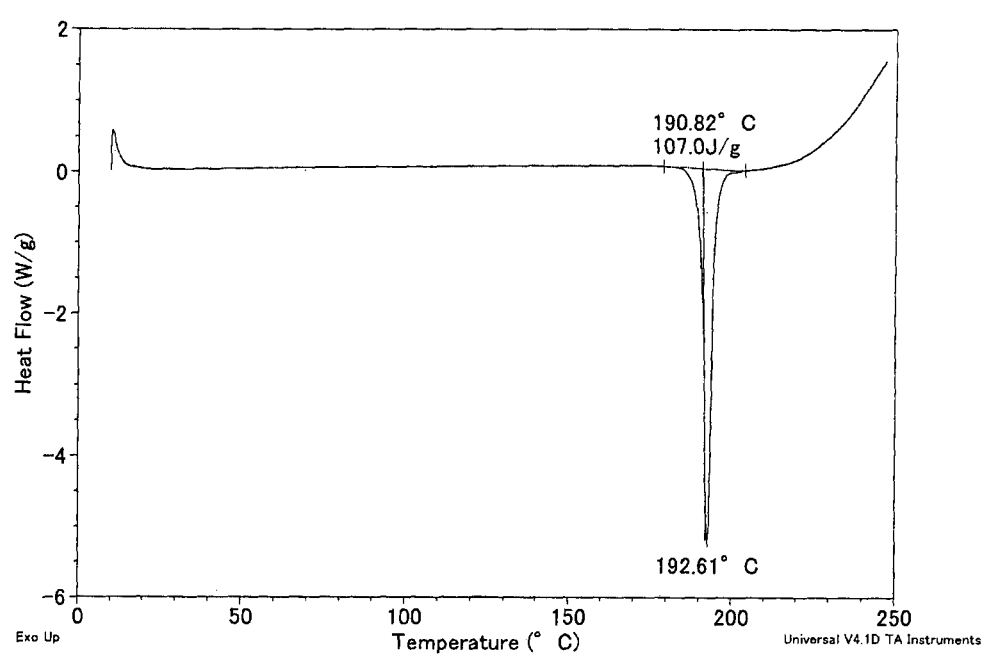
FIG. 2 is a differential scanning calorimetry (DSC) trace for Compound of Example 19 (Form A). The x-axis shows temperature (° C.) and the y-axis heat flow (watts/g).
Figure 3:
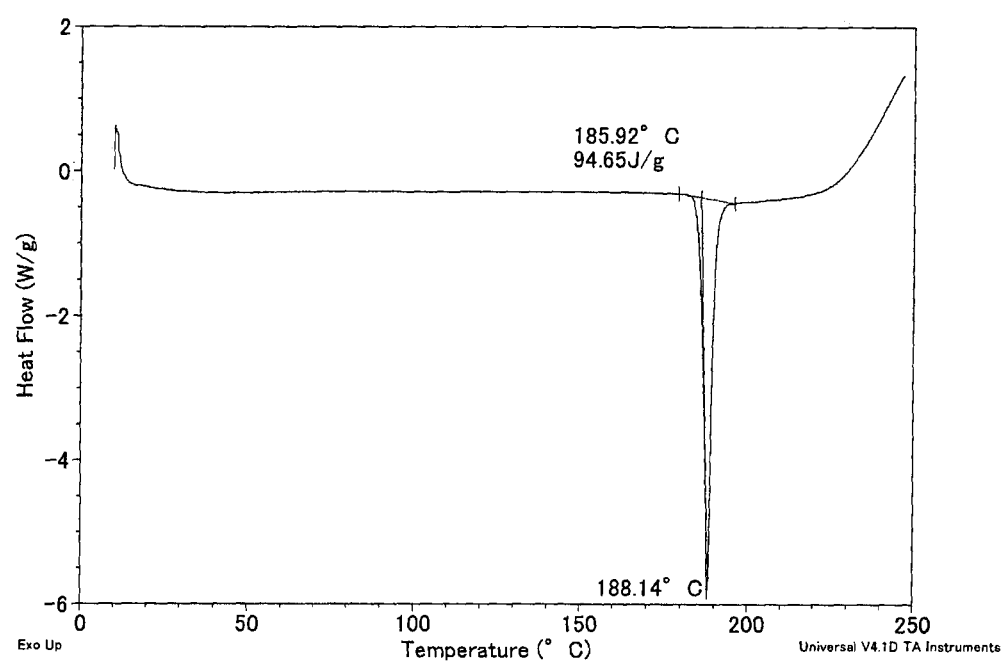
FIG. 3 is a differential scanning calorimetry (DSC) trace for Compound of Example 20 (Form E). The x-axis shows temperature (° C.) and the y-axis heat flow (watts/g).
Figure 4:
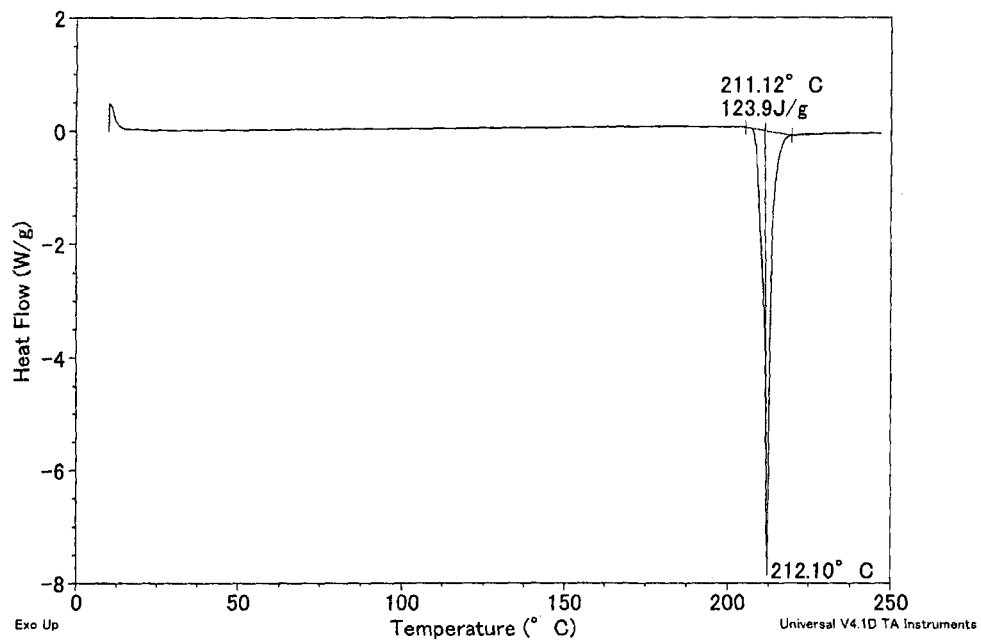
FIG. 4 is a differential scanning calorimetry (DSC) trace for Compound of Example 21 (Form A). The x-axis shows temperature (° C.) and the y-axis heat flow (watts/g).

According to a first aspect of the present disclosure, there is therefore provided at least one such entity chosen from compounds of Formula (I):

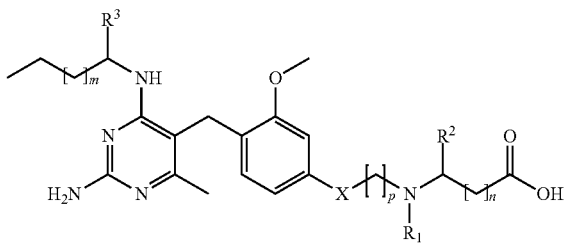

(I)

wherein:
n is 0, 1, or 2;
m is 1 or 2;
p is 1, 2 or 3, provided that when X is oxygen, p is 2 or 3, and when X is a single bond, p is 1;
X is oxygen or a single bond;
$R^1$ is chosen from hydrogen, $C_{1-4}$ alkyl groups, $C_{1-3}$ alkyl-$(CH_2)$— groups wherein the $C_{1-3}$ alkyl moiety is substituted by 1, 2, or 3 fluorine atoms, $C_{1-4}$ alkyl groups substituted by cyano, $C_{1-3}$ alkoxy-$C_{2-4}$ alkyl groups, $C_{3-6}$ cycloalkyl groups, $C_{1-4}$ alkylcarbonyl groups, and formyl;
$R^2$ is chosen from hydrogen and $C_{1-4}$ alkyl groups;
or $R^1$ and $R^2$ together with the nitrogen and carbon atoms to which they are attached form a ring chosen from saturated and unsaturated 4- to 6-membered heterocyclyl rings that optionally contain a further heteroatom chosen from N, O, and S, wherein said N heteroatom may be optionally substituted by $C_{1-3}$ alkyl;
$R^3$ is chosen from hydrogen, hydroxymethyl, and 2-hydroxyethyl;
and pharmaceutically acceptable salts thereof.

It is to be understood that certain of the compounds of Formula (I) defined above and/or their pharmaceutically acceptable salts may exist in optically active or racemic forms by virtue of one or more asymmetric carbon atoms, the present disclosure includes in its scope any such optically active or racemic form. The synthesis of optically active forms may be carried out by standard techniques of organic chemistry well known in the art, for example, by synthesis from optically active starting materials or by resolution of a racemic form. The above-mentioned activity may be evaluated using the standard laboratory techniques referred to hereinafter.

It is to be understood that certain compounds of Formula (I) above and/or their pharmaceutically acceptable salts may exist in unsolvated forms as well as solvated forms, such as, for example, hydrated forms. It is to be understood that the present disclosure encompasses all such solvated forms.

It is also to be understood that certain compounds of the Formula (I) and/or their pharmaceutically acceptable salts may exist in crystalline form and exhibit polymorphism. The present disclosure encompasses all such forms.

The term "$C_{1-4}$ alkyl" is intended to mean a saturated carbon chain of 1 to 4 carbon atoms in length which may be straight chained or branched. However, references to individual alkyl groups such as, for example, "propyl" are specific for the straight chain version only and references to individual branched chain alkyl groups such as, for example, tert butyl are specific for the branched chain version only. Non-limiting examples of "$C_{1-4}$ alkyl" include methyl, ethyl, propyl, isopropyl, butyl, n-butyl, isobutyl, and tert-butyl. The terms "$C_{2-4}$ alkyl" and "$C_{1-3}$ alkyl" are to be construed accordingly.

The term "$C_{1-3}$ alkoxy" is intended to mean an alkoxy group with saturated carbon chain of 1 to 3 carbon atoms in length which may be straight chained or branched. However references to individual alkoxy groups such as "propoxy" are specific for the straight chain version only and references to individual branched chain alkoxy groups such as isopropoxy are specific for the branched chain version only. Non-limiting examples of "$C_{1-3}$ alkoxy" include methoxy, ethoxy, propoxy, and isopropoxy.

The term "$C_{1-3}$ alkoxy-$C_{2-4}$ alkyl" is intended to mean a $C_{2-4}$ alkyl substituted by $C_{1-3}$ alkoxy.

The term "$C_{1-3}$ alkyl-$(CH_2)$— wherein the $C_{1-3}$ alkyl moiety is substituted by 1, 2, or 3 fluorine atoms" is intended to mean a methylene group bound to a $C_{1-3}$ alkyl moiety in which 1, 2, or 3 hydrogen atoms are replaced by fluorine atoms. Non-limiting examples of "$C_{1-3}$ alkyl-$(CH_2)$— wherein the $C_{1-3}$ alkyl moiety is substituted by 1, 2, or 3 fluorine atoms" include 2-monofluoroethyl, 2,2-difluoroethyl, and 2,2,2-trifluoroethyl.

The term "$C_{1-4}$ alkyl substituted by cyano" is intended to mean a $C_{1-4}$ alkyl substituted by cyano.

The term "$C_{3-6}$ cycloalkyl" is intended to mean a 3- to 6-membered saturated cycloalkyl. Non-limiting examples of "$C_{3-6}$ cycloalkyl" include cyclopropyl, cyclobutyl, cyclopentyl, and cyclohexyl.

The term "$C_{1-4}$ alkylcarbonyl" is intended to mean a carbonyl group substituted by $C_{1-4}$ alkyl. Non-limiting examples of "$C_{1-4}$ alkylcarbonyl" include acetyl, ethanoyl, propanoyl, butanoyl, pentanoyl, 2-methylpropanoyl, and 3-methylbutanoyl.

The term "saturated 4- to 6-membered heterocyclyl ring" which is formed by $R^1$ and $R^2$ together with the nitrogen and carbon atoms to which they are attached is intended to mean a saturated 4-, 5-, or 6-membered heterocyclyl ring. That ring may optionally containing a further heteroatom chosen from N, O, and S, wherein said N atom may be optionally substituted by $C_{1-3}$ alkyl. Non-limiting examples of such saturated 4- to 6-membered heterocyclyl rings include pyrrolidinyl, piperidinyl, morpholino, and piperazinyl.

In the case where a "saturated or unsaturated 4- to 6-membered heterocyclyl ring" is substituted by $C_{1-3}$ alkyl on N atom, any hydrogen atom on an available N atom can be replaced by $C_{1-3}$ alkyl. A non-limiting example of an "available" nitrogen atom which may be optionally substituted by $C_{1-3}$ alkyl is the nitrogen at the 4 position of a piperazin-1-yl group.

The term "unsaturated 4- to 6-membered heterocyclyl ring" which is formed by $R^1$ and $R^2$ together with the nitrogen and carbon atoms to which they are attached is intended to mean an unsaturated 4-, 5-, or 6-membered heterocyclyl ring. That ring may optionally containing a further heteroatom chosen from N, O, and S, wherein said N atom may be optionally substituted by $C_{1-3}$ alkyl. Non-limiting examples of the "unsaturated 4- to 6-membered heterocyclyl ring" include unsaturated 5- and 6-membered heterocyclyl rings. Additional non-limiting examples of unsaturated 4- to 6-membered heterocyclyl rings include imidazolyl, pyrazolyl, and thiazolyl.

In an embodiment, the at least one entity is chosen from compounds of Formula (IA):

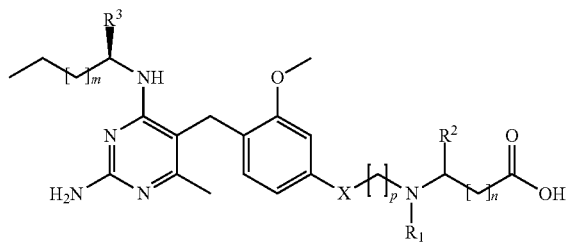

(IA)

and pharmaceutically acceptable salts thereof, wherein the values of X, $R^1$, $R^2$, $R^3$, m, n, and p may take any of the values defined in Formula (I), above.

Non-limiting examples of the values that X, $R^1$, $R^2$, $R^3$, m, n, and p in Formula (I) and/or Formula (IA) may take are indicated below. Such values may be used together with any of the definitions, claims, aspects, and/or embodiments defined herein to provide further embodiments or claims of the present disclosure, and unless the context does not permit, any number of said variable group definitions may be used in any combination with each other to form further embodiments, aspects, and/or claims.

(i) m is 1;
(ii) m is 2;
(iii) n is 0 or 1;
(iv) n is 0;
(v) n is 1;
(vi) n is 2;
(vii) X is a single bond and p is 1;
(viii) X is an oxygen atom and p is 2;
(ix) X is an oxygen atom and p is 3;
(x) $R^1$ is chosen from $C_{1-4}$ alkyl groups, $C_{1-3}$ alkyl-$(CH_2)$— groups wherein the $C_{1-3}$ alkyl moiety is substituted by 1, 2, or 3 fluorine atoms, $C_{1-4}$ alkyl groups substituted by cyano, $C_{1-3}$ alkoxy-$C_{2-4}$ alkyl groups, $C_{3-6}$ cycloalkyl groups, $C_{1-4}$ alkylcarbonyl groups, and formyl;
(xi) $R^1$ is chosen from ethyl, 2-monofluoroethyl, 2,2-difluoroethyl, 2,2,2-trifluoroethyl, and acetyl;
(xii) $R^1$ is chosen from ethyl, 2,2-difluoroethyl, 2,2,2-trifluoroethyl, and acetyl;
(xiii) $R^1$ is chosen from $C_{1-4}$ alkyl groups;
(xiv) $R^1$ is chosen from $C_{1-3}$ alkyl groups;
(xv) $R^1$ is chosen from methyl, ethyl, and propyl;
(xvi) $R^1$ is ethyl optionally substituted by 1, 2, or 3 fluorine atom(s);
(xvii) $R^1$ is ethyl;
(xviii) $R^1$ is 2,2-difluoroethyl or 2,2,2-trifluoroethyl;
(xix) $R^1$ is 2,2-difluoroethyl;
(xx) $R^1$ is 2,2,2-trifluoroethyl;
(xxi) $R^1$ is chosen from $C_{1-4}$ alkylcarbonyl groups;
(xxii) $R^1$ is acetyl;
(xxiii) $R^2$ is chosen from hydrogen and $C_{1-4}$ alkyl groups;
(xxiv) $R^2$ is chosen from hydrogen and $C_{1-2}$ alkyl groups;
(xxv) $R^2$ is hydrogen or methyl;
(xxvi) $R^2$ is hydrogen;
(xxvii) $R^1$ and $R^2$ together with the nitrogen atom and carbon atoms to which they are attached form a saturated or unsaturated 4- to 6-membered heterocyclyl ring optionally containing a further heteroatom chosen from N, O, and S, wherein said N heteroatom may be optionally substituted by $C_{1-3}$ alkyl;
(xxviii) $R^1$ and $R^2$ together with the nitrogen and carbon atoms to which they are attached form a saturated 4- to 6-membered heterocyclyl ring optionally containing a further heteroatom chosen from N, O, and S, wherein said N heteroatom may be optionally substituted by $C_{1-3}$ alkyl;
(xxix) $R^1$ and $R^2$ together with the nitrogen and carbon atoms to which they are attached form a pyrrolidinyl, piperidinyl, morpholino, or piperazinyl ring wherein the nitrogen atom at the 4 position is optionally substituted by $C_{1-3}$ alkyl;
(xxx) $R^1$ and $R^2$ together with the nitrogen and carbon atoms to which they are attached form a pyrrolidinyl, piperidinyl, or morpholino ring wherein the nitrogen atom at the 4 position is optionally substituted by $C_{1-3}$ alkyl;
(xxxi) $R^1$ and $R^2$ together with the nitrogen and carbon atoms to which they are attached form a pyrrolidinyl ring;
(xxxii) $R^1$ and $R^2$ together with the nitrogen and carbon atoms to which they are attached form an unsaturated 5- to 6-membered heterocyclyl ring optionally containing a further heteroatom chosen from N, O, and S, wherein said N heteroatom may be optionally substituted by $C_{1-3}$ alkyl;
(xxxiii) $R^1$ and $R^2$ together with the nitrogen and carbon atoms to which they are attached form an imidazolyl ring;

(xxxiv) $R^3$ is hydrogen, hydroxymethyl, or 2-hydroxyethyl;
(xxxv) $R^3$ is hydrogen or 2-hydroxyethyl; and
(xxxvi) $R^3$ is 2-hydroxyethyl.

In one embodiment of the present disclosure, there is provided a compound of Formula (I) or Formula (IA), wherein X is a single bond, p is 1, and n is 0 or 1.

In one embodiment of the present disclosure, there is provided a compound of Formula (I) or Formula (IA), wherein X is a single bond, p is 1, n is 0 or 1, and $R^2$ is hydrogen.

In one embodiment of the present disclosure, there is provided a compound of Formula (I) or Formula (IA), wherein X is a single bond, p is 1, n is 0 or 1, and $R^1$ and $R^2$ together with the nitrogen and carbon atoms to which they are attached form a saturated or unsaturated 4- to 6-membered heterocyclyl ring optionally containing a further heteroatom chosen from N, O, and S, wherein said N heteroatom may be optionally substituted by $C_{1-3}$ alkyl.

In one embodiment of the present disclosure, there is provided a compound of Formula (I) or Formula (IA), wherein X is a single bond, p is 1, and n is 0.

In one embodiment of the present disclosure, there is provided a compound of Formula (I) or Formula (IA), wherein X is a single bond, p is 1, n is 0, and $R^2$ is hydrogen.

In one embodiment of the present disclosure, there is provided a compound of Formula (I) or Formula (IA), wherein X is oxygen, p is 3, and n is 0.

In one embodiment of the present disclosure, there is provided a compound of Formula (I) or Formula (IA), wherein X is oxygen, p is 3, n is 0, and $R^1$ and $R^2$ together with the nitrogen and carbon atoms to which they are attached form a saturated or unsaturated 4 to 6-membered heterocyclyl ring optionally containing a further heteroatom chosen from N, O, and S, wherein said N heteroatom may be optionally substituted by $C_{1-3}$ alkyl.

In one embodiment of the present disclosure, there is provided a compound of Formula (I) or Formula (IA), wherein X is oxygen, p is 3, n is 0, and $R^1$ and $R^2$ combine together with adjacent nitrogen atom and carbon atom form pyrrolidinyl or imidazolyl.

In one embodiment of the present disclosure, there is provided a compound of Formula (I) or Formula (IA), wherein m is 1 and $R^3$ is 2-hydroxyethyl.

In one embodiment of the present disclosure there is provided at least one entity chosen from compounds of Formula (I) and/or compounds of Formula (IA), wherein:
  n is 0 or 1;
  m is 1;
  p is 1 or 3, provided that when X is oxygen, p is 3 and when X is a single bond, p is 1;
  X is oxygen or a single bond;
  $R^1$ is chosen from $C_{1-4}$ alkyl groups, $C_{1-3}$ alkyl-(CH$_2$)— groups wherein the $C_{1-3}$ alkyl moiety is substituted by 1, 2, or 3 fluorine atoms, $C_{1-4}$ alkyl groups substituted by cyano, and $C_{1-4}$ alkylcarbonyl groups;
  $R^2$ is hydrogen;
  or $R^1$ and $R^2$ together with the nitrogen and carbon atoms to which they are attached form a pyrrolidinyl, imidazolyl, or morpholino ring;
  $R^3$ is hydrogen or 2-hydroxyethyl;
and pharmaceutically acceptable salts thereof.

In one embodiment of the present disclosure there is provided at least one entity chosen from compounds of Formula (I) and/or compounds of Formula (IA), wherein:
  n is 0;
  m is 1;
  p is 1;
  X is a single bond;
  $R^1$ is chosen from $C_{1-4}$ alkyl groups, $C_{1-3}$ alkyl-(CH$_2$)— groups wherein the $C_{1-3}$ alkyl moiety is substituted by 1, 2, or 3 fluorine atoms, $C_{1-4}$ alkyl groups substituted by cyano, and $C_{1-4}$ alkylcarbonyl groups;
  $R^2$ is hydrogen;
  or $R^1$ and $R^2$ together with the nitrogen and carbon atoms to which they are attached form a pyrrolidinyl, imidazolyl, or morpholino ring;
  $R^3$ is hydrogen or 2-hydroxyethyl;
and pharmaceutically acceptable salts thereof.

In one embodiment of the present disclosure there is provided at least one entity chosen from compounds of Formula (I) and/or compounds of Formula (IA), wherein:
  n is 0;
  m is 1;
  p is 1;
  X is a single bond;
  $R^1$ is $C_{1-4}$ alkyl groups, $C_{1-3}$ alkyl-(CH$_2$)— groups wherein the $C_{1-3}$ alkyl moiety is substituted by 1, 2, or 3 fluorine atoms;
  $R^2$ is hydrogen; and
  $R^3$ is hydrogen or 2-hydroxyethyl;
and pharmaceutically acceptable salts thereof.

In one embodiment of the present disclosure, there is provided at least one entity chosen from:
2-((4-((2-amino-4-(1-hydroxyhexan-3-ylamino)-6-methylpyrimidin-5-yl)methyl)-3-methoxybenzyl)(ethyl)amino)acetic acid;
2-((4-((2-amino-4-(butylamino)-6-methylpyrimidin-5-yl)methyl)-3-methoxybenzyl)(ethyl)amino)acetic acid;
2-((4-((2-amino-4-(1-hydroxyhexan-3-ylamino)-6-methylpyrimidin-5-yl)methyl)-3-methoxybenzyl)(2,2-difluoroethyl)amino)acetic acid;
2-((4-((2-amino-4-(1-hydroxyhexan-3-ylamino)-6-methylpyrimidin-5-yl)methyl)-3-methoxybenzyl)(2,2,2-trifluoroethyl)amino)acetic acid;
3-((4-((2-amino-4-(1-hydroxyhexan-3-ylamino)-6-methylpyrimidin-5-yl)methyl)-3-methoxybenzyl)(ethyl)amino)propanoic acid; 3-((4-((2-amino-4-(1-hydroxyhexan-3-ylamino)-6-methylpyrimidin-5-yl)methyl)-3-methoxybenzyl)(2,2-difluoroethyl)amino)propanoic acid;
2-(N-(4-((2-amino-4-(1-hydroxyhexan-3-ylamino)-6-methylpyrimidin-5-yl)methyl)-3-methoxybenzyl)acetamido)acetic acid;
1-(3-(4-((2-amino-4-(1-hydroxyhexan-3-ylamino)-6-methylpyrimidin-5-yl)methyl)-3-methoxyphenoxy)propyl)pyrrolidine-2-carboxylic acid;
3-((3-(4-((2-amino-4-(1-hydroxyhexan-3-ylamino)-6-methylpyrimidin-5-yl)methyl)-3-methoxyphenoxy)propyl)(ethyl)amino)propanoic acid;
2-((3-(4-((2-amino-4-(1-hydroxyhexan-3-ylamino)-6-methylpyrimidin-5-yl)methyl)-3-methoxyphenoxy)propyl)(ethyl)amino)acetic acid;
2-((3-(4-((2-amino-4-(1-hydroxyhexan-3-ylamino)-6-methylpyrimidin-5-yl)methyl)-3-methoxyphenoxy)propyl)(2,2-difluoroethyl)amino)acetic acid;
1-(4-((2-amino-4-(1-hydroxyhexan-3-ylamino)-6-methylpyrimidin-5-yl)methyl)-3-methoxybenzyl)pyrrolidine-2-carboxylic acid;
1-(4-((2-amino-4-(1-hydroxyhexan-3-ylamino)-6-methylpyrimidin-5-yl)methyl)-3-methoxybenzyl)-1H-imidazole-5-carboxylic acid;
and pharmaceutically acceptable salts thereof.

In one embodiment of the present disclosure, there is provided at least one entity chosen from (S)-2-((4-((2-amino-4-(1-hydroxyhexan-3-ylamino)-6-methylpyrimidin- 5-yl)methyl)-3-methoxybenzyl)(ethyl)amino)acetic acid and pharmaceutically acceptable salts thereof.

In one embodiment of the present disclosure, there is provided (S)-2-((4-((2-amino-4-(1-hydroxyhexan-3-ylamino)-6-methylpyrimidin-5-yl)methyl)-3-methoxybenzyl)(ethyl)amino)acetic acid.

In one embodiment of the present disclosure, there is provided at least one entity chosen from pharmaceutically acceptable salts of (S)-2-((4-((2-amino-4-(1-hydroxyhexan-3-ylamino)-6-methylpyrimidin-5-yl)methyl)-3-methoxybenzyl)(ethyl)amino)acetic acid.

In one embodiment of the present disclosure, there is provided at least one entity chosen from (S)-2-((4-((2-amino-4-(1-hydroxyhexan-3-ylamino)-6-methylpyrimidin-5-yl)methyl)-3-methoxybenzyl)(2,2-difluoroethyl)amino) acetic acid and pharmaceutically acceptable salts thereof.

In one embodiment of the present disclosure, there is provided (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid.

In one embodiment of the present disclosure, there is provided at least one entity chosen from pharmaceutically acceptable salts of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid.

In one embodiment of the present disclosure, there is provided at least one entity chosen from (S)-2-((4-((2-amino-4-(1-hydroxyhexan-3-ylamino)-6-methylpyrimidin-5-yl)methyl)-3-methoxybenzyl)(2,2,2-trifluoroethyl)amino) acetic acid and pharmaceutically acceptable salts thereof.

In one embodiment of the present disclosure, there is provided (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid.

In one embodiment of the present disclosure, there is provided at least one entity chosen from pharmaceutically acceptable salts of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid.

A further aspect of the invention is any of the embodiments defined herein with the proviso that one or more specific Examples, such as Example 1, Example 2, Example 3, Example 4, Example 5, Example 6 etc. are individually disclaimed.

As previously mentioned, some compounds of formula (I) may exhibit polymorphism. It is generally known that crystalline materials may be analysed using conventional techniques such as X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, the compound of Example 3 exhibits polymorphism and three crystalline forms are identified herein.

Accordingly, a further aspect of the invention is Form B of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid.

According to a further aspect of the present invention, there is provided a crystalline form, Form B of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least one specific peak at about 2-theta=6.5°.

According to a further aspect of the present invention, there is provided a crystalline form, Form B of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least one specific peak at about 2-theta=9.5°.

According to a further aspect of the present invention, there is provided a crystalline form, Form B of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least two specific peaks at about 2-theta=6.5° and 9.5°.

According to a further aspect of the present invention, there is provided a crystalline form, Form B of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with specific peaks at about 2-theta=6.5, 9.5, 10.1, 10.9, 13.9, 15.2, 16.5 and 16.8°.

Figure 5:
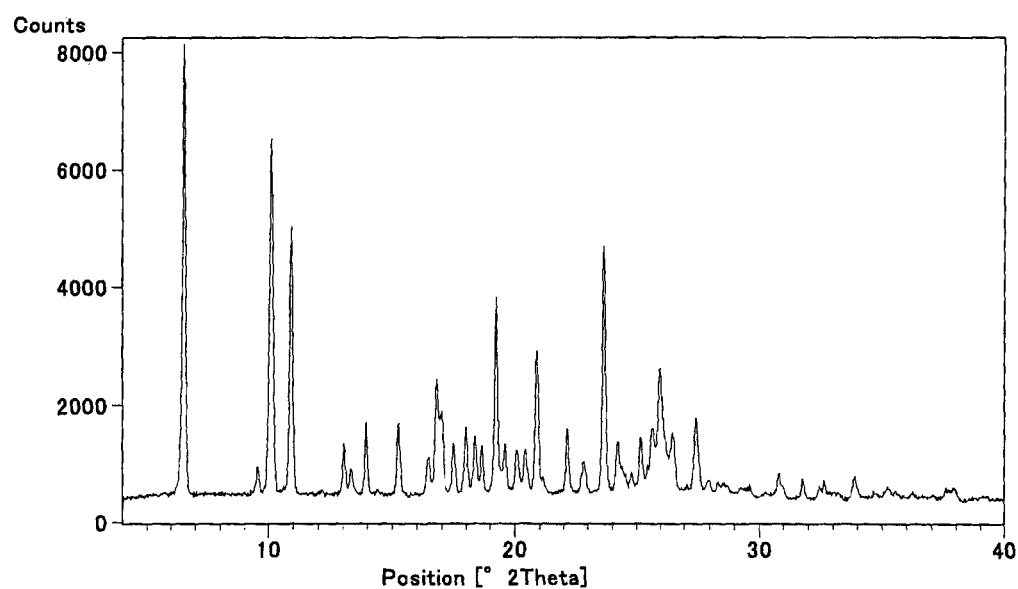
FIG. 5 is an X-ray powder diffraction pattern of Compound of Example 18 (Form B) x-axis shows the 2-theta value and the y-axis the intensity.

According to a further aspect of the present invention, there is provided a crystalline form, Form B of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern substantially the same as the X-ray powder diffraction pattern shown in FIG. 5.

A further aspect of the invention is Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least one specific peak at about 2-theta=7.9°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least one specific peak at about 2-theta=12.4°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with at least two specific peaks at about 2-theta=7.9° and 12.4°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern with specific peaks at about 2-theta=7.9, 10.9, 12.4, 13.1, 14.7, 15.7, 16.3 and 17.0°.

Figure 6:
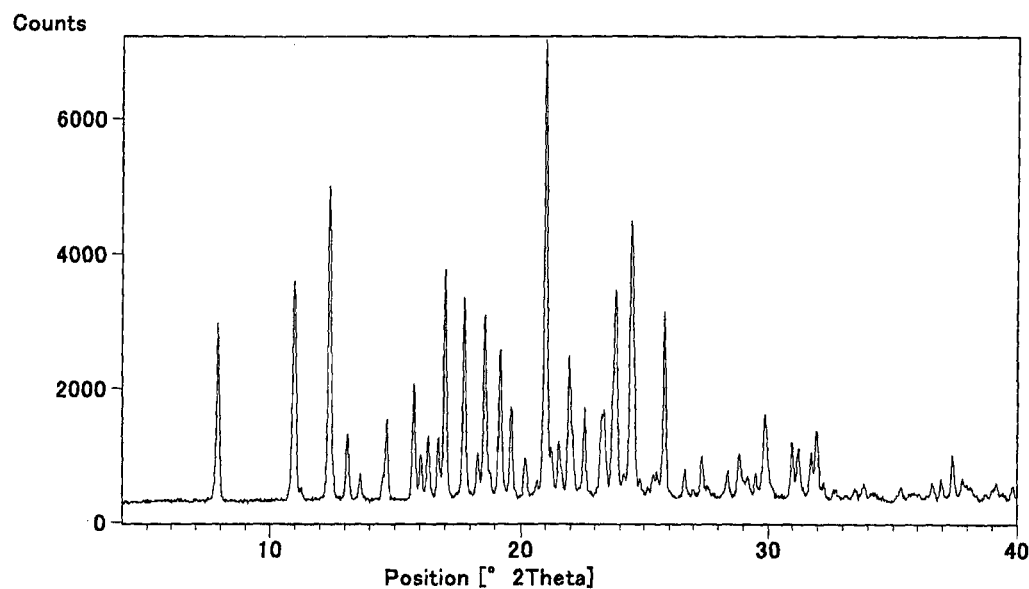
FIG. 6 is an X-ray powder diffraction pattern of Compound of Example 19 (Form A) x-axis shows the 2-theta value and the y-axis the intensity.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2-difluoroethyl) amino)acetic acid, which has an X-ray powder diffraction pattern substantially the same as the X-ray powder diffraction pattern shown in FIG. 6.

A further aspect of the invention is Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid.

According to a further aspect of the present invention, there is provided a crystalline form, Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid, which has an X-ray powder diffraction pattern with at least one specific peak at about 2-theta=8.2°.

According to a further aspect of the present invention, there is provided a crystalline form, Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid, which has an X-ray powder diffraction pattern with at least one specific peak at about 2-theta=11.6°.

According to a further aspect of the present invention, there is provided a crystalline form, Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid, which has an X-ray powder diffraction pattern with at least two specific peaks at about 2-theta=8.2° and 11.6°.

According to a further aspect of the present invention, there is provided a crystalline form, Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid, which has an X-ray powder diffraction pattern with specific peaks at about 2-theta=8.2, 11.6, 11.9, 12.9, 14.7, 15.6, 16.3 and 18.3°.

Figure 7:
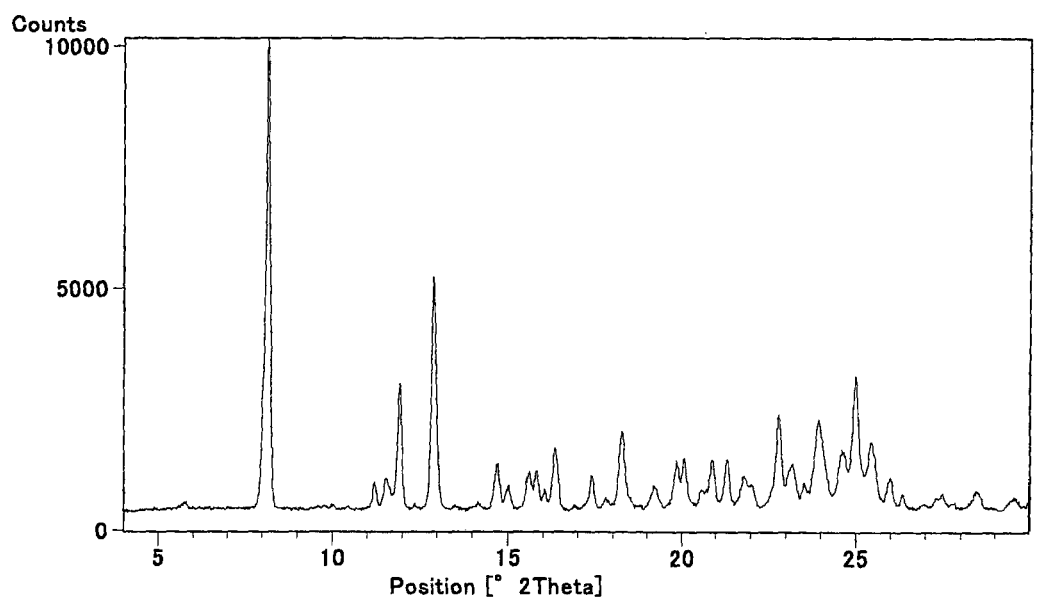
FIG. 7 is an X-ray powder diffraction pattern of Compound of Example 20 (Form E) x-axis shows the 2-theta value and the y-axis the intensity.

According to a further aspect of the present invention, there is provided a crystalline form, Form E of (S)-2-((4-((2-amino-4-(1-hydroxyhexan-3-ylamino)-6-methylpyrimidin-5-yl)methyl)-3-methoxybenzyl)(2,2-difluoroethyl)amino)acetic acid, which has an X-ray powder diffraction pattern substantially the same as the X-ray powder diffraction pattern shown in FIG. 7.

It has been found that the compound of Example 4 also exhibits polymorphism, and one crystalline form is identified herein.

Accordingly, a further aspect of the invention is Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, which has an X-ray powder diffraction pattern with at least one specific peak at about 2-theta=10.9°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, which has an X-ray powder diffraction pattern with at least one specific peak at about 2-theta=12.3°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, which has an X-ray powder diffraction pattern with at least two specific peaks at about 2-theta=10.9° and 12.3°.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, which has an X-ray powder diffraction pattern with specific peaks at about 2-theta=7.9, 10.9, 12.3, 13.0, 15.7, 16.3, 16.9 and 17.8°.

Figure 8:
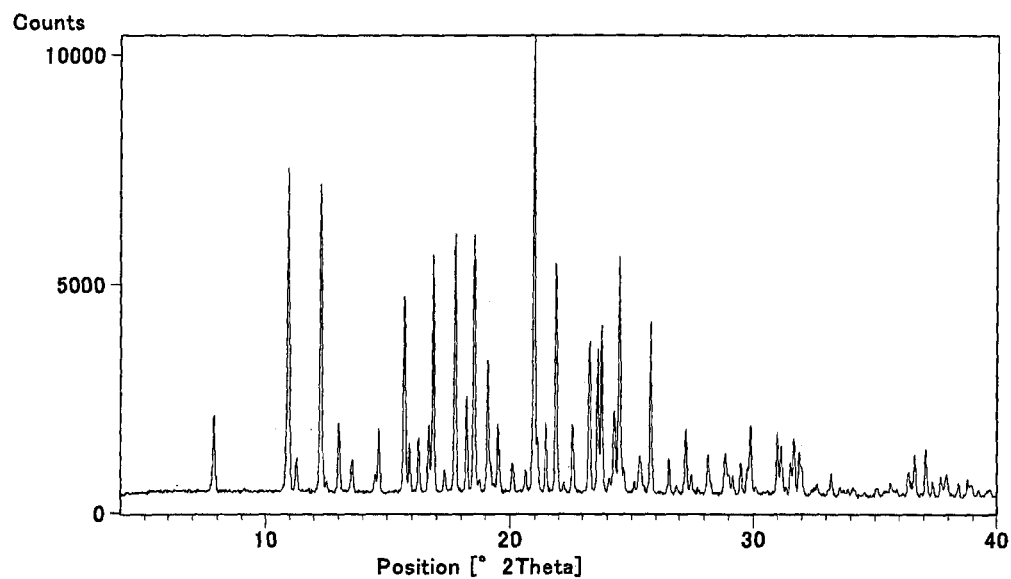
FIG. 8 is an X-ray powder diffraction pattern of Compound of Example 21 (Form A) x-axis shows the 2-theta value and the y-axis the intensity.

According to a further aspect of the present invention, there is provided a crystalline form, Form A of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, which has an X-ray powder diffraction pattern substantially the same as the X-ray powder diffraction pattern shown in FIG. 8.

It will be understood that 2-theta values of X-ray powder diffraction patterns may vary slightly from one machine to another or from one sample to another, and so the values quoted herein are not to be construed as absolute (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures). Generally, a measurement error of a diffraction angle in an X-ray powder diffractogram is for example approximately plus or minus 0.1° 2-theta, and such degree of a measurement error should be taken into account when considering the X-ray powder diffraction data. Furthermore, it should be understood that intensities might fluctuate depending on experimental conditions and sample preparation (preferred orientation).

In a further aspect of the invention, there is provided a crystalline form characterised by the XRD 2-theta values recited herein, wherein said 2-theta values are plus or minus 0.1 2-theta.

It is also known that an X-ray powder diffraction pattern may be obtained which has one or more measurement errors depending on measurement conditions (such as the equipment or machine used). For example, the relative intensity of peaks can be affected by grains above 30 microns in size and non-unitary aspect ratios. The skilled person will also realize that the position of reflections can be affected by the precise height at which the sample sits in the diffractometer and the zero calibration of the diffractometer. The surface planarity of the sample may also have a small effect. Therefore it should be understood that the crystalline Forms of the present invention described above, unless otherwise stated, are not limited to the crystals that provide X-ray powder diffraction patterns identical to the X-ray powder diffraction pattern shown in FIGS. 5, 6, 7 and 8 and any crystals providing X-ray powder diffraction patterns substantially the same as those shown in these Figures fall within the scope of the present invention. A person skilled in the art of X-ray powder diffraction is able to judge the substantial identity of X-ray powder diffraction patterns.

In the case where X is a single bond and p is 0 in Formula (I), a compound of Formula (I) may be prepared by the sequence shown in Scheme 1:

Scheme 1

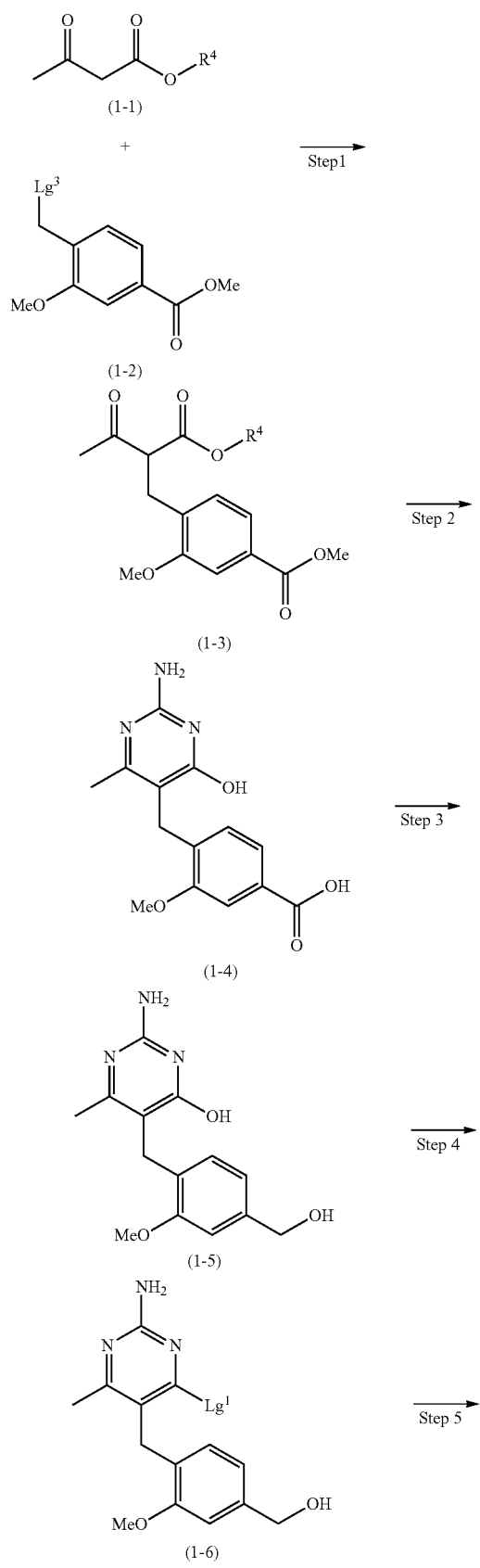
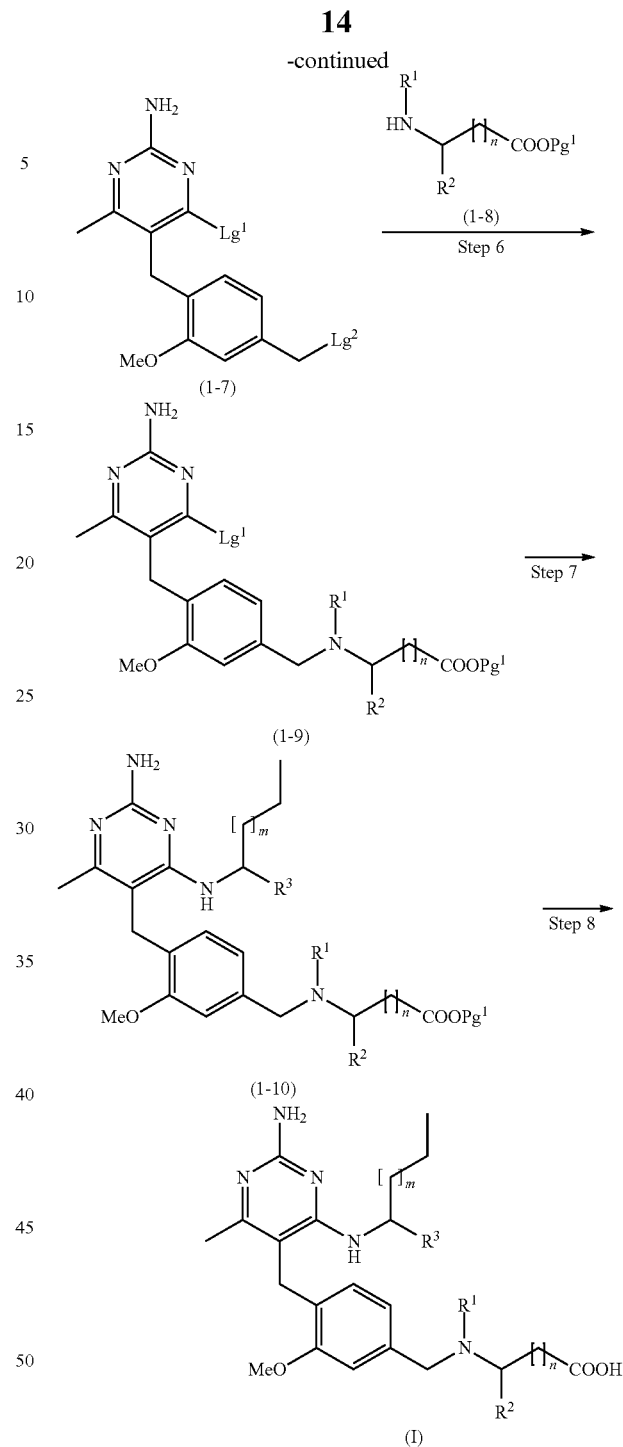

wherein m, n, $R^1$, $R^2$, and $R^3$ are as defined in Formula (I), $R^4$ is chosen from $C_{1-4}$ alkyl groups, and the $Lg^1$, $Lg^2$, and $Lg^3$ groups may be independently chosen from conventional leaving groups which are well-known to the skilled person in the art, for example, substituted and unsubstituted hydrocarbylsulfonyloxy leaving groups, for example, p-toluenesulfonyloxy groups, mesitylenesulfonyloxy, 2,4,6-triisopropylbenzenesulfonyloxy, and methanesulfonyloxy groups, and halo leaving groups such as, for example, iodo, bromo, or chloro leaving groups. The $Pg^1$ group is chosen from protective groups for a carboxylic acid group, for example, an ester such as, for example, a methyl ester, ethyl ester or tert-butyl ester.

(Step 1)

The compounds of Formula (1-3) may be prepared by a standard alkylation reaction using compounds of Formula (1-1) and Formula (1-2). For example, reaction of a compound of Formula (1-1) with a base, such as, for example, NaH, KOtBu, or sodium hexamethyldisilazide, in a suitable solvent, such as, for example, THF or DMF, at a suitable temperature, for example, at a temperature ranging from 0° C. to 20° C., followed by addition of a compound of Formula (1-2). The reaction mixture may be heated, for example, at a temperature ranging from 50° C. to 100° C., optionally in the presence of a catalytic amount of an iodide salt, such as, for example, potassium iodide.

(Step 2)

The compounds of Formula (1-4) may be prepared by reacting a compound of Formula (1-3) with a guanidine or guanidine carbonate in a suitable solvent such as methanol or ethanol, at elevated temperature, for example, at a temperature ranging from 50° C. to 150° C. The compounds of Formula (1-4) may be isolated as a salt.

In one aspect of the present disclosure there is provided at least one entity chosen from compounds of Formula (1-4) as defined in Scheme 1 and salts thereof.

(Step 3)

The compounds of Formula (1-5) may be prepared by reacting a compound of Formula (1-4) with a reducing agent, such as, for example, lithium triethylborohydride or lithium aluminium hydride, in a suitable solvent, such as, for example, THF, at a temperature ranging from 0° C. to 50° C.

In one aspect of the present disclosure, there is provided at least one entity chosen from compounds of Formula (1-5) as defined in Scheme 1 and salts thereof.

(Step 4)

In the case where $Lg^1$ is a hydrocarbylsulfonyloxy leaving group, such as, for example, methanesulfonyloxy, p-toluenesulfonyloxy, mesitylenesulfonyloxy, or 2,4,6-triisopropylbenzenesulfonyloxy, the compounds of Formula (1-6) may be prepared by reacting a compound of Formula (1-5) with a hydrocarbylsulfonyl halide such as, for example, 2-mesitylenesulfonyl chloride or 2,4,6-triisopropylbenzenesulfonyloxy chloride in the presence of a base such as, for example, a trialkylamine, such as, for example, diisopropylethylamine, triethylamine, or 1,4-diazabicyclo[2.2.2]octane, in a suitable solvent such as, for example, THF at a temperature ranging from 0° C. to 50° C.

In one aspect of the present disclosure, there is provided at least one entity chosen from compounds of Formula (1-6) as defined in Scheme 1 and salts thereof.

(Step 5)

In the case where $Lg^2$ is a halogen atom, such as, for example, chloro or bromo, the compounds of Formula (1-7) may be prepared by reacting a compound of Formula (1-6) with a hydrocarbylsulfonyl bromide or chloride in the presence of lithium bromide or lithium chloride, for example, methanesulfonyl chloride with lithium chloride, in a suitable solvent such as, for example, THF at a suitable temperature, for example, at a temperature ranging from 10° C. to 40° C., followed by treatment with an acid such as, for example, HCl in dioxane, in a suitable solvent such as, for example, dichloromethane or THF, at ambient temperature, for example, at a temperature ranging from 10° C. to 40° C.

Alternatively, in the case where $Lg^2$ is a hydrocarbylsulfonyloxy leaving group, such as, for example, methanesulfonyloxy, p-toluenesulfonyloxy, or mesitylenesulfonyloxy, the compounds of Formula (1-7) may be prepared by reacting a compound of Formula (1-6) with a hydrocarbylsulfonyl halide, such as, for example, 2-mesitylenesulfonyl chloride, in the presence of a base, such as, for example, trialkylamine, for example, diisopropylethylamine or triethylamine, in a suitable solvent, such as, for example, THF, at a temperature ranging from 0° C. to 50° C.

In one aspect of the present disclosure, there is provided at least one entity chosen from the compounds of Formula (1-7) as defined in Scheme 1 and salts thereof.

(Step 6)

The compounds of Formula (1-9) may be prepared by reacting a compound of Formula (1-7) with a compound of Formula (1-8) in the presence of a base, such as, for example, potassium bicarbonate or sodium bicarbonate, optionally with potassium iodide or sodium iodide, in a suitable solvent such as, for example, acetonitrile, at a temperature ranging from 0° C. to 100° C. The Step 5 may be followed by the Step 6 successively without isolating the compounds of Formula (1-7).

In one aspect of the present disclosure, there is provided at least one entity chosen from compounds of Formula (1-9) as defined in Scheme 1 and salts thereof.

(Step 7)

The compounds of Formula (1-10) may be prepared reacting a compound of Formula (1-9) with an excess of the appropriate amine or amino alcohol, wherein the amino alcohol may optionally have its alcohol group protected, in a suitable solvent, such as, for example, propionitrile, butanol, anisole, chlorobenzene, or 1,4-dioxane, in the presence of trifluoroacetic acid at elevated temperature, for example, at a temperature ranging from 50° C. to 200° C., using conventional or microwave heating.

In one embodiment, there is provided at least one entity chosen from the compounds of Formula (1-10), as defined herein, and salts thereof.

(Step 8)

The compounds of Formula (I) may be prepared by removing a protective group of carboxylic acid moiety. In the case where $PG^1$ is $C_{1-4}$ alkyl, $PG^1$ may be removed by hydrolysis reaction in the presence of a base such as, for example, aqueous sodium hydroxide, at a temperature ranging from 0° C. to 40° C. In the case where $PG^1$ is tert-butyl, $PG^1$ may be removed by hydrolysis in the presence of an acid such as 0.1 N to 10 N hydrochloric acid or trifluoroacetic acid, at a temperature ranging from 0° C. to 100° C.

In the case where $R^3$ is hydroxymethyl or hydroxyethyl and the hydroxy group is protected by a protective group, the protective group may also be removed according to a method which is well-known by a skilled person in the art.

Alternatively, a compound of Formula (I) may be prepared by the sequence shown in Scheme 2:

Scheme 2

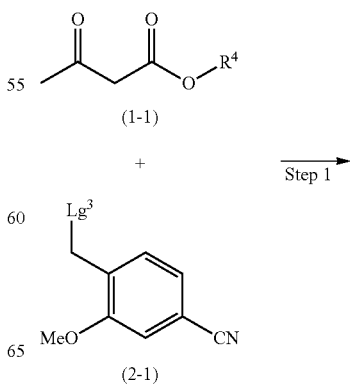

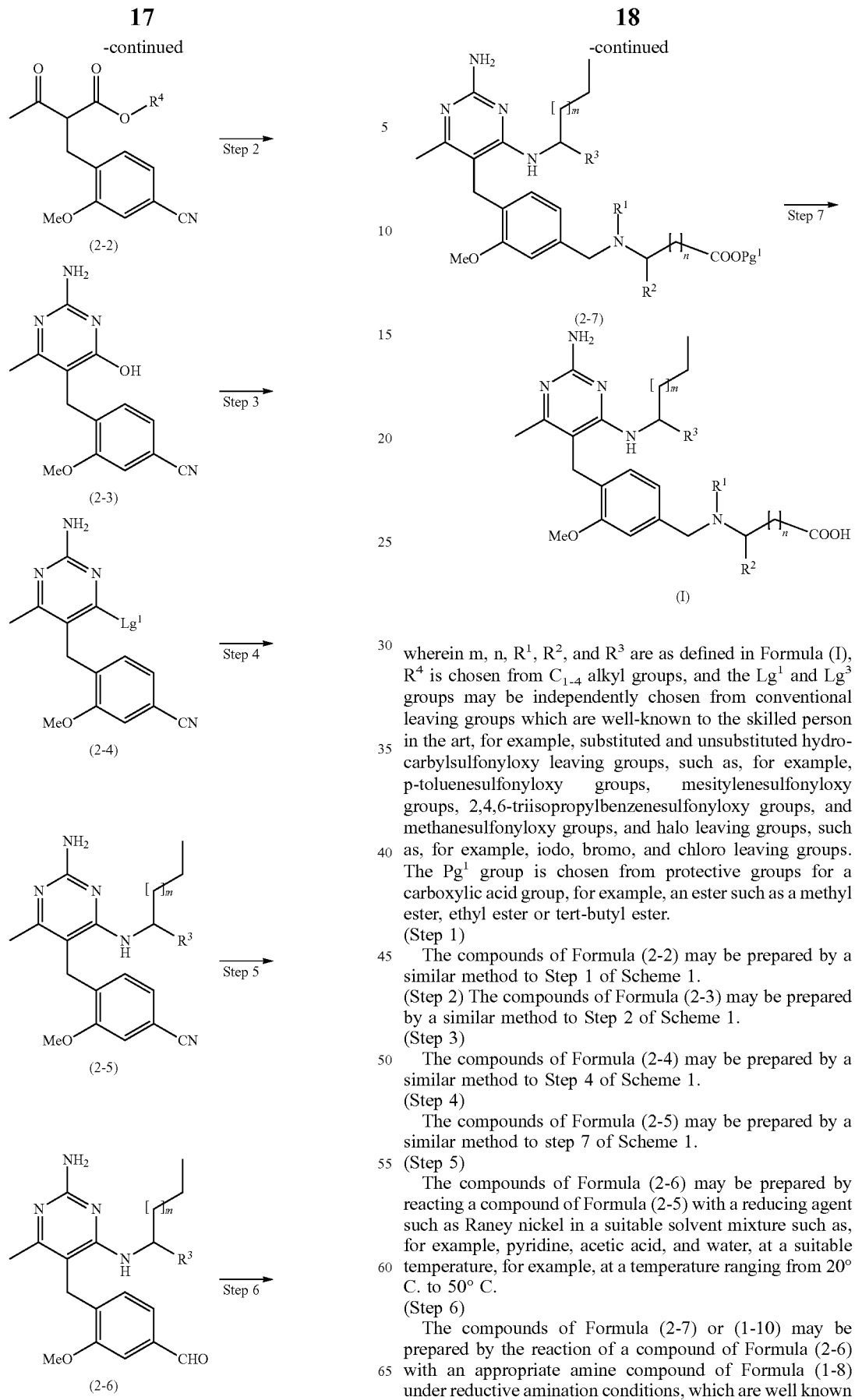

wherein m, n, $R^1$, $R^2$, and $R^3$ are as defined in Formula (I), $R^4$ is chosen from $C_{1-4}$ alkyl groups, and the $Lg^1$ and $Lg^3$ groups may be independently chosen from conventional leaving groups which are well-known to the skilled person in the art, for example, substituted and unsubstituted hydrocarbylsulfonyloxy leaving groups, such as, for example, p-toluenesulfonyloxy groups, mesitylenesulfonyloxy groups, 2,4,6-triisopropylbenzenesulfonyloxy groups, and methanesulfonyloxy groups, and halo leaving groups, such as, for example, iodo, bromo, and chloro leaving groups. The $Pg^1$ group is chosen from protective groups for a carboxylic acid group, for example, an ester such as a methyl ester, ethyl ester or tert-butyl ester.

(Step 1)
The compounds of Formula (2-2) may be prepared by a similar method to Step 1 of Scheme 1.
(Step 2) The compounds of Formula (2-3) may be prepared by a similar method to Step 2 of Scheme 1.
(Step 3)
The compounds of Formula (2-4) may be prepared by a similar method to Step 4 of Scheme 1.
(Step 4)
The compounds of Formula (2-5) may be prepared by a similar method to step 7 of Scheme 1.
(Step 5)
The compounds of Formula (2-6) may be prepared by reacting a compound of Formula (2-5) with a reducing agent such as Raney nickel in a suitable solvent mixture such as, for example, pyridine, acetic acid, and water, at a suitable temperature, for example, at a temperature ranging from 20° C. to 50° C.
(Step 6)
The compounds of Formula (2-7) or (1-10) may be prepared by the reaction of a compound of Formula (2-6) with an appropriate amine compound of Formula (1-8) under reductive amination conditions, which are well known to the skilled person. For example, the reductive amination may be carried out using a suitable reducing agent such as, for example, sodium triacetoxyborohydride, in a suitable solvent such as, for example, dichloromethane and an acid such as, for example, acetic acid in the presence of activated molecular sieves, or by using NaBH$_4$ in a suitable solvent such as, for example, methanol.

(Step 7)

The compounds of Formula (I) may be prepared by a similar method to Step 8 of Scheme 1.

In one embodiment, there is provided at least one entity chosen from compounds of Formula (2-3) and salts thereof. In one embodiment, there is provided at least one entity chosen from compounds of Formula (2-4) and salts thereof. In one embodiment, there is provided at least one entity chosen from compounds of Formula (2-5) and salts thereof. In one embodiment, there is provided at least one entity chosen from compounds of Formula (2-6) and salts thereof.

The optional protecting group incorporated into the compounds of Formula (2-7) or Formula (1-10) may be removed at any convenient point in the synthesis using standard deprotection conditions that are well known to the skilled person. The compounds of Formula (2-7) and the compounds of Formula (1-10) may be isolated as a salt.

In the case where X is oxygen and p is 2 or 3 in Formula (I), a compound of Formula (I) may be prepared by the sequence shown in Scheme 3-1 and 3-2, as follows:

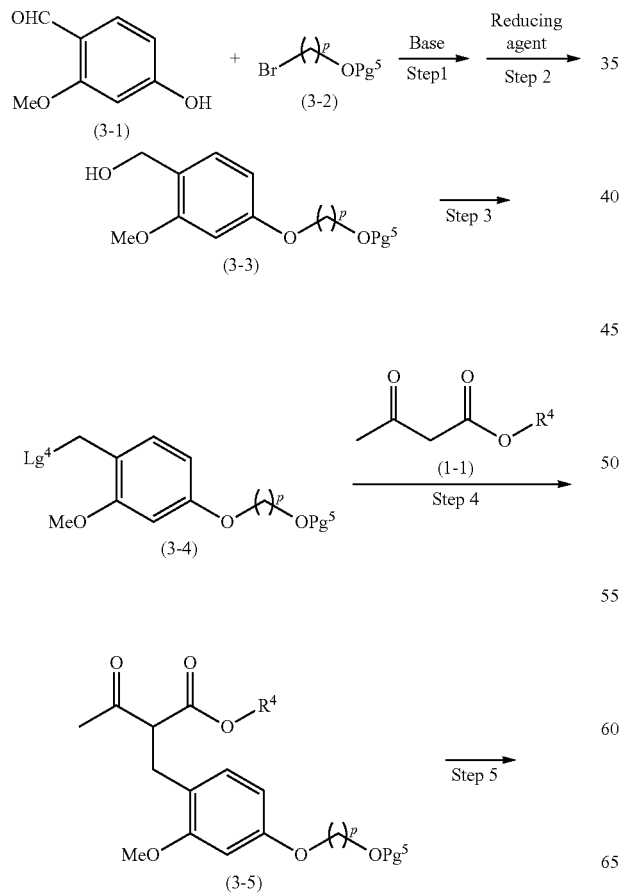

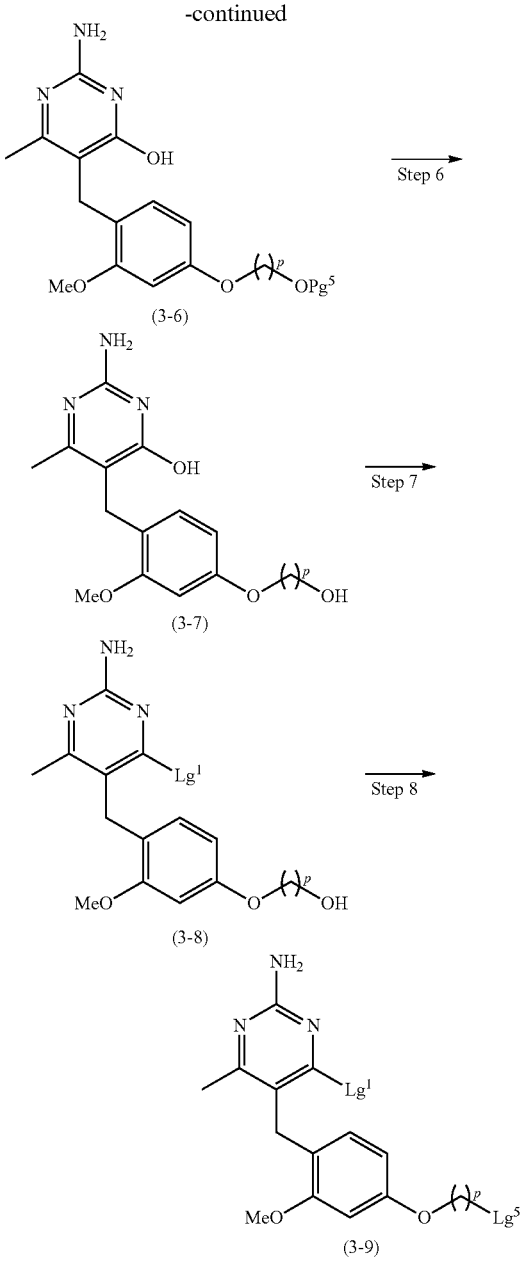

wherein m, n, R$^1$, and R$^2$ are as defined in Formula (I), p is 2 or 3, R$^4$ is chosen from C$_{1-4}$ alkyl groups, and the Lg$^1$, Lg$^4$, and Lg$^3$ groups may be independently chosen from conventional leaving groups which are well-known to the skilled person in the art, for example, substituted and unsubstituted hydrocarbylsulfonyloxy leaving groups, such as, for example, p-toluenesulfonyloxy groups, mesitylenesulfonyloxy groups, 2,4,6-triisopropylbenzenesulfonyloxy groups, and methanesulfonyloxy groups, and or halo leaving group, such as, for example, iodo, bromo, and chloro leaving groups. The Pg$^5$ group is chosen from protective groups for a hydroxy group, for example, a trialkylsilyl group, such as, for example, a t-butyldimethylsilyl group.

(Step 1 and 2)

The compounds of Formula (3-3) may be prepared by a conventional method known to the skilled person in the art. For example, a benzaldehyde compound of Formula (3-1)

may be reacted with a compound of Formula (3-2) in the presence of base, such as, for example, potassium bicarbonate, in a suitable solvent such as, for example, DMF, at ambient temperature, followed by reduction of the product with a reducing agent, such as, for example, sodium borohydride, in a suitable solvent, for example, alcohol, such as, for example, methanol or ethanol, or ether, such as, for example, THF, at a temperature ranging from 0° C. to 40° C., to give the compounds of Formula (3-3).

(Step 3)

The hydroxy group in the compounds of Formula (3-3) may be converted into a conventional leaving group which is well-known to the skilled person in the art, for example, a substituted or unsubstituted hydrocarbylsulfonyloxy leaving groups, for example, p-toluenesulfonyloxy, methanesulfonyloxy, and mesitylenesulfonyloxy, or halo leaving groups such as, for example, iodo, bromo, and chloro leaving groups, to give the compounds of Formula (3-4).

(Step 4)

The compounds of Formula (3-5) may be prepared by a standard alkylation reaction using compounds of Formula (3-4) and Formula (1-1) as shown in the Step 1 of Scheme 1. For example, reaction of a compound of Formula (1-1) with a base, such as, for example, NaH, in a suitable solvent, such as, for example, THF or DMF, at a suitable temperature, for example, at a temperature ranging from 0° C. to 20° C., followed by addition of a compound of Formula (3-4). The reaction mixture may be heated, for example, at a temperature ranging from 50° C. to 100° C., optionally in the presence of a catalytic amount of an iodide salt, such as, for example, KI.

(Step 5)

The compounds of Formula (3-6) may be prepared by reacting a compound of Formula (3-5) with a guanidine or guanidine carbonate in a suitable solvent, such as, for example, methanol or ethanol, at elevated temperature, for example, at a temperature ranging from 50° C. to 150° C. The compounds of Formula (3-6) may be isolated as a salt.

In one aspect of the present disclosure, there is provided at least one entity chosen from compounds of Formula (3-6) as defined in Scheme 3-1 and salts thereof.

(Step 6)

The protective group $Pg^5$ of the compounds of Formula (3-6) may be removed with an appropriate de-protecting agent. In the case where $Pg^5$ is a trialkylsilyl group, the compounds of Formula (3-6) may be reacted with acid, such as, for example, hydrogen chloride, in methanol at a temperature ranging from 0° C. to 40° C. to give the compounds of Formula (3-7).

(Step 7)

In the case where $Lg^1$ is a hydrocarbylsulfonyloxy leaving group, the compounds of Formula (3-8) may be prepared by reacting a compound of Formula (3-7) with hydrocarbylsulfonyl halide, such as, for example, 2-mesytylenesulfonyl chloride, in the presence of a base, such as, for example, trialkylamine, for example, diisopropylethylamine or triethylamine, in a suitable solvent such as, for example, THF, at a temperature ranging from 0° C. to 50° C.

In one aspect of the present disclosure there is provided at least one entity chosen from the compounds of Formula (3-8) as defined in Scheme 3-1 and salts thereof.

(Step 8)

In the case where $Lg^5$ is a hydrocarbylsulfonyloxy leaving group, the compounds of Formula (3-9) may be prepared by reacting a compound of Formula (3-8) with hydrocarbylsulfonyl halide, such as, for example, methanesulfonyl chloride, in a suitable solvent, such as, for example, THF, at ambient temperature, for example, at a temperature ranging from 10° C. to 40° C. The compounds of Formula (3-9) may also be prepared by reacting a compound of Formula (3-8) with a halogenating agent, such as, for example, lithium bromide or lithium chloride, in the presence of hydrocarbylsulfonyl bromide or chloride, in a suitable solvent such as, for example, THF, at ambient temperature, for example at a temperature ranging from 10° C. to 40° C.

In one aspect of the present disclosure, there is provided at least one entity chosen from compounds of Formula (3-9) as defined in Scheme 3-1 and salts thereof.

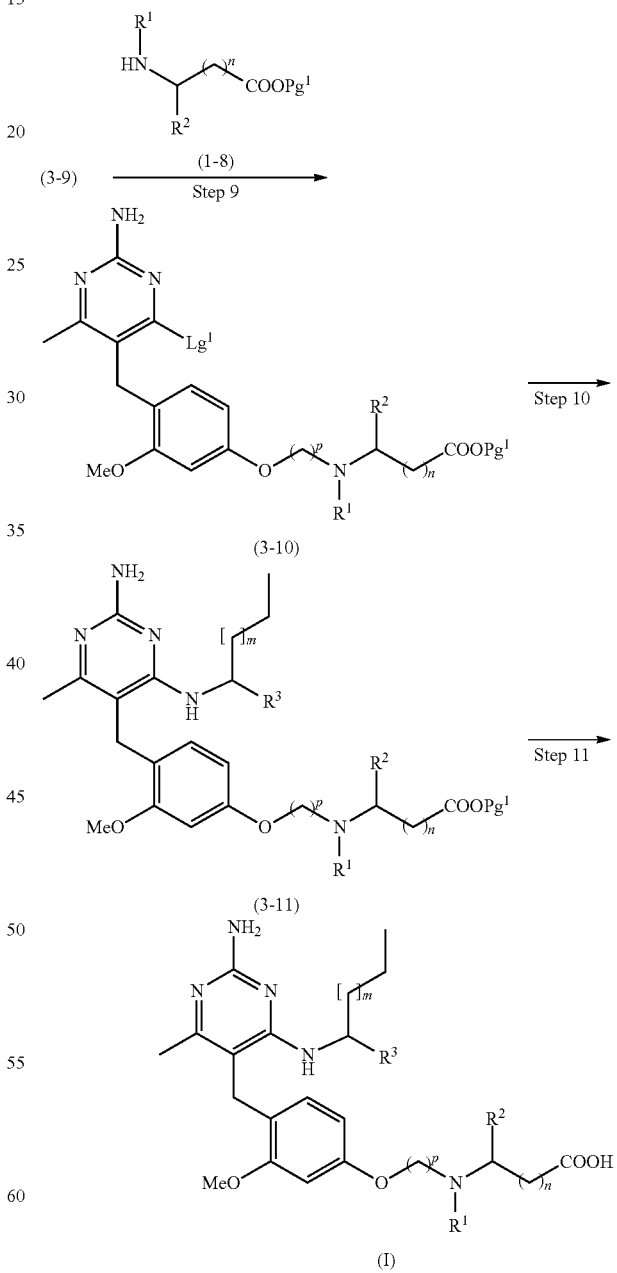

wherein m, n, $R^1$, $R^2$, and $R^3$ are as defined in Formula (I), p is 2 or 3, and the $Lg^1$ group may be independently chosen from conventional leaving groups which are well-known to the skilled person in the art, for example, substituted and unsubstituted hydrocarbylsulfonyloxy leaving groups, such as, for example, p-toluenesulfonyloxy, mesitylenesulfonyloxy, 2,4,6-triisopropylbenzenesulfonyloxy and methanesulfonyloxy groups, and halo leaving groups, such as, for example, iodo, bromo, and chloro leaving groups. The $Pg^1$ group is chosen from protective groups for a carboxylic acid group, for example, an ester such as, for example, a methyl ester, ethyl ester or tert-butyl ester.

(Step 9)

The compounds of Formula (3-10) may be prepared by reacting a compound of Formula (3-9) with a compound of Formula (1-8) in the presence of a base such as, for example, potassium bicarbonate or sodium bicarbonate, optionally with potassium iodide or sodium iodide, in a suitable solvent, such as, for example, acetonitrile, at a temperature ranging from 0° C. to 100° C.

In one aspect of the present disclosure there is provided at least one entity chosen from the compounds of Formula (3-10) as defined in Scheme 1 and salts thereof.

(Step 10)

The compounds of Formula (3-11) may be prepared reacting a compound of Formula (3-10) with an excess of the appropriate amine or amino alcohol, wherein the amino alcohol may optionally have its alcohol group protected, in a suitable solvent, such as, for example, propionitrile, butanol, or 1,4-dioxane, in the presence of trifluoroacetic acid at elevated temperature, for example, at a temperature ranging from 50° C. to 200° C., using conventional or microwave heating.

In one aspect there is provided a compound of Formula (3-11), as defined herein, and salts thereof.

(Step 11)

The compounds of Formula (I) may be prepared by removing a protective group of carboxylic acid moiety, in the presence of a base such as, for example, aqueous sodium hydroxide, at a temperature ranging from 0° C. to 40° C. In the case where $R^3$ is hydroxymethyl or hydroxyethyl and the hydroxy group is protected by a protective group, it may also be removed according to a method which is well-known by a skilled person in the art.

Alternatively, a compound of Formula (I) may be prepared by the sequence shown in Scheme 4:

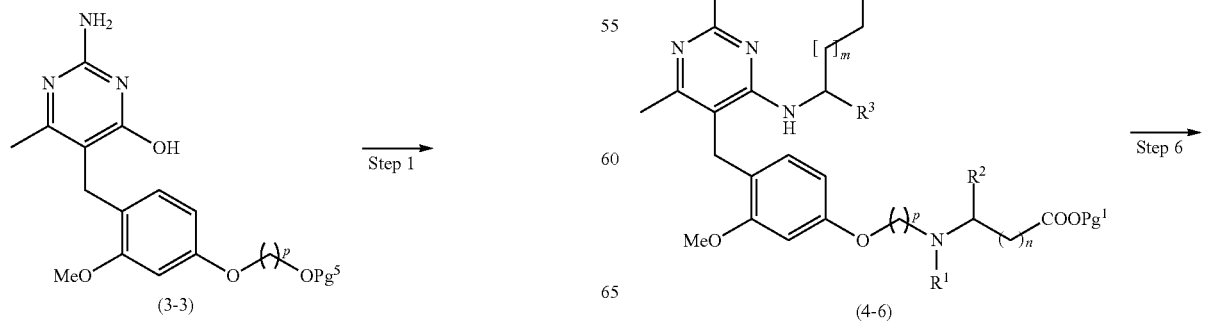

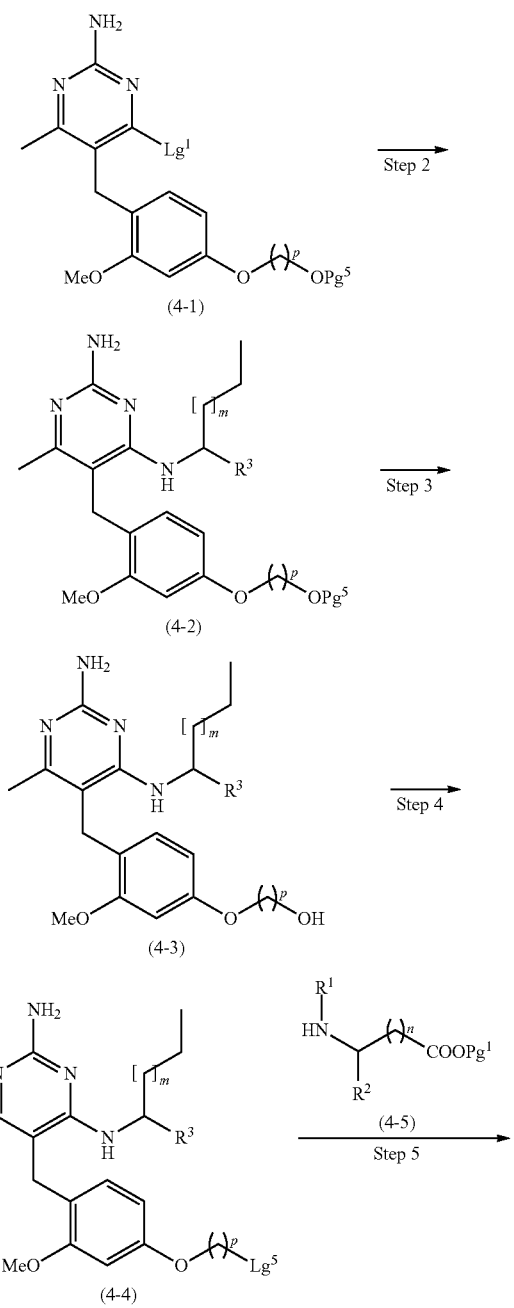

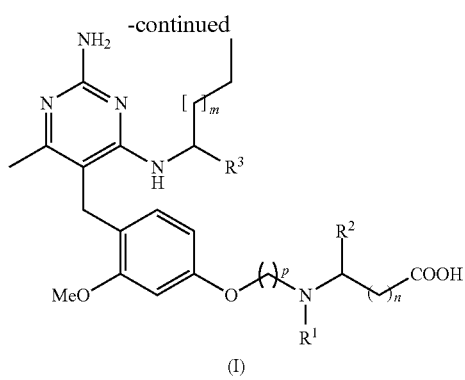

(I)

wherein m, n, $R^1$, $R^2$, and $R^3$ are as defined in Formula (I), p is 2 or 3, and the $Lg^1$ and $Lg^3$ groups may be independently chosen from conventional leaving groups which are well-known to the skilled person in the art, for example, substituted and unsubstituted hydrocarbylsulfonyloxy leaving groups, such as, for example, p-toluenesulfonyloxy, mesitylenesulfonyloxy, 2,4,6-triisopropylbenzenesulfonyloxy and methanesulfonyloxy groups, and halo leaving groups such as, for example, iodo, bromo, and chloro leaving groups. The $Pg^1$ group is chosen from protective groups for a carboxylic acid group, for example, an ester such as a methyl ester, ethyl ester or tert-butyl ester. The $Pg^5$ group is chosen from protective groups for a hydroxy group, for example, a trialkylsilyl group, such as, for example, t-butyldimethylsilyl.

(Step 1)

The compounds of Formula (4-1) may be prepared by the similar method as Step 7 of the Scheme 3-1.

In one aspect of the present disclosure, there is provided at least one entity chosen from compounds of Formula (4-1) as defined in Scheme 1 and salts thereof.

(Step 2)

The compounds of Formula (4-2) may be prepared by the similar method as Step 10 of the Scheme 3-2.

In one aspect of the present disclosure, there is provided at least one entity chosen from compounds of Formula (4-2) as defined in Scheme 1 and salts thereof.

(Step 3)

In the case where $R^3$ is hydroxymethyl or hydroxyethyl and the hydroxy group is not protected, the hydroxy group may be protected by reacting a compound of Formula (4-2) with an acetic anhydride or acetyl chloride in the presence of a base, such as, for example, trialkylamine, for example, diisopropylethylamine or triethylamine, and a catalytic amount of N,N-dimethyl-4-aminopyridine in a suitable solvent, such as, for example, THF, at a suitable temperature, for example, at a temperature ranging from 10° C. to 40° C., followed by deprotection of the protective group $Pg^5$ with an appropriate de-protecting agent. In the case where $Pg^5$ is a trialkylsilyl group, the intermediate may be reacted with tetrabutylammonium fluoride in THF at a temperature ranging from 0° C. to 40° C. to give the compounds of Formula (4-3).

Alternatively, in the case that $R^3$ does not contain a free hydroxy group, the compounds of Formula (4-3) may be prepared by a similar method to Step 6 of Scheme 3-1.

In one aspect of the present disclosure, there is provided at least one entity chosen from the compounds of Formula (4-3) as defined in Scheme 1 and salts thereof.

(Step 4)

The compounds of Formula (4-4) may be prepared by a similar method to Step 8 of Scheme 3-1.

In one aspect of the present disclosure, there is provided at least one entity chosen from the compounds of Formula (4-4) as defined in Scheme 1 and salts thereof.

(Step 5)

The compounds of Formula (4-6) may be prepared by a similar method to Step 9 of Scheme 3-2.

In one aspect of the present disclosure, there is provided at least one entity chosen from the compounds of Formula (4-6) as defined in Scheme 1 and salts thereof.

(Step 6)

The compounds of Formula (I) may be prepared by removing a protective group of carboxylic acid moiety, in the presence of a base such as, for example, aqueous sodium hydroxide, at a temperature ranging from 0° C. to 40° C. In the case where $R^3$ is hydroxymethyl or hydroxyethyl and the hydroxy group is protected by a protective group, it may also be removed according to a method which is well-known by a skilled person in the art.

In the case where the hydroxyl group in $R^3$ is protected, such protective group can be, for example, an alkyl ester group, silicon-based protecting group, or a benzyl-based protecting group.

In one embodiment, such hydroxy group in $R^3$ in Formula (1-10), Formula (2-5), Formula (2-6), Formula (2-7), Formula (3-11) or a compound of the formula:

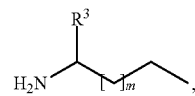

which is a starting material for these compounds may be protected by a silicon-based protective group or a benzyl-based protective group. The silicon-based protecting group may be a tri ($C_{1-4}$ alkyl) silyl group, for example, a trimethylsilyl group or a tert-butyldimethylsilyl group. In one embodiment, $R^3$ is tert-butyldimethylsilyl.

In one embodiment, such hydroxy group in $R^3$ may be protected by acetyl group which can be removed under the basic condition in the last step in each Scheme.

The compounds of Formula (1-8) may be commercially available or may be prepared by conventional methods known to a person skilled in the art. For example, when $R^2$ is hydrogen or $C_{1-4}$ alkyl, compounds of Formula (1-8) may be prepared according to Scheme 5-1:

Scheme 5-1

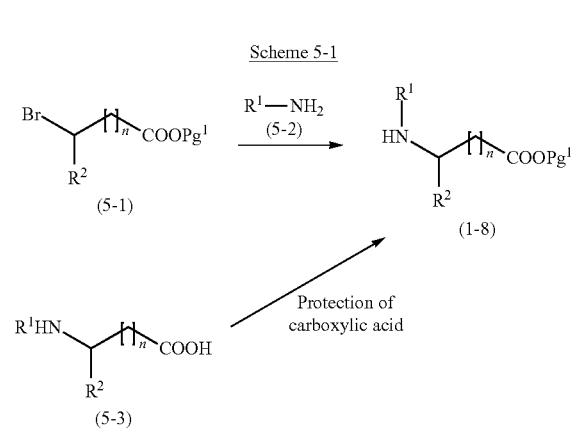

wherein n, $R^1$ and $R^2$ are as defined in Formula (I), and the $Pg^1$ group is chosen from protective groups for a carboxylic acid group, for example, an ester, such as a methyl ester, ethyl ester or tert-butyl ester.

The compounds of Formula (1-8) may be prepared by a reaction of a compound of Formula (5-1) with a compound of Formula (5-2) in the presence of a base, such as, for example, a trialkylamine, for example, triethylamine or diisopropylethylamine, in a suitable solvent, such as, for example, THF, acetonitrile, or dichloromethane, and at a suitable temperature, for example, at a temperature ranging from 10° C. to 40° C.

Alternatively, the compounds of Formula (1-8) may be prepared by protecting a carboxylic acid of Formula (5-3), which is commercially available or may be prepared by a conventional method known to the person skilled in the art. When n is 1, the compounds of Formula (1-8) may be prepared by an alkylation reaction as in the Scheme 5-2 below.

Scheme 5-2

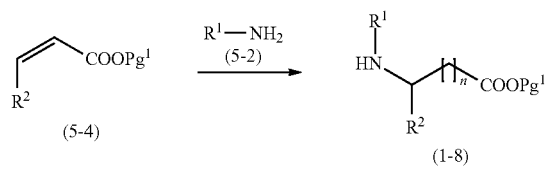

wherein $R^1$ and $R^2$ are as defined in Formula (I), and the $Pg^1$ group is chosen from protective groups for a carboxylic acid group, for example, esters such as methyl ester, ethyl ester or tert-butyl ester.

A compound of Formula (5-4) may be reacted with a compound of Formula (5-2) in a suitable solvent such as alcohol, for example, ethanol, to give a compound of Formula (1-8).

Alternatively, a compound of Formula (I) may be prepared by the sequence shown in Scheme 6:

Scheme 6

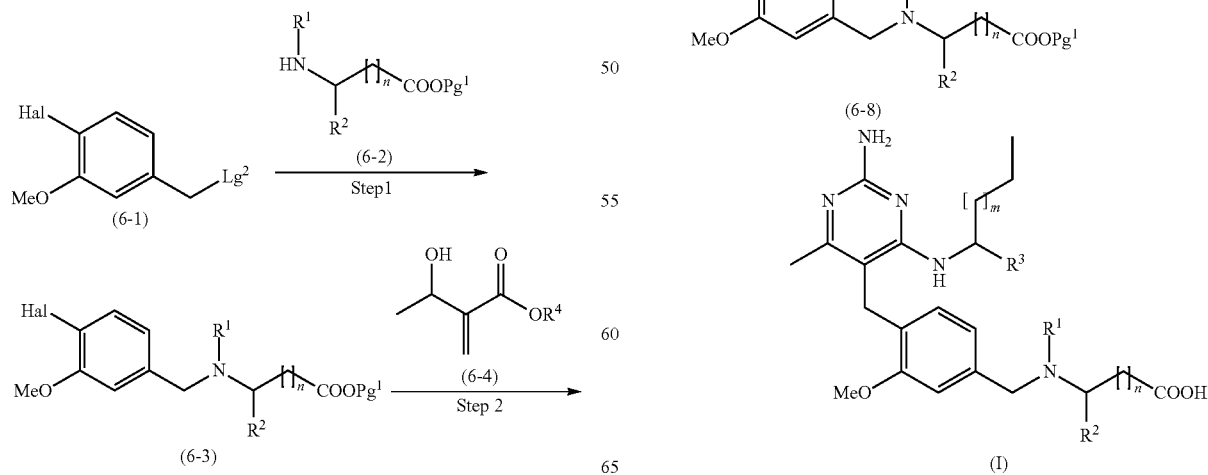

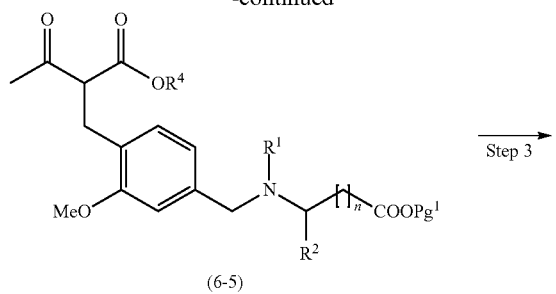

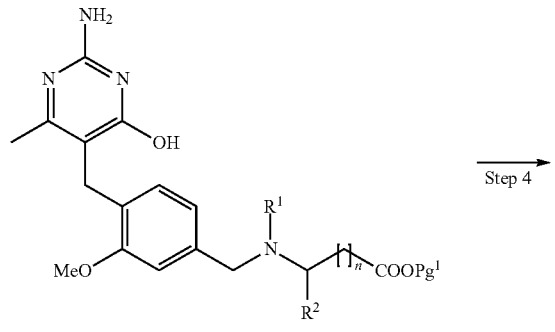

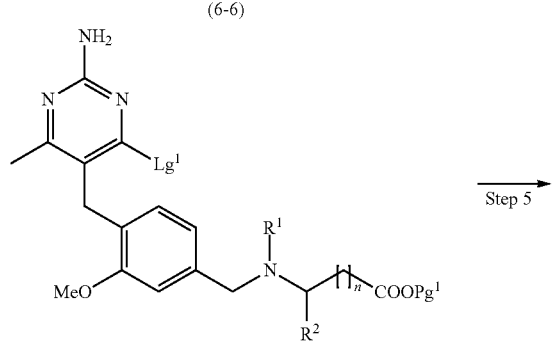

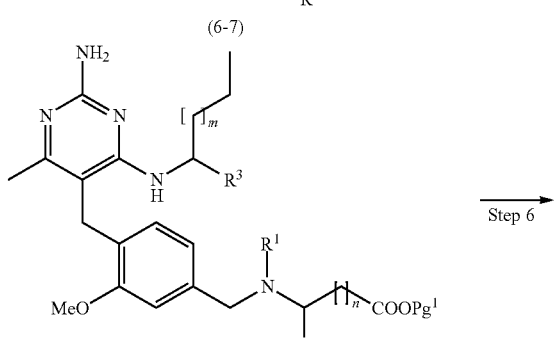

wherein m, n, $R^1$, $R^2$ and $R^3$ are as defined in Formula (I), $R^4$ is chosen from $C_{1-4}$ alkyl groups, the $Lg^1$ and $Lg^2$ groups may be independently chosen from conventional leaving groups which are well-known to the skilled person in the art, for example, substituted and unsubstituted hydrocarbylsulfonyloxy leaving groups such as p-toluenesulfonyloxy, mesitylenesulfonyloxy, 2,4,6-triisopropylbenzenesulfonyloxy and methanesulfonyloxy groups, and halogen atoms such as iodo, bromo or chloro. The $Pg^1$ group is chosen from protective groups for a carboxylic acid group, for example, an ester such as a methyl ester, ethyl ester or tert-butyl ester. The Hal is bromine or iodine.

(Step 1)

The compound of Formula (6-3) may be prepared by standard N-alkylation reaction using a compound of Formula (6-1) with a compound of Formula (6-2) in the presence of a base such as potassium bicarbonate, sodium bicarbonate, sodium carbonate, potassium carbonate, triethylamine or N,N-diisopropylethylamine optionally with potassium iodide or sodium iodide, in a suitable solvent such as acetonitrile, dimethylformamide and dimethylacetamide at a temperature, for example, ranging from 0° C. to 100° C.

In one embodiment of the present disclosure, there is provided at least one entity chosen from compound of Formula (6-3) as defined in Scheme 6 and salts thereof.

(Step 2)

The compound of Formula (6-5) may be prepared by a Heck reaction between a compound of Formula (6-3) and a compound of Formula (6-4). The reaction may be carried out using a palladium catalyst, such as $Pd(OAc)_2$ or 1,1'-bis(di-tert-butylphosphino)ferrocene palladium dichloride, a base such as potassium bicarbonate, sodium bicarbonate, sodium carbonate, potassium carbonate or dicyclohexylmethylamine, and an ammonium salt such as tetrabutylammoniun chloride or tetrabutylammoniun bromide. The reaction may be performed in a suitable solvent such as tetrahydrofuran or dimethylacetamide at a temperature, for example, ranging from 50° C. to 150° C.

In one aspect of the present disclosure, there is provided at least one entity chosen from compounds of Formula (6-3) as defined in Scheme 6 and salts thereof.

(Step 3)

The Compound of Formula (6-6) may be prepared by a similar method to Step 2 of Scheme 1.

(Step 4)

The Compound of Formula (6-7) may be prepared by a similar method to Step 4 of Scheme 1.

(Step 5)

The Compound of Formula (6-8) may be prepared by a similar method to Step 7 of Scheme 1.

(Step 6)

The Compound of Formula (I) may be prepared by a similar method to Step 8 of scheme 1. In the case that $R^3$ is hydroxymethyl or hydroxyethyl and the hydroxy group is protected by a protective group, it may also be removed according to a method which is well-known by a skilled person in the art.

It will be appreciated that, in some of the reactions mentioned herein, it may be necessary or desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, $3^{rd}$ edition, John Wiley and Sons, 1999). Thus, if reactants include groups such as amino, carboxy or hydroxy, it may be desirable to protect the group in some of the reactions mentioned herein.

The compounds described herein may be useful intermediates for the preparation of compounds of Formula (I) and may be isolated as a free base/acid or as a salt. Therefore, in certain aspects and embodiments of the present disclosure, there is provided an intermediate described herein, or a salt thereof, wherein any of the variable groups described for said intermediate may take any of the values described herein in connection with that group.

Non-limiting examples of suitable pharmaceutically acceptable salts of a compound of the Formula (I) include acid-addition salts of a compound of the Formula (I), for example, acid-addition salts with an inorganic or organic acid such as, for example, hydrochloric acid, hydrobromic acid, sulphuric acid, trifluoroacetic acid, citric acid, maleic acid, asparagine, or glutamine. Non-limiting examples of suitable pharmaceutically acceptable salts of a compound of the Formula (I) also include base-addition salts of a compound of the Formula (I), for example, base-addition salts with an inorganic or organic base such as, for example, a sodium salt, potassium salt, methylamine, or 2-aminoethanol.

The at least one entity chosen from compounds of the Formula (I) and pharmaceutically acceptable salts thereof of the present disclosure may be administered in the form of a Pro-drug, i.e. a compound that is broken down in the human or animal body to release a compound or salt of the present disclosure. A Pro-drug may be used to alter the physical properties and/or the pharmacokinetic properties of at least one entity of the present disclosure. A Pro-drug can be formed when the at least one entity of the present disclosure contains at least one suitable group and/or substituent to which at least one property-modifying group can be attached. Non-limiting examples of Pro-drugs include in-vivo-cleavable amide derivatives which may, for example, be formed at at least one amino group in the at least one entity chosen from compounds of the Formula (I) and pharmaceutically acceptable salts thereof.

Accordingly, the present disclosure includes those compounds of the Formula (I) as defined hereinbefore and pharmaceutically acceptable salts thereof when made available by organic synthesis and when made available within the human or animal body by way of cleavage of a Pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A non-limiting example of a suitable pharmaceutically acceptable Pro-drug of a compound of the Formula (I) is one that is based on reasonable medical judgement as being suitable for administration to the human or animal body without undesirable pharmacological activities and without undue toxicity.

Various forms of Pro-drug have been described, for example, in the following documents:
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, Advanced Drug Delivery Reviews, 8, 1-38 (1992);

e) H. Bundgaard, et al., Journal of Pharmaceutical Sciences, 77, 285 (1988);

f) N. Kakeya, et al., Chem. Pharm. Bull., 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A non-limiting example of a suitable pharmaceutically acceptable pro-drug of a compound of the Formula (I) that possesses an amino group is an in-vivo cleavable amide derivative thereof. Non-limiting examples of suitable pharmaceutically-acceptable amides from an amino group include an amide formed with a $C_{1-10}$ alkanoyl group, such as, for example, an acetyl group, a benzoyl group, a phenylacetyl group, a substituted benzoyl group, and a substituted phenylacetyl group. Non-limiting examples of ring substituents on the phenylacetyl and benzoyl groups include aminomethyl, N alkylaminomethyl, N,N-dialkylaminomethyl, morpholinomethyl, piperazin-1-ylmethyl, and 4-($C_{1-4}$ alkyl)piperazin-1-ylmethyl.

The in-vivo effects of a compound of the Formula (I) may be exerted in part by one or more metabolites that are formed within the human or animal body after administration of a compound of the Formula (I). As stated hereinbefore, the in-vivo effects of a compound of the Formula (I) may also be exerted by way of metabolism of a precursor compound (a pro-drug).

According to an embodiment of the present disclosure, there is provided a pharmaceutical composition which comprises at least one entity chosen from compounds of the Formula (I) and pharmaceutically acceptable salts thereof, as defined hereinbefore, in association with at least one pharmaceutically acceptable diluent or carrier. The pharmaceutical composition may be used in the treatment of cancer. The composition may be in a form suitable for oral administration, for example, as a tablet or capsule; for parenteral injection (including intravenous, subcutaneous, intramuscular, intravascular, or infusion) as a sterile solution, suspension, or emulsion; for topical administration, for example, as an ointment or cream; or for rectal administration, for example, as a suppository.

The at least one entity chosen from compounds of Formula (I) and pharmaceutically acceptable salts thereof could also be administered as an air spray for inhalation. The air spray (e.g., spray, aerosol, dry powder preparation, etc.) could be optionally formulated as an aqueous solution or suspension, or as an aerosol delivered from a pressurized pack such as a pressurized metered dose inhaler by using, for example, a liquefied propellant. A dry powder preparation may also be used. An aerosol appropriate for inhalation may be either a suspension or solution, and would typically contain the at least one entity chosen from compounds of Formula (I) and pharmaceutically acceptable salts thereof and any appropriate propellant(s) such as, for example a fluorocarbon- or hydrogen-containing chlorofluorocarbon or a mixture thereof. For instance, it may contain hydrofluoroalkane such as 1,1,1,2-tetrafluoroethane, heptafluoroalkane (HFA) such as 1,1,1,2,3,3,3-heptafluoro-n-propane, or a mixture thereof. An aerosol may optionally contain an additional preparation excipient well-known to those skilled in the art such as surfactant (e.g., oleic acid or lecithin) and cosolvent (e.g., ethanol), etc. For example, an aerosol preparation could be delivered using the inhaler known as "TURBUHALER™".

For oral administration, the at least one entity chosen from compounds of the Formula (I) and pharmaceutically acceptable salts thereof of the present disclosure may be admixed with at least one adjuvant and/or carrier, for example, chosen from lactose, saccharose, sorbitol, mannitol; starches, for example, potato starch, corn starch, or amylopectin; cellulose derivatives; binders, for example, gelatine or polyvinylpyrrolidone; and/or lubricants, for example, magnesium stearate, calcium stearate, polyethylene glycols, waxes, paraffins, and the like, and then compressed into tablets. If coated tablets are desired, the cores, prepared as described above, may be coated with a concentrated sugar solution which may contain, for example, gum arabic, gelatine, talcum, and titanium dioxide. Alternatively, the tablet may be coated with a suitable polymer dissolved in a readily volatile organic solvent.

For the preparation of soft gelatine capsules, the at least one entity chosen from compounds of the Formula (I) and pharmaceutically acceptable salts thereof of the present disclosure may be admixed with, for example, a vegetable oil or polyethylene glycol. Hard gelatine capsules may contain granules of the at least one entity using either the above-mentioned excipients for tablets. Also liquid or semisolid formulations of the at least one entity of the present disclosure may be filled into hard gelatine capsules. Liquid preparations for oral application may be in the form of syrups or suspensions, for example, solutions containing the at least one entity of the present disclosure, the balance being sugar and a mixture of ethanol, water, glycerol, and propylene glycol. Optionally such liquid preparations may contain colouring agents, flavouring agents, saccharine, carboxymethylcellulose as a thickening agent, and/or other excipients known to those skilled in art.

The at least one entity chosen from compounds of the Formula (I) and pharmaceutically acceptable salts thereof may be administered to a subject such as a warm blooded animal at a unit dose ranging from 5 mg/m$^2$ to 5000 mg/m$^2$ body area of the animal, i.e. approximately ranging from 0.1 mg/m$^2$ to 100 mg/kg, and this may provide a therapeutically effective dose. Doses are reported on the basis of the weight of the compound of Formula (I). A unit dose form such as a tablet or capsule will usually contain, for example, ranging from 1 mg to 250 mg of active ingredient, e.g., compound of Formula (I). For example, a daily dose in the range of from 1 mg/kg to 50 mg/kg may be employed. However the daily dose will necessarily be varied depending upon the host treated, the particular route of administration, and the severity of the illness being treated. Accordingly the optimum dosage may be determined by the practitioner who is treating any particular patient.

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In the context of the present specification, the term "therapy" also includes "prophylaxis" unless there are specific indications to the contrary. The terms "therapeutic" and "therapeutically" should be construed accordingly.

As used herein, the term "treatment" is intended to have its normal everyday meaning of dealing with a disease in order to entirely or partially relieve one, some or all of its symptoms, or to correct or compensate for the underlying pathology.

As used herein, the term "prophylaxis" is intended to have its normal everyday meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The at least one entity chosen from compounds of the Formula (I) and pharmaceutically acceptable salts thereof of the present disclosure may be effective activators of TLR7 in vitro. Accordingly, the at least one entity of the present disclosure may be expected to be potentially useful agents in the treatment or prophylaxis of diseases or medical conditions mediated alone or in part by TLR7. For example, the following non-limiting diseases and conditions listed in paragraphs 1 to 8 below may be treatable with compounds of the present disclosure.

1. respiratory tract: obstructive diseases of the airways including: asthma, including bronchial, allergic, intrinsic, extrinsic, exercise-induced, drug-induced (including aspirin and NSAID-induced), and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating antineoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of cancers including bladder, head and neck, prostate, breast, lung, ovarian, pancreatic, bowel and colon, colorectal, stomach, skin, kidney, renal, esophageal, liver, uterus, bone thyroid, cerebral, bile duct and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *Mycobacterium avium*, leprosy; other infectious diseases, such as fungal diseases, *chlamydia, candida, aspergillus, cryptococcal meningitis, pneumocystis carnii*, cryptosporidiosis, histoplasmosis, toxoplasmosis, trypanosome infection, and leishmaniasis.

It is envisaged that for the methods of treatment or prophylaxis mentioned herein, the at least one entity chosen from compounds of Formula (I) and pharmaceutically acceptable salts thereof will be administered to a mammal, such as a human being. Similarly, for the uses of at least one entity chosen from compounds of Formula (I) and pharmaceutically acceptable salts thereof for the treatment or prophylaxis of diseases or medical conditions mentioned herein, it is envisaged that the at least one entity will be administered to a mammal, such as a human being.

According to an another aspect of the present disclosure, there is therefore provided at least one entity chosen from compounds of Formula (I) and pharmaceutically acceptable salts thereof for use as a medicament.

According to a further aspect of the present disclosure, there is provided at least one entity chosen from compounds of Formula (I) and pharmaceutically acceptable salts thereof for use in the treatment or prophylaxis of a disease mediated through TLR7. In one embodiment of the present disclosure, said disease mediated through TLR7 is cancer. The compound of Formula (I), or a pharmaceutically acceptable salt thereof, is also expected to be of use in the treatment or prophylaxis of metastasis, tumour recurrence and paraneoplastic syndrome.

In a further embodiment of the present disclosure, said cancer is chosen from bladder cancer, head and neck cancer, prostate cancer, breast cancer, lung cancer, uterus cancer, pancreatic cancer, liver cancer, renal cancer, ovarian cancer, colon cancer, stomach cancer, skin cancer, bone cancer, thyroid cancer, bile duct cancer, cerebral tumor, malignant myeloma, and lymphoproliferative tumors. In one embodiment of the present disclosure, said disease mediated through TLR7 is asthma, COPD, allergic rhinitis, allergic conjunctivitis, atopic dermatitis, hepatitis B, hepatitis C, HIV, HPV, bacterial infections, or dermatosis.

According to a further aspect of the present disclosure, there is provided the use of at least one entity chosen from compounds of Formula (I) and pharmaceutically acceptable salts thereof for the preparation of a medicament for the treatment or prophylaxis of a disease mediated through TLR7. In one embodiment of the present disclosure, said disease mediated through TLR7 is cancer. In a further embodiment of the present disclosure, said cancer is chosen from bladder cancer, head and neck cancer, prostate cancer, breast cancer, lung cancer, uterus cancer, pancreatic cancer, liver cancer, renal cancer, ovarian cancer, colon cancer, stomach cancer, skin cancer, bone cancer, thyroid cancer, bile duct cancer, cerebral tumor, malignant myeloma, and lymphoproliferative tumors. In one embodiment of the present disclosure, said disease mediated through TLR7 is asthma, COPD, allergic rhinitis, allergic conjunctivitis, atopic dermatitis, hepatitis B, hepatitis C, HIV, HPV, bacterial infections, or dermatosis.

According to a further aspect of the present disclosure, there is provided the use of at least one entity chosen from compounds of Formula (I) and pharmaceutically acceptable salts thereof for the preparation of a medicament for the treatment or prophylaxis of cancer. In one embodiment of the present disclosure, said cancer is chosen from bladder cancer, head and neck cancer, prostate cancer, breast cancer, lung cancer, uterus cancer, pancreatic cancer, liver cancer, renal cancer, ovarian cancer, colon cancer, stomach cancer, skin cancer, cerebral tumor, malignant myeloma, and lymphoproliferative tumors.

According to a further aspect of the present disclosure, there is provided the use of at least one entity chosen from compounds of Formula (I) and pharmaceutically acceptable salts thereof for the preparation of a medicament for the treatment or prophylaxis of asthma, COPD, allergic rhinitis, allergic conjunctivitis, atopic dermatitis, hepatitis B, hepatitis C, HIV, HPV, bacterial infections, or dermatosis.

In one aspect of the present disclosure there is provided at least one entity chosen from compounds of Formula (I) and pharmaceutically acceptable salts thereof for use in the treatment of cancer.

According to a further aspect of the present disclosure, there is provided a method of using at least one entity chosen from compounds of Formula (I) and pharmaceutically acceptable salts thereof for the treatment or prophylaxis of cancer. Accordingly there is therefore provided a method of treating or prophylaxis cancer in a subject such as a warm-blooded animal, further such as a human, in need of such treatment or prophylaxis, which comprises administering to said subject a therapeutically effective amount of at least one entity chosen from compounds of Formula (I) and pharmaceutically acceptable salts thereof as defined herein. In one embodiment of the present disclosure, said cancer is chosen from bladder cancer, head and neck cancer, prostate cancer, breast cancer, lung cancer, uterus cancer, pancreatic cancer, liver cancer, renal cancer, ovarian cancer, colon cancer, stomach cancer, skin cancer, bone cancer, thyroid cancer, bile duct cancer, cerebral tumor, malignant myeloma, and lymphoproliferative tumors.

According to a further aspect of the present disclosure, there is provided a method of using at least one entity chosen from compounds of Formula (I) and pharmaceutically acceptable salts thereof for the treatment or prophylaxis of asthma, COPD, allergic rhinitis, allergic conjunctivitis, atopic dermatitis, hepatitis B, hepatitis C, HIV, HPV, bacterial infections, or dermatosis.

According to a further aspect of the present disclosure, there is provided a method of treating or prophylaxis a human suffering from a disease in which activation of TLR7 is beneficial, comprising the steps of administering to a person in need thereof of a therapeutically effective amount of at least one entity chosen from compounds of Formula (I) and pharmaceutically acceptable salts thereof. In one embodiment of the present disclosure, the disease in which activation of TLR7 is beneficial is cancer. In a further embodiment of the present disclosure, said cancer is chosen from bladder cancer, head and neck cancer, prostate cancer, breast cancer, lung cancer, uterus cancer, pancreatic cancer, liver cancer, renal cancer, ovarian cancer, colon cancer, stomach cancer, skin cancer, bone cancer, thyroid cancer, bile duct cancer, cerebral tumor, malignant myeloma, and lymphoproliferative tumors. In one embodiment of the present disclosure, the disease in which activation of TLR7 is beneficial is asthma, COPD, allergic rhinitis, allergic conjunctivitis, atopic dermatitis, hepatitis B, hepatitis C, HIV, HPV, bacterial infections, or dermatosis.

In any aspect or embodiment described herein, the cancer may be bladder cancer.

In any aspect or embodiment described herein, the cancer may be head and neck cancer.

In any aspect or embodiment described herein, the cancer may be prostate cancer.

In any aspect or embodiment described herein, the cancer may be breast cancer.

In any aspect or embodiment described herein, the cancer may be lung cancer.

In any aspect or embodiment described herein, the cancer may be uterus cancer.

In any aspect or embodiment described herein, the cancer may be pancreatic cancer.

In any aspect or embodiment described herein, the cancer may be liver cancer.

In any aspect or embodiment described herein, the cancer may be renal cancer.

In any aspect or embodiment described herein, the cancer may be ovarian cancer.

In any aspect or embodiment described herein, the cancer may be colon cancer.

In any aspect or embodiment described herein, the cancer may be stomach cancer.

In any aspect or embodiment described herein, the cancer may be skin cancer.

In any aspect or embodiment described herein, the cancer may be bone cancer.

In any aspect or embodiment described herein, the cancer may be thyroid cancer.

In any aspect or embodiment described herein, the cancer may be bile duct cancer.

In any aspect or embodiment described herein, the cancer may be cerebral tumor.

In any aspect or embodiment described herein, the cancer may be malignant myeloma cancer.

In any aspect or embodiment described herein, the cancer may be lymphoproliferative tumors.

The anticancer treatment or prophylaxis defined herein may be applied as a sole therapy or may involve, in addition to the compounds of the present disclosure, conventional surgery or radiotherapy or chemotherapy.

Such conventional surgery could be applied before or after treatment with the compound of invention.

Such radiotherapy could be administered concurrently, simultaneously, sequentially or separately to treatment with the compound of the invention and may include one or more of the external-beam radiation therapy, internal radiation therapy or systemic radiation therapy using a radioactive substance such as a radio-labelled monoclonal antibody.

In a further aspect of the invention there is provided a combination comprising a compound of Formula (I), or a pharmaceutically acceptable salt thereof and radiotherapy, for use in the treatment of cancer.

In a further aspect of the invention, there is provided a method of treating cancer in a warm blooded animal, such as man, in need of such treatment, which comprises administering to said animal an effective amount of a compound of Formula (I), or a pharmaceutically acceptable salt thereof, in combination with an effective amount of radiotherapy.

Such chemotherapy could be administered concurrently, simultaneously, sequentially or separately to treatment with the compound of the invention and may include one or more of the following non-limiting categories of anti-tumour agents: (i) other antiproliferative/antineoplastic drugs and combinations thereof, as used in medical oncology, such as alkylating agents (for example cis platin, oxaliplatin, carboplatin, miriplatin, cyclophosphamide, nitrogen mustard, melphalan, chlorambucil, busulphan, bendamustine temozolamide and nitrosoureas); antimetabolites (for example gemcitabine and antifolates such as fluoropyrimidines like 5 fluorouracil and tegafur, raltitrexed, methotrexate, cytosine arabinoside, hydroxyurea and purine analogues such as fludarabine); antitumour antibiotics (for example anthracyclines like adriamycin, bleomycin, doxorubicin, daunomycin, epirubicin, amrubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin); (ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), the androgen receptor antagonists MDV3100 or ARN-509 which prevent nuclear translocation of the androgen receptor and its binding to either DNA or coactivator proteins, inhibitors of CYP17A1 such as abiraterone (ZYTIGA™), and mixed inhibitors of androgen receptor function and CYP17A1 such as TOK-001 (galeterone), LHRH antagonists or LHRH agonists (for example goserelin, leuprorelin and buserelin), progestogens (for example megestrol acetate), aromatase inhibitors (for example as anastrozole, letrozole, vorazole and exemestane), and inhibitors of 5α-reductase such as finasteride; (iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function, or antibodies to Heparanase;

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example, inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774), and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777), BRAF inhibitor (Vemurafenib) and lonafarnib (SCH66336)), inhibitors of cell signalling through MEK (e.g. Selumetinib) and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459), and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (AVASTIN™) and for example, a VEGF receptor tyrosine kinase inhibitor such as vandetanib (ZD6474), vatalanib (PTK787), sunitinib (SU11248), axitinib (AG-013736), pazopanib (GW 786034), and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856, and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434, and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including, for example, approaches to inhibit immune checkpoint such as anti-CTLA4 antibody ipilimumab (Yervoy™), anti-CTLA4 antibody (MEDI-1123), anti-PD1 antibody (BMS-936558, or MK3475), or anti-PDL1 antibody (BMS-936559), approaches to stimulate immune response such as anti-CD40 antibody (HCD-122), anti-OX-40 antibody, or anti-4-1BB antibody (BMS-663513 or PF-05082566), approaches to induce apoptosis such as anti-TRAIL antibody (AMG-951), anti-TRAIL-R1 antibody (HGS-ETR1), or anti-TRAIL-R2 antibody (AMG-655), ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies, approaches to decrease the function of immune suppressive cells such as regulatory T cells, myeloid-derived suppressor cells or IDO (indoleamine 2,3,-deoxygenase)-expressing dendritic cells, and approaches using cancer vaccines consisting of proteins or peptides derived from tumour-associated antigens such as NY-ESO-1, MAGE-3, WT1, or Her2/neu.

According to another aspect of the present disclosure, there is provided a pharmaceutical product comprising at least one entity chosen from compounds of Formula (I) and pharmaceutically acceptable salts thereof as defined herein and at least one additional anti-tumour substance as defined herein for the conjoint treatment of cancer.

According to this aspect of the present disclosure, there is provided a pharmaceutical product comprising at least one entity chosen from compounds of Formula (I) and pharmaceutically acceptable salts thereof as defined herein, and at least one additional anti-tumour substance as defined herein for the conjoint treatment of cancer.

According to this aspect of the present disclosure, there is provided a pharmaceutical product comprising at least one entity chosen from compounds of Formula (I) and pharmaceutically acceptable salts thereof as defined herein, and at least one additional anti-tumour substance for the conjoint treatment of cancer.

According to this aspect of the present disclosure, there is provided a combination suitable for use in the treatment of cancer comprising at least one entity chosen from compounds of Formula (I) and pharmaceutically acceptable salts thereof and at least one anti-tumour agents chosen from the anti-tumour agents listed under (i)-(ix) above.

According to this aspect of the invention there is provided a combination suitable for use in the treatment of cancer comprising a compound of Formula (I) as defined hereinbefore, or a pharmaceutically acceptable salt thereof, and any one of the anti-tumour agents listed under (i)-(x) above.

Therefore in a further aspect of the present disclosure, there is provided at least one entity chosen from compounds of Formula (I) and pharmaceutically acceptable salts thereof in combination with at least one anti-tumour agent chosen from those listed under (i)-(ix) herein above.

Therefore in a further aspect of the invention there is provided a compound of Formula (I), or a pharmaceutically acceptable salt thereof, in combination with an anti-tumour agent selected from one listed under (i)-(x) herein above.

In one embodiment there is provided a combination comprising a compound of Formula (I), or a pharmaceutically acceptable salt thereof and gemcitabine, for use in the treatment of cancer.

In one embodiment there is provided a combination comprising a compound of Formula (I), or a pharmaceutically acceptable salt thereof and an anti-CTLA4 antibody (such as Yervoy™ or MEDI-1123), for use in the treatment of cancer.

In one embodiment there is provided a combination comprising a compound of Formula (I), or a pharmaceutically acceptable salt thereof and an anti-PDL1 antibody (such as BMS-936559), for use in the treatment of cancer.

Herein, where the term "combination" is used, it is to be understood that this refers to simultaneous, separate, or sequential administration. In one embodiment, "combination" refers to simultaneous administration. In another embodiment, "combination" refers to separate administration.

In a further embodiment, "combination" refers to sequential administration. Where the administration is sequential or separate, the delay in administering the second component should not be such as to lose the beneficial effect of the combination.

According to a further aspect of the present disclosure, there is provided a pharmaceutical composition which comprises at least one entity chosen from compounds of Formula (I) and pharmaceutically acceptable salts thereof in combination with an anti-tumour agent chosen from those listed under (i)-(ix) herein above, in association with at least one pharmaceutically acceptable diluent or carrier.

According to a further aspect of the invention there is provided a pharmaceutical composition which comprises a compound of Formula (I), or a pharmaceutically acceptable salt thereof, in combination with an anti-tumour agent selected from one listed under (i)-(x) herein above, in association with a pharmaceutically acceptable diluent or carrier.

According to a further aspect of the present disclosure, there is provided a pharmaceutical composition which comprises at least one entity chosen from compounds of Formula (I) and pharmaceutically acceptable salts thereof in combination with at least one anti-tumour agent chosen from those listed under (i)-(ix) herein above, in association with at least one pharmaceutically acceptable diluent or carrier for use in the treatment of cancer.

According to a further aspect of the invention there is provided a pharmaceutical composition which comprises a compound of Formula (I), or a pharmaceutically acceptable salt thereof, in combination with an anti-tumour agent selected from one listed under (i)-(x) herein above, in association with a pharmaceutically acceptable diluent or carrier for use in the treatment of cancer.

According to another feature of the present disclosure, there is provided the use of at least one entity chosen from compounds of Formula (I) and pharmaceutically acceptable salts thereof, in combination with at least one anti-tumour agent chosen from those listed under (i)-(ix) herein above, in the manufacture of a medicament for use in cancer in a warm blooded animal, such as human.

According to a further aspect of the invention there is provided a pharmaceutical composition which comprises a compound of Formula (I), or a pharmaceutically acceptable salt thereof, in combination with an anti-tumour agent selected from one listed under (i)-(x) herein above, in association with a pharmaceutically acceptable diluent or carrier for use in the treatment of cancer.

According to another feature of the present disclosure, there is provided at least one entity chosen from compounds of Formula (I) and pharmaceutically acceptable salts thereof, in combination with at least one anti-tumour agent chosen from those listed under (i)-(ix) herein above for use in the treatment of cancer in a warm blooded animal, such as human.

According to another feature of the invention there is provided a compound of the Formula (I), or a pharmaceutically acceptable salt thereof, in combination with an anti-tumour agent selected from one listed under (i)-(x) herein above for use in the treatment of cancer in a warm blooded animal, such as man.

Therefore in an additional feature of the present disclosure, there is provided a method of treating cancer in a warm blooded animal, such as human, in need of such treatment which comprises administering to said animal a therapeutically effective amount of at least one entity chosen from compounds of Formula (I) and pharmaceutically acceptable salts thereof, in combination with at least one anti-tumour agent chosen from those listed under (i)-(ix) herein above.

Therefore in an additional feature of the invention, there is provided a method of treating cancer in a warm blooded animal, such as man, in need of such treatment which comprises administering to said animal an effective amount of a compound of Formula (I), or a pharmaceutically acceptable salt thereof, in combination with an anti-tumour agent selected from one listed under (i)-(x) herein above.

According to a further aspect of the present disclosure, there is provided a kit comprising at least one entity chosen from compounds of Formula (I) and pharmaceutically acceptable salts thereof, in combination with at least one anti-tumour agent chosen from those listed under (i)-(ix) herein above.

According to a further aspect of the present invention there is provided a kit comprising a compound of Formula (I), or a pharmaceutically acceptable salt thereof, in combination with an anti-tumour agent selected from one listed under (i)-(x) herein above.

According to a further aspect of the present disclosure, there is provided a kit comprising:
a) at least one entity chosen from compounds of Formula (I) and pharmaceutically acceptable salts thereof, in a first unit dosage form;
b) at least one anti-tumour agent chosen from the anti-tumour agents listed under (i)-(ix) herein above, in a second unit dosage form; and
c) container means for containing at least said first and second dosage forms.

According to a further aspect of the present disclosure, there is provided a kit comprising at least one entity chosen from compounds of Formula (I) and pharmaceutically acceptable salts thereof, in combination with at least one additional anti-tumour agent.

According to a further aspect of the present invention there is provided a kit comprising:
a) a compound of Formula (I), or a pharmaceutically acceptable salt thereof, in a first unit dosage form;
b) an anti-tumour agent selected from one listed under (i)-(x) herein above; in a second unit dosage form; and
c) container means for containing said first and second dosage forms.

According to a further aspect of the present invention there is provided a kit comprising a compound of Formula (I), or a pharmaceutically acceptable salt thereof, in combination with an additional anti-tumour agent.

According to a further aspect of the present disclosure, there is provided a kit comprising:
a) at least one entity chosen from compounds of Formula (I) and pharmaceutically acceptable salts thereof, in a first unit dosage form;
b) at least one second anti-tumour agent in a second unit dosage form; and
c) container means for containing said first and second dosage forms.

In one aspect of the present disclosure, the at least one entity chosen from compounds of Formula (I) and pharmaceutically acceptable salts thereof may be useful as vaccine adjuvants.

As a further aspect of the present disclosure, there is provided at least one entity chosen from compounds of Formula (I) and pharmaceutically acceptable salts thereof, as defined herein, for use as a vaccine adjuvant.

As a further aspect of the present disclosure, there is provided the use of at least one entity chosen from compounds of Formula (I) and pharmaceutically acceptable salts thereof, as defined herein, as a vaccine adjuvant, in the manufacture of a vaccine for the treatment of a disease or condition.

The present disclosure still further provides a method of treating, or reducing the risk of, a disease or condition, which method comprises administering to a patient in need thereof a therapeutically effective amount of a vaccine and at least one entity chosen from compounds of Formula (I) and pharmaceutically acceptable salts thereof, as defined herein.

The present disclosure still further provides a method of increasing the response to a vaccine in a patient, which method comprises administering to a patient in need thereof a therapeutically effective amount of a vaccine and at least one entity chosen from compounds of Formula (I) and pharmaceutically acceptable salts thereof, as defined herein.

Experimental Procedures (Chemical Syntheses and Biological Assays)

In the experimental procedures described below, the following abbreviations may be used:

"EtOAc"=ethyl acetate; "min(s)"=minute(s); "THF"=tetrahydrofuran; "DMF"=N,N-dimethylformamide; "NaH"=sodium hydride; "M"=mol/L; "h"=hour(s); "Amino silica gel"=flash column chromatography using silica that is surface-modified by aminopropyl (HiFlash Column Amino 40 μM 60 A; Cat. No. W091, W092 or W093 packed with silica gel that is surface-modified by aminopropyl, purchased from Yamazen Science, Inc); "DMSO"=dimethylsulfoxide; "Mes"=mesitylenyl; "Ms"=methanesulfonyl; "sat."=saturated aqueous solution; "RT"=room temperature; "LC-MS"=liquid chromatography with mass spectrometry; "m/z"=measured mass to charge ratio; "M"=molarity; "EtOH"=ethanol. Proton nuclear magnetic resonance data ("$^1$H NMR") was generally obtained at 300-500 MHz and using deuterated DMSO unless otherwise stated. Abbreviations used for 1H NMR are: "s"=singlet, "d"=doublet; "t"=triplet; "q"=quartet; "m"=multiplet; "dd"=doublet of doublets; "br s"=broad singlet; "dt"=doublet of triplets, "td"=triplet of doublets, etc.

Preparative reverse phase HPLC ("RPHPLC") was carried out using a Phenomenex Gemini™ C18 5 μm column, using CH$_3$CN in an aqueous 0.1% NH$_3$ solution as eluent. Fractions were collected following detection by UV spectroscopy at a wavelength such as 220 or 254 nm.

EXAMPLES

Example 1

(S)-2-((4-((2-amino-4-(1-hydroxyhexan-3-ylamino)-6-methylpyrimidin-5-yl)methyl)-3-methoxybenzyl)(ethyl)amino)acetic Acid

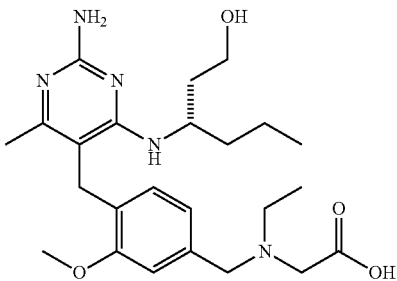 [SMILES: CCC[C@@H](CCO)Nc1nc(N)nc(C)c1Cc1ccc(CN(CC)CC(=O)O)cc1OC]

The title compound was prepared as described below:

(i) Methyl 3-methoxy-4-(2-(methoxycarbonyl)-3-oxobutyl)benzoate

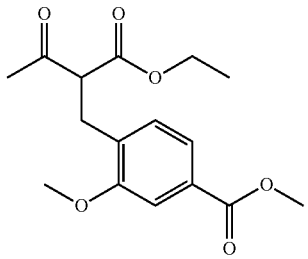 [SMILES: CCOC(=O)C(Cc1ccc(C(=O)OC)cc1OC)C(C)=O]

NaH (60% in mineral oil, 1.5 g) was added portion-wise over 10 mins to a solution of ethyl acetoacetate (4.4 mL) in THF (60 mL) at 0° C. The mixture was then stirred for 10 mins. Then, a solution of methyl 4-(bromomethyl)-3-methoxybenzoate (7.5 g) in THF (40 mL) was added and the mixture was warmed to 70° C. and stirred for 15 h. The mixture was then poured into ice/water (300 mL) and stirred for 30 mins. The resulting aqueous mixture was extracted with EtOAc. The organic extracts were combined, dried and concentrated in vacuo to provide crude product. The reaction was repeated on the same scale. The two batches of crude product were combined and purified by flash column chromatography on silica gel to give the sub-title compound (15 g) as a colourless oil; $^1$H NMR (300 MHz, CDCl$_3$) δ=7.48 (1H, dd), 7.45 (1H, d), 7.24 (1H, d), 4.05 (2H, q), 3.95 (1H, dd), 3.86 (3H, s), 3.84 (3H, s), 3.10 (1H, dd), 3.00 (1H, dd), 2.17 (3H, s), 1.09 (3H, t).

(ii) Methyl 4-((2-amino-4-hydroxy-6-methylpyrimidin-5-yl)methyl)-3-methoxybenzoate

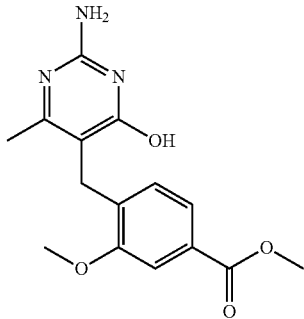

Guanidinium carbonate (7.2 g) was added to a solution of the product from step (i) (9.0 g) in EtOH (60 mL) and the mixture was then heated at 80° C. for 15 h. After cooling the resulting solid was collected by filtration. This solid was then suspended in water and collected by filtration. The solid was then washed with EtOAc and dried to give the sub-title compound (5.8 g) as a colourless solid, which was used without further purification; 1H NMR (300 MHz, d$_6$-DMSO) δ=10.78 (1H, s), 7.46 (1H, d), 7.45 (1H, s), 6.98 (1H, d), 6.42 (2H, s), 3.89 (3H, s), 3.83 (3H, s), 3.61 (2H, s), 1.93 (3H, s); LC-MS: m/z 304.

(iii) 2-amino-5-(4-(hydroxymethyl)-2-methoxybenzyl)-6-methylpyrimidin-4-ol

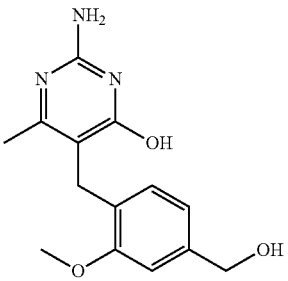 [SMILES: COc1cc(CO)ccc1Cc1c(C)nc(N)nc1O]

Lithium triethylborohydride (93 mL) was added to a solution of the product from step (ii) (5.0 g) in THF (25 mL) over 5 min and the reaction mixture was stirred at RT for 3.5 h. Water (60 mL) and 2M-hydrogen chloride (40 mL) was added to the mixture. The organic solvent was removed by evaporation. 2M-hydrogen chloride (16 mL) was added and the mixture was stirred at RT for 4 h. The mixture was neutralized by saturated aqueous sodium hydrogen carbonate. The precipitate was collected by filtration, washed with water and dried in vacuo at 50° C. to afford the sub-title compound (4.7 g) as a white solid; $^1$H NMR (300 MHz, d$_6$-DMSO); 10.76 (1H, br s), 6.89 (1H, s), 6.77-6.70 (2H, m), 6.30 (2H, br s), 5.10 (1H, t), 4.42 (2H, d), 3.79 (3H, s), 3.51 (2H, s), 1.91 (3H, s).

(iv) 2-amino-5-(4-(hydroxymethyl)-2-methoxybenzyl)-6-methylpyrimidin-4-yl 2,4,6-trimethylbenzenesulfonate

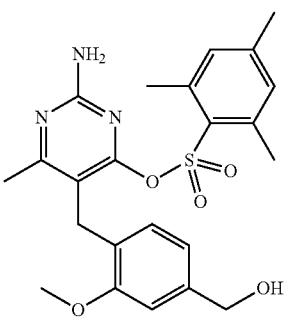

2-Mesitylenesulfonyl chloride (7.2 g) was added to a suspension of diisopropylethylamine (5.5 mL) and the product from step (iii) (6.1 g) in THF (200 mL) and the mixture was stirred under reflux for 12 h. The resulting mixture was diluted with water and extracted with EtOAc. The combined organic layer was washed with brine, dried and concentrated under reduced pressure. The residue was purified by flash column chromatography on amino silica gel to afford the sub-title compound (8.6 g) as a white solid; $^1$H NMR (300 MHz, CDCl$_3$); 6.92 (2H, s), 6.86 (1H, s), 6.77 (2H, s), 4.67 (2H, br s), 4.64 (2H, d), 3.82 (3H, s), 3.81 (3H, s), 2.57 (6H, s), 2.29 (3H, s), 2.21 (3H, s), 1.81 (1H, t).

(v) 2-amino-5-(4-(chloromethyl)-2-methoxybenzyl)-6-methylpyrimidin-4-yl 2,4,6-trimethylbenzenesulfonate

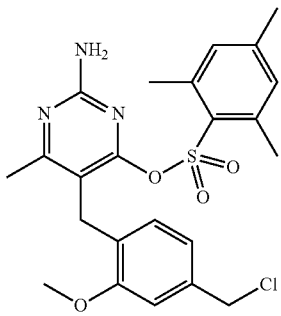

Methanesulfonyl chloride (1.4 mL) was added to a mixture of lithium chloride (0.74 g) and the product from step (iv) (4.0 g) in THF (45 mL). The mixture was stirred at RT for 1.5 h, diluted with water and extracted with EtOAc. The combined organic layer was washed with brine, dried and concentrated under reduced pressure to afford the crude product as a pale yellow oil, which was used for next reaction without further purification; $^1$H NMR (300 MHz, CDCl$_3$); 6.91 (2H, s), 6.83 (1H, s), 6.81-6.74 (2H, m), 4.69 (2H, br s), 4.54 (2H, s), 3.82 (3H, s), 3.80 (2H, s), 2.54 (6H, s), 2.29 (3H, s), 2.24 (3H, s).

(vi) ethyl 2-(ethylamino)acetate

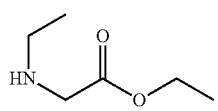

Sulfuric acid (3 mL) was added to a solution of N-ethylglycine (2.0 g) in EtOH (15 mL) and the mixture was stirred under reflux for 9 h. The mixture was cooled to RT and neutralized with 5M-sodium hydroxide, and saturated aqueous sodium hydrogen carbonate. The solution was extracted with EtOAc, the combined organic layer was washed with brine, dried and concentrated under reduced pressure. The sub-title compound (1.4 g) was obtained as a pale yellow oil; 1H NMR (300 MHz, CDCl$_3$); 4.17 (2H, q), 3.38 (2H, s), 2.63 (2H, q), 1.25 (3H, t), 1.10 (3H, t).

(vii) ethyl 2-((4-((2-amino-4-(mesitylsulfonyloxy)-6-methylpyrimidin-5-yl)methyl)-3-methoxybenzyl)(ethyl)amino)acetate

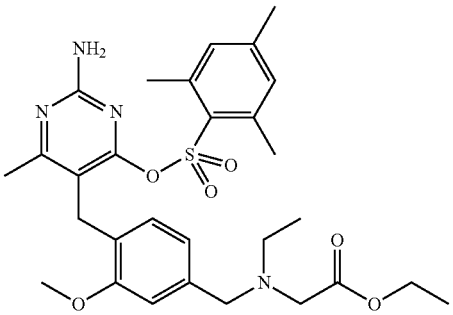 [SMILES: CCOC(=O)CN(CC)Cc1ccc(Cc2c(C)nc(N)nc2OS(=O)(=O)c2c(C)cc(C)cc2C)c(OC)c1]

The product from step (vi) (390 mg) was added to the mixture of potassium dicarbonate (410 mg), potassium iodide (49 mg) and the crude product from step (v) in acetonitrile (5 mL). After the mixture was stirred at 70° C. for 4 h, the reaction mixture was cooled to RT, filtered, and concentrated under reduced pressure. The residue was purified by flash column chromatography to afford the sub-title compound (490 mg) as a colourless amorphous solid; $^1$H NMR (300 MHz, CDCl$_3$); 6.91 (2H, s), 6.87 (1H, s), 6.72 (2H, s), 4.65 (2H, br s), 4.14 (2H, q), 3.82-3.79 (5H, m), 3.70 (2H, s), 3.28 (2H, s), 2.67 (2H, q), 2.56 (6H, s), 2.28 (3H, s), 2.23 (3H, s), 1.25 (3H, t), 1.07 (3H, t).

(viii) (S)-ethyl 2-((4-((2-amino-4-(1-hydroxyhexan-3-ylamino)-6-methylpyrimidin-5-yl)methyl)-3-methoxybenzyl)(ethyl)amino)acetate

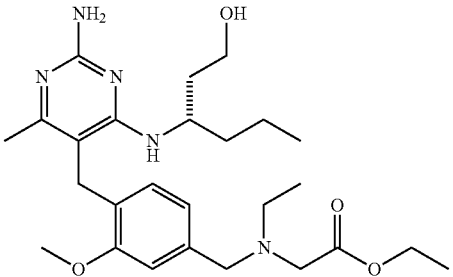 [SMILES: CCC[C@@H](CCO)Nc1nc(N)nc(C)c1Cc1ccc(CN(CC)CC(=O)OCC)cc1OC]

Trifluoroacetic acid (0.066 mL) was added to a mixture of (S)-3-aminohexan-1-ol (300 mg) and the product from step (vii) (490 mg) in propionitrile (5 mL). The mixture was heated at 120° C. for 16 h and cooled to RT. The solvent was removed by evaporation. The residue was purified by flash column chromatography on amino silica gel to afford the sub-title compound (330 mg) as a colourless gum; $^1$H NMR (CDCl$_3$); 6.94 (1H, s), 6.88 (1H, d), 6.79 (1H, d), 4.66 (1H, d), 4.58 (2H, br s), 4.13 (2H, q), 4.11-4.06 (1H, m), 3.88 (3H, s), 3.70 (2H, s), 3.66 (2H, s), 3.42 (1H, ddd), 3.28-3.20 (3H, m), 2.65 (2H, q), 2.34 (3H, s), 1.82-1.74 (1H, m), 1.45-1.33 (1H, m), 1.26-1.21 (5H, m), 1.07-1.02 (5H, m), 0.73 (3H, t).

(ix) (S)-2-((4-((2-amino-4-(1-hydroxyhexan-3-ylamino)-6-methylpyrimidin-5-yl)methyl)-3-methoxybenzyl)(ethyl)amino)acetic acid

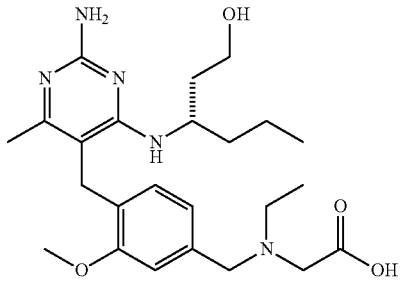 [SMILES: CCC[C@@H](CCO)Nc1nc(N)nc(C)c1Cc1ccc(CN(CC)CC(=O)O)cc1OC]

3M-sodium hydroxide (1 mL) was added to a solution of the product from step (viii) (310 mg) in methanol (3 mL). The solution was stirred at RT for 16 h. The reaction mixture was neutralized with 4M-hydrogen chloride (1 mL) and extracted with chloroform/EtOH (3/1). The combined organic layer was dried and concentrated under reduced pressure to afford the sub-title compound (300 mg) as a colourless amorphous solid; $^1$H NMR (DMSO); 7.00 (1H, s), 6.79 (1H, d), 6.72 (1H, d), 5.87 (2H, br s), 5.63 (1H, d), 4.20-4.14 (1H, m), 3.83 (3H, s), 3.76 (2H, s), 3.60 (2H, s), 3.27 (2H, q), 3.13 (2H, s), 2.66 (2H, q), 2.02 (3H, s), 1.60-1.51 (1H, m), 1.45-1.31 (3H, m), 1.13-1.06 (2H, m), 1.00 (3H, t), 0.75 (3H, t).

Example 2

2-((4-((2-amino-4-(butylamino)-6-methylpyrimidin-5-yl)methyl)-3-methoxybenzyl) (ethyl)amino)acetic acid

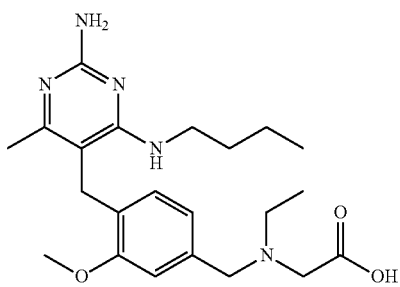 [SMILES: CCCCNc1nc(N)nc(C)c1Cc1ccc(CN(CC)CC(=O)O)cc1OC]

The title compound was prepared by the sequence of steps described below:

(i) ethyl 2-((4-((2-amino-4-(butylamino)-6-methylpyrimidin-5-yl)methyl)-3-methoxy-benzyl)(ethyl)amino)acetate

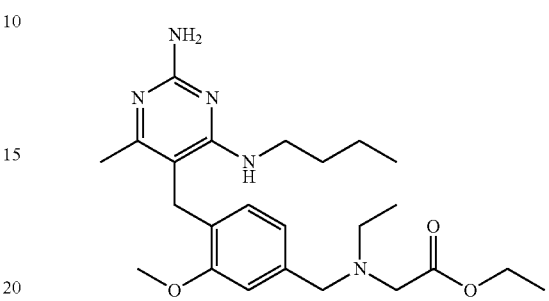

The sub-title compound was synthesized by the method of example 1 step (viii) from the product of example 1 step (vii) (150 mg) and 1-butylamine (56 mg). The sub-title compound (77 mg) was obtained as a yellow oil; 1H NMR (CDCl3); 6.94 (1H, s), 6.86 (1H, d), 6.77 (1H, d), 4.84 (1H, t), 4.55 (2H, br s), 4.13 (2H, q), 3.88 (3H, s), 3.70 (2H, s), 3.64 (2H, s), 3.30-3.23 (4H, m), 2.66 (2H, q), 2.30 (3H, s), 1.43-1.34 (2H, m), 1.24 (3H, t), 1.19-1.12 (2H, m), 1.06 (3H, t), 0.83 (3H, t).

(ii) 2-((4-((2-amino-4-(butylamino)-6-methylpyrimidin-5-yl)methyl)-3-methoxybenzyl)(ethyl)amino) acetic Acid The sub-title compound was synthesized by the method of example 1 step (ix) from the product of step (i) (71 mg). The sub-title compound (74 mg) was obtained as a cream solid; $^1$H NMR (DMSO); 7.00 (1H, s), 6.77 (1H, d), 6.65 (1H, d), 6.09 (1H, t), 5.85 (2H, br s), 3.83 (3H, s), 3.76 (2H, s), 3.58 (2H, s), 3.22 (2H, dt), 3.15 (2H, s), 2.66 (2H, q), 1.96 (3H, s), 1.44-1.34 (2H, m), 1.23-1.10 (2H, m), 1.00 (3H, t), 0.81 (3H, t).

Example 3

(S)-2-((4-((2-amino-4-(1-hydroxyhexan-3-ylamino)-6-methylpyrimidin-5-yl)methyl)-3-methoxybenzyl)(2,2-difluoroethyl)amino)acetic Acid

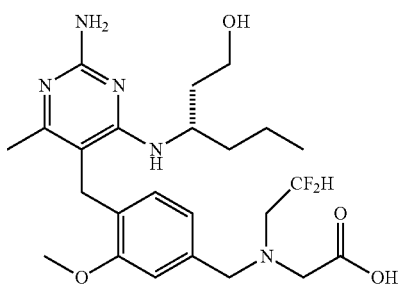 [SMILES: CCC[C@@H](CCO)Nc1nc(N)nc(C)c1Cc1ccc(CN(CC(=O)O)CC(F)F)cc1OC]

The title compound was prepared by the sequence of steps described below:

(i) ethyl 2-(2,2-difluoroethylamino)acetate

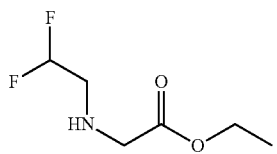

2,2-difluoroethylamine (4.0 g) was added to a suspension of ethyl bromoacetate (5.4 mL), potassium iodide (0.82 g), diisopropylethylamine (9.8 mL) in acetonitrile (100 mL) and the mixture was stirred at RT for 25 h. The mixture was concentrated under reduced pressure. The residue was purified by flash column chromatography on silica gel to afford the sub-title compound (7.0 g) as a colorless oil; 1H NMR (300 MHz, CDCl₃); 5.82 (1H, tt), 4.18 (2H, q), 3.46 (2H, s), 3.00 (2H, dt), 1.26 (3H, t).

(ii) ethyl 2-((4-((2-amino-4-(mesitylsulfonyloxy)-6-methylpyrimidin-5-yl)methyl)-3-methoxybenzyl)(2,2-difluoroethyl)amino)acetate

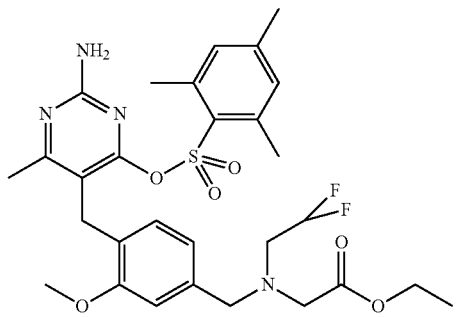 [SMILES: CCOC(=O)CN(Cc1ccc(Cc2c(C)nc(N)nc2OS(=O)(=O)c2c(C)cc(C)cc2C)c(OC)c1)CC(F)F]

The sub-title compound was synthesized by the method of example 1 step (vii) from the product of step (i) (490 mg) and example 1 step (v) (470 mg). The sub-title compound (520 mg) was obtained as a colourless amorphous solid; ¹H NMR (300 MHz, CDCl₃); 6.91 (2H, s), 6.83 (1H, s), 6.76-6.72 (2H, m), 5.75 (1H, tt), 4.65 (2H, br s), 4.10 (2H, q), 3.85 (2H, s), 3.79 (5H, s), 3.11-3.01 (4H, m), 2.55 (6H, s), 2.29 (3H, s), 2.24 (3H, s), 1.25 (3H, t).

(iii) (S)-ethyl 2-((4-((2-amino-4-(1-hydroxyhexan-3-ylamino)-6-methylpyrimidin-5-yl)methyl)-3-methoxybenzyl)(2,2-difluoroethyl)amino)acetate

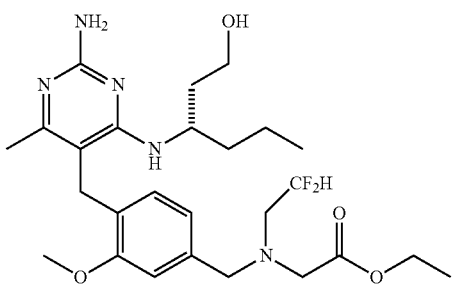 [SMILES: CCC[C@@H](CCO)Nc1nc(N)nc(C)c1Cc1ccc(CN(CC(=O)OCC)CC(F)F)cc1OC]

The sub-title compound was synthesized by the method of example 1 step (viii) from the product of step (ii) (520 mg) and (S)-3-aminohexan-1-ol (300 mg). The sub-title compound (340 mg) was obtained as a colourless gum; ¹H NMR (CDCl₃); 6.90-6.88 (2H, m), 6.78 (1H, d), 5.73 (1H, tt), 4.60 (1H, d), 4.55 (2H, br s), 4.15 (2H, q), 4.11-4.03 (1H, m), 3.88 (3H, s), 3.85 (2H, s), 3.66 (2H, s), 3.47-3.37 (3H, m), 3.25 (1H, ddd), 3.04 (2H, dt), 2.33 (3H, s), 1.83-1.73 (1H, m), 1.51-1.32 (3H, m), 1.25 (3H, t), 1.06-0.99 (2H, m), 0.73 (3H, t).

(iv) (S)-2-((4-((2-amino-4-(1-hydroxyhexan-3-ylamino)-6-methylpyrimidin-5-yl)methyl)-3-methoxybenzyl)(2,2-difluoroethyl)amino)acetic Acid

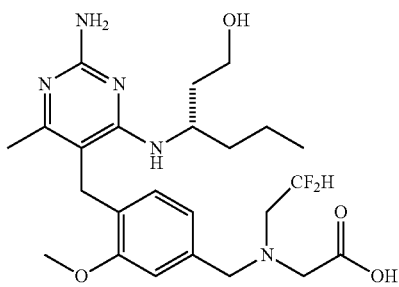 [SMILES: CCC[C@@H](CCO)Nc1nc(N)nc(C)c1Cc1ccc(CN(CC(=O)O)CC(F)F)cc1OC]

The sub-title compound was synthesized by the method of example 1 step (ix) from the product of step (iii) (330 mg). The sub-title compound (330 mg) was obtained as a colourless amorphous solid; ¹H NMR (DMSO); 6.94 (1H, s), 6.76-6.70 (2H, m), 6.40 (2H, br s), 6.02 (1H, tt), 5.93 (1H, d), 4.24-4.17 (1H, m), 3.82 (5H, s), 3.60 (2H, s), 3.31-3.25 (4H, m), 3.03 (2H, dt), 2.02 (3H, s), 1.60-1.54 (1H, m), 1.48-1.43 (1H, m), 1.38-1.32 (2H, m), 1.12-1.03 (2H, m), 0.75 (3H, t).

Example 4

(S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic Acid

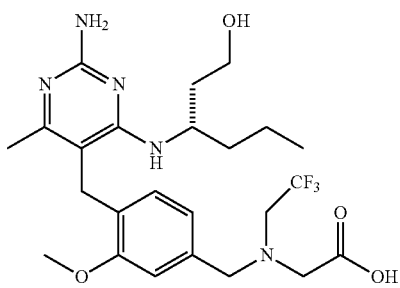 [SMILES: CCC[C@@H](CCO)Nc1nc(N)nc(C)c1Cc1ccc(CN(CC(=O)O)CC(F)(F)F)cc1OC]

The title compound was prepared by the sequence of steps described below:

(i) ethyl 2-(2,2,2-trifluoroethylamino)acetate

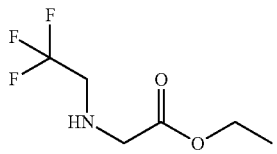

2,2,2-trifluoroethylamine (2.0 g) was added to a suspension of ethyl bromoacetate (2.3 mL), potassium iodide (0.34 g) in diisopropylethylamine (3.3 mL) and the mixture was stirred at RT for 5.5 h. The mixture was diluted with diethyl ether (30 mL), stirred at RT for 30 mins. The suspension was filtered and concentrated under reduced pressure. The sub-title compound (2.6 g) was obtained as a yellow oil; $^1$H NMR (300 MHz, CDCl$_3$); 4.19 (2H, q), 3.50 (2H, s), 3.22 (2H, q), 1.26 (3H, t).

(ii) ethyl 2-((4-((2-amino-4-(mesitylsulfonyloxy)-6-methylpyrimidin-5-yl)methyl)-3-methoxybenzyl)(2,2,2-trifluoroethyl)amino)acetate

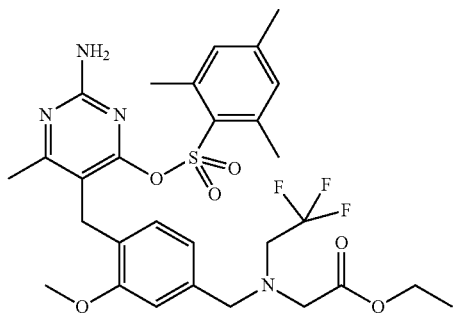 [SMILES: CCOC(=O)CN(Cc1ccc(Cc2c(C)nc(N)nc2OS(=O)(=O)c2c(C)cc(C)cc2C)c(OC)c1)CC(F)(F)F]

The sub-title compound was synthesized by the method of example 1 step (vii) from the product of step (i) (190 mg) and example 1 step (v) (500 mg). The sub-title compound (360 mg) was obtained as a yellow oil; $^1$H NMR (300 MHz, CDCl$_3$); 6.91 (2H, s), 6.86 (1H, s), 6.76-6.68 (2H, m), 4.67 (2H, br s), 4.15 (2H, q), 3.95 (2H, s), 3.79 (5H, s), 3.45 (2H, s), 3.35 (2H, q), 2.53 (6H, s), 2.29 (3H, s), 2.24 (3H, s), 1.04 (3H, t).

(iii) (S)-ethyl 2-((4-((2-amino-4-(1-hydroxyhexan-3-ylamino)-6-methylpyrimidin-5-yl)methyl)-3-methoxybenzyl)(2,2,2-trifluoroethyl)amino)acetate

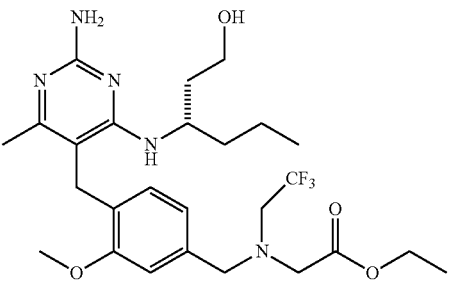 [SMILES: CCC[C@@H](CCO)Nc1nc(N)nc(C)c1Cc1ccc(CN(CC(=O)OCC)CC(F)(F)F)cc1OC]

The sub-title compound was synthesized by the method of example 1 step (viii) from the product of step (ii) (61 mg) and (S)-3-aminohexan-1-ol (34 mg). The sub-title compound (24 mg) was obtained as a pale yellow gum; $^1$H NMR (CDCl$_3$); 6.93 (1H, s), 6.89 (1H, d), 6.76 (1H, d), 4.62-4.59 (3H, m), 4.15 (2H, q), 4.10-4.04 (1H, m), 3.91 (2H, s), 3.87 (3H, s), 3.66 (2H, s), 3.44 (2H, s), 3.37-3.20 (4H, m), 2.33 (3H, s), 1.82-1.69 (1H, m), 1.42-1.32 (3H, m), 1.24 (3H, t), 1.09-0.98 (2H, m), 0.73 (3H, t).

(iv) (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic Acid

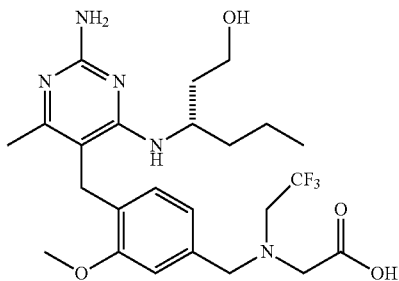 [SMILES: CCC[C@@H](CCO)Nc1nc(N)nc(C)c1Cc1ccc(CN(CC(=O)O)CC(F)(F)F)cc1OC]

The sub-title compound was synthesized by the method of example 1 step (ix) from the product of step (iii) (20 mg). The sub-title compound (20 mg) was obtained as a pale yellow solid; $^1$H NMR (DMSO); 6.90 (1H, s), 6.71 (2H, s), 5.79 (2H, br s), 5.52 (1H, d), 4.17-4.10 (1H, m), 3.87 (2H, s), 3.81 (3H, s), 3.58 (2H, s), 3.54-3.44 (2H, m), 3.23-3.17 (2H, m), 2.95 (2H, s), 2.03 (3H, s), 1.59-1.50 (1H, m), 1.45-1.23 (3H, m), 1.14-1.05 (2H, m), 0.76 (3H, t).

Example 5

(S)-3-((4-((2-amino-4-(1-hydroxyhexan-3-ylamino)-6-methylpyrimidin-5-yl)methyl)-3-methoxybenzyl)(ethyl)amino)propanoic Acid

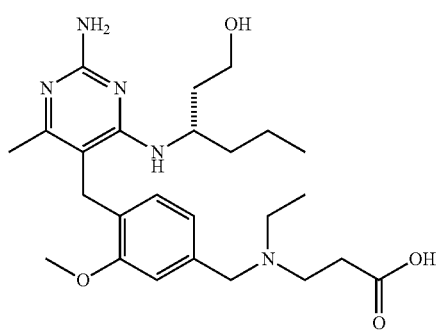 [SMILES: CCC[C@@H](CCO)Nc1nc(N)nc(C)c1Cc1ccc(CN(CC)CCC(=O)O)cc1OC]

The title compound was prepared by the sequence of steps described below:

(i) ethyl 3-(ethylamino)propanoate

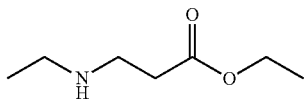

A solution of ethylamine (70% in water, 5.8 mL) in EtOH (30 mL) was added to a suspension of ethyl acrylate (2.0 g) in EtOH (20 mL) at 0° C. and the mixture was stirred at RT for 30 mins. The mixture was concentrated under reduced pressure. The residue was purified by flash column chromatography on amino silica gel to afford the sub-title compound (2.4 g) as a pale yellow oil; 1H NMR (300 MHz, CDCl$_3$); 4.13 (2H, q), 2.88 (2H, t), 2.66 (2H, q), 2.52 (2H, t), 1.24 (2H, t), 1.11 (3H, t).

(ii) ethyl 3-((4-((2-amino-4-(mesitylsulfonyloxy)-6-methylpyrimidin-5-yl)methyl)-3-methoxybenzyl)(ethyl)amino)propanoate

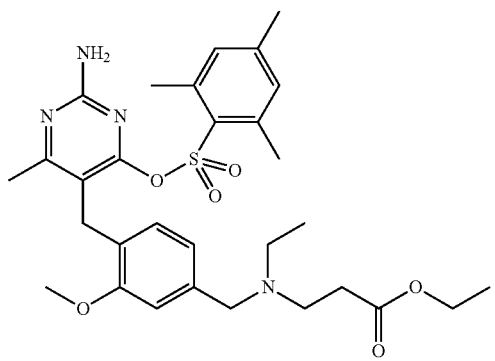 [SMILES: CCOC(=O)CCN(CC)Cc1ccc(Cc2c(C)nc(N)nc2OS(=O)(=O)c2c(C)cc(C)cc2C)c(OC)c1]

The sub-title compound was synthesized by the method of example 1 step (vii) from the product of step (i) and example 1 step (v) (3.1 g). The sub-title compound (2.7 g) was obtained as a yellow gum; $^1$H NMR (300 MHz, CDCl$_3$); 6.91 (2H, s), 6.82 (1H, s), 6.70 (2H, s), 4.65 (2H, br s), 4.10 (2H, q), 3.82-3.79 (5H, m), 3.51 (2H, s), 2.79 (2H, t), 2.56 (6H, s), 2.51-2.45 (4H, m), 2.28 (3H, s), 2.24 (3H, s), 1.21 (3H, t), 1.01 (3H, t).

(iii) (S)-ethyl 3-((4-((2-amino-4-(1-hydroxyhexan-3-ylamino)-6-methylpyrimidin-5-yl)methyl)-3-methoxybenzyl)(ethyl)amino)propanoate

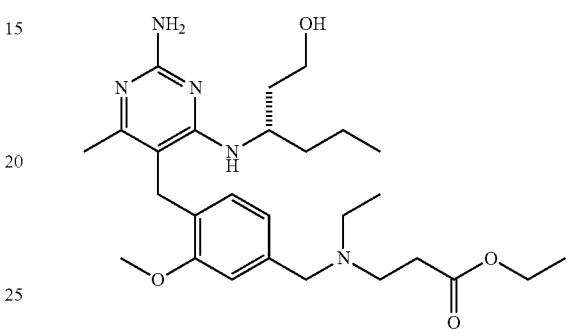

The sub-title compound was synthesized by the method of example 1 step (viii) from the product of step (ii) (2.7 g) (S)-3-aminohexan-1-ol (1.6 g). The sub-title compound (670 mg) was obtained as a colourless gum; $^1$H NMR (CDCl$_3$); 6.93 (1H, s), 6.86 (1H, d), 6.76 (1H, d), 4.80-4.65 (3H, m), 4.09 (2H, q), 3.88 (3H, s), 3.65 (2H, s), 3.50 (2H, s), 3.42-3.37 (1H, m), 3.24 (1H, ddd), 2.77 (2H, t), 2.46-2.41 (4H, m), 2.02 (3H, s), 1.82-1.72 (1H, m), 1.42-1.29 (1H, m), 1.26-1.19 (5H, m), 1.07-0.96 (5H, m), 0.74 (3H, t).

(iv) (S)-3-((4-((2-amino-4-(1-hydroxyhexan-3-ylamino)-6-methylpyrimidin-5-yl)methyl)-3-methoxybenzyl)(ethyl)amino)propanoic Acid

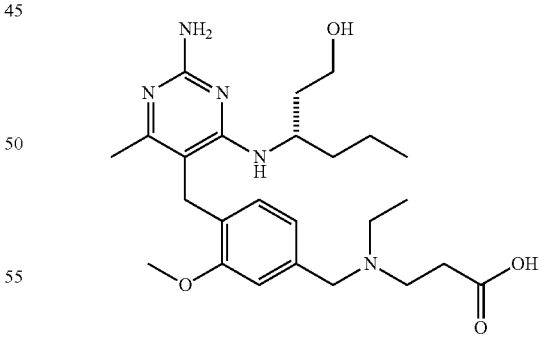

The sub-title compound was synthesized by the method of example 1 step (ix) from the product of step (iii) (670 mg). The subtitle compound (640 mg) was obtained as a white solid; $^1$H NMR (DMSO); 6.97 (1H, s), 6.79-6.70 (4H, m), 6.56-6.51 (1H, m), 4.31-4.23 (1H, m), 3.83 (3H, s), 3.64 (2H, s), 3.57 (2H, s), 3.33-3.26 (4H, m), 2.70 (2H, t), 2.36 (2H, t), 2.07 (3H, s), 1.60-1.49 (2H, m), 1.42-1.34 (2H, m), 1.13-1.04 (2H, m), 0.96 (3H, t), 0.76 (3H, t).

Example 6

(S)-3-((4-((2-amino-4-(1-hydroxyhexan-3-ylamino)-6-methylpyrimidin-5-yl)methyl)-3-methoxybenzyl)(2,2-difluoroethyl)amino)propanoic Acid

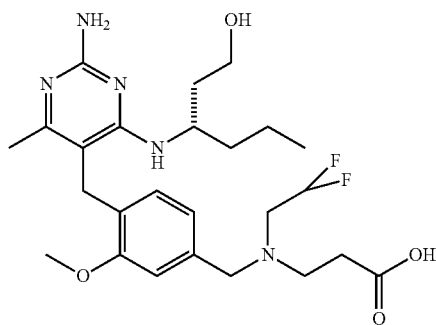 [SMILES: CCC[C@@H](CCO)Nc1nc(N)nc(C)c1Cc1ccc(CN(CCC(=O)O)CC(F)F)cc1OC]

The title compound was prepared by the sequence of steps described below:

(i) ethyl 3-(2,2-difluoroethylamino)propanoate

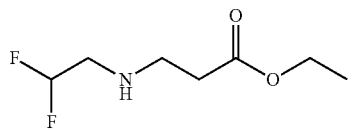

2,2-difluoroethylamine (0.50 g) was added to a suspension of ethyl 3-bromopropanoate (1.1 g), potassium iodide (0.10 g) in diisopropylethylamine (1.2 mL) and the mixture was stirred at 100° C. for 3.5 h. The mixture was cooled to RT and concentrated under reduced pressure. The residue was purified by flash column chromatography on silica gel to afford the sub-title compound (0.69 g) as a pale yellow oil; 1H NMR (300 MHz, CDCl$_3$); 5.81 (1H, tt), 4.13 (2H, q), 2.95 (2H, dt), 2.93 (2H, t), 2.48 (2H, t), 1.24 (3H, t).

(ii) ethyl 3-((4-((2-amino-4-(mesitylsulfonyloxy)-6-methylpyrimidin-5-yl)methyl)-3-methoxybenzyl)(2,2-difluoroethyl)amino)propanoate

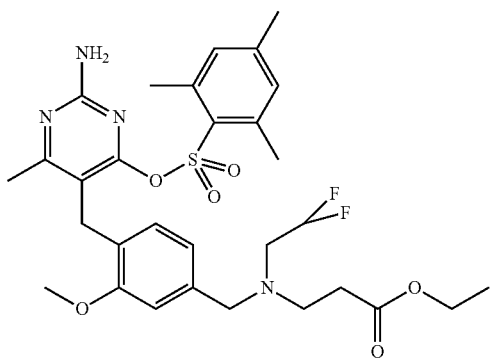 [SMILES: CCOC(=O)CCN(Cc1ccc(Cc2c(C)nc(N)nc2OS(=O)(=O)c2c(C)cc(C)cc2C)c(OC)c1)CC(F)F]

The sub-title compound was synthesized by the method of example 1 step (vii) from the product of step (i) and example 1 step (v) (260 mg). The sub-title compound (310 mg) was obtained as a pale yellow oil; $^1$H NMR (300 MHz, CDCl$_3$); 6.91 (2H, s), 6.80 (1H, s), 6.74 (1H, d), 6.68 (1H, d), 5.70 (1H, tt), 4.64 (2H, br s), 4.10 (2H, q), 3.79 (5H, s), 3.65 (2H, s), 2.80 (2H, dt), 2.55 (6H, s), 2.51-2.45 (4H, m), 2.29 (3H, s), 2.24 (3H, s), 1.24 (3H, t).

(iii) (S)-ethyl 3-((4-((2-amino-4-(1-hydroxyhexan-3-ylamino)-6-methylpyrimidin-5-yl)methyl)-3-methoxybenzyl)(2,2-difluoroethyl)amino)propanoate

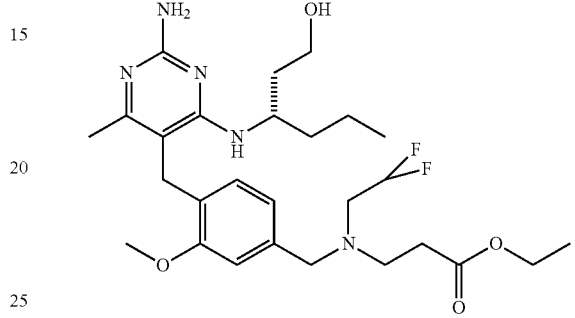

The sub-title compound was synthesized by the method of example 1 step (viii) from the product of step (ii) (190 mg) (S)-3-aminohexan-1-ol (110 mg). The sub-title compound (130 mg) was obtained as a colourless gum; 1H NMR (CDCl3); 6.91 (1H, s), 6.87 (1H, d), 6.79 (1H, d), 5.72 (1H, tt), 5.69 (2H, br s), 4.19-4.15 (2H, m), 4.11 (2H, q), 3.89 (3H, s), 3.65-3.64 (4H, m), 3.45-3.40 (1H, m), 3.21 (1H, ddd), 2.90 (2H, t), 2.78 (2H, dt), 2.48-2.43 (5H, m), 1.85-1.74 (1H, m), 1.49-1.37 (1H, m), 1.32-1.17 (5H, t), 1.09-0.99 (2H, m), 0.77 (3H, t).

(iv) (S)-3-((4-((2-amino-4-(1-hydroxyhexan-3-ylamino)-6-methylpyrimidin-5-yl)methyl)-3-methoxybenzyl)(2,2-difluoroethyl)amino)propanoic Acid

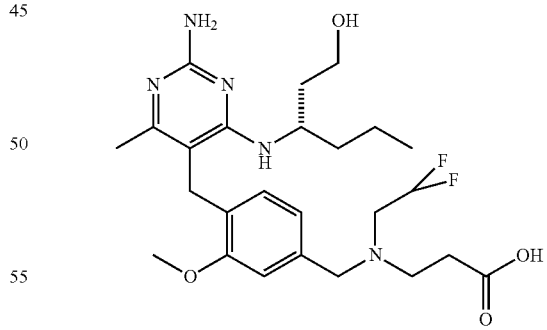

The sub-title compound was synthesized by the method of example 1 step (ix) from the product of step (iii) (120 mg). The sub-title compound (86 mg) was obtained as a white solid; $^1$H NMR (DMSO); 6.95 (1H, s), 6.75-6.68 (2H, m), 6.01 (1H, tt), 5.74 (2H, br s), 5.59 (1H, d), 4.19-4.12 (1H, m), 3.83 (3H, s), 3.62 (2H, s), 3.58 (2H, s), 3.49-3.21 (2H, m), 2.79 (2H, dt), 2.71 (2H, t), 2.19 (2H, t), 2.00 (3H, s), 1.59-1.50 (1H, m), 1.43-1.27 (3H, m), 1.16-1.05 (2H, m), 0.76 (3H, t).

Example 7

(S)-2-(N-(4-((2-amino-4-(1-hydroxyhexan-3-ylamino)-6-methylpyrimidin-5-yl)methyl)-3-methoxybenzyl)acetamido)acetic Acid

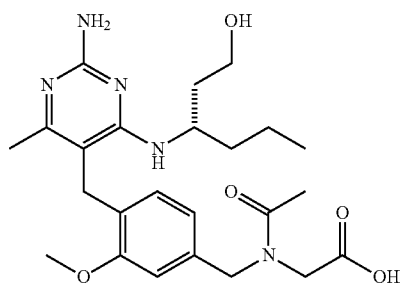 [SMILES: CCC[C@@H](CCO)Nc1nc(N)nc(C)c1Cc1ccc(CN(CC(=O)O)C(C)=O)cc1OC]

The title compound was prepared by the sequence of steps described below:

(i) ethyl 2-(4-((2-amino-4-(mesitylsulfonyloxy)-6-methylpyrimidin-5-yl)methyl)-3-methoxybenzylamino)acetate

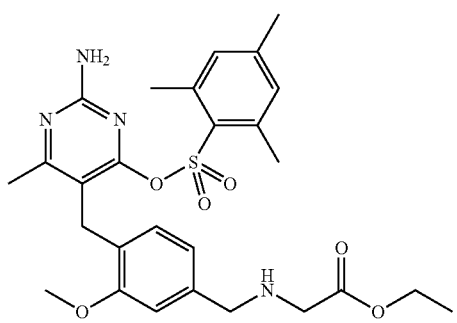 [SMILES: CCOC(=O)CNCc1ccc(Cc2c(C)nc(N)nc2OS(=O)(=O)c2c(C)cc(C)cc2C)c(OC)c1]

The sub-title compound was synthesized by the method of example 1 step (vii) from the product of example 1 step (v) (100 mg) and ethyl glycinate. The sub-title compound (23 mg) was obtained as a colourless amorphous solid; $^1$H NMR (300 MHz, CDCl$_3$); 6.92 (2H, s), 6.84 (1H, s), 6.76-6.70 (2H, m), 4.68 (2H, br s), 4.18 (2H, q), 3.81 (3H, s), 3.79 (2H, s), 3.77 (2H, s), 3.39 (2H, s), 2.56 (6H, s), 2.28 (3H, s), 2.22 (3H, s), 1.26 (3H, t); LC-MS: m/z=543.

(ii) ethyl 2-(N-(4-((2-amino-4-(mesitylsulfonyloxy)-6-methylpyrimidin-5-yl)methyl)-3-methoxybenzyl)acetamido)acetate

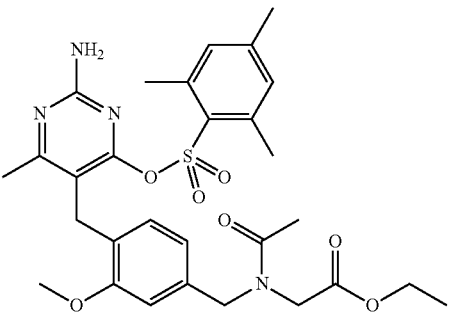 [SMILES: CCOC(=O)CN(Cc1ccc(Cc2c(C)nc(N)nc2OS(=O)(=O)c2c(C)cc(C)cc2C)c(OC)c1)C(C)=O]

Acetic anhydride (6 μL) was added to a solution of the product from step (i) (23 mg) and triethyl amine (9 μL) in THF (1 mL), and the mixture was stirred at RT for 3 h. The mixture was quenched with water, extracted with EtOAc, combined organic layer was washed with brine, dried and concentrated under reduced pressure. The sub-title compound (25 mg) was obtained as a colourless gum, which was used for next reaction without further purification; LC-MS: m/z=585.

(iii) (S)-ethyl 2-(N-(4-((2-amino-4-(1-hydroxyhexan-3-ylamino)-6-methylpyrimidin-5-yl)methyl)-3-methoxybenzyl)acetamido)acetate

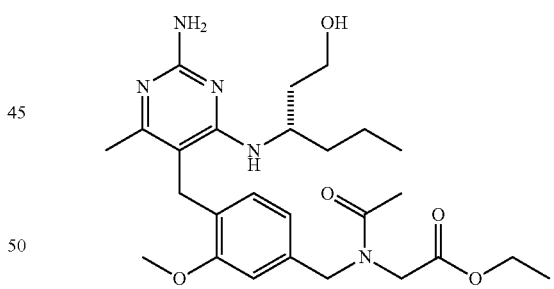

The sub-title compound was synthesized by the method of example 1 step (viii) from the product of step (ii) (25 mg) and (S)-3-aminohexan-1-ol (15 mg). The sub-title compound (5.1 mg) was obtained as a colourless gum; $^1$H NMR (CDCl$_3$); 6.93 (1H, d), 6.72-6.67 (2H, m), 4.82 (2H, br s), 4.65 (1H, d), 4.56 (2H, s), 4.18-4.08 (3H, m), 3.99 (2H, s), 3.88 (3H, s), 3.65 (2H, s), 3.48-3.42 (1H, m), 3.32-3.26 (1H, m), 2.33 (3H, s), 2.17 (3H, s), 1.84-1.74 (1H, m), 1.46-1.35 (1H, m), 1.23 (3H, t), 1.16-0.97 (4H, m), 0.73 (3H, t); LC-MS: m/z=502.

(iv) (S)-2-(N-(4-((2-amino-4-(1-hydroxyhexan-3-ylamino)-6-methylpyrimidin-5-yl)methyl)-3-methoxybenzyl)acetamido)acetic Acid

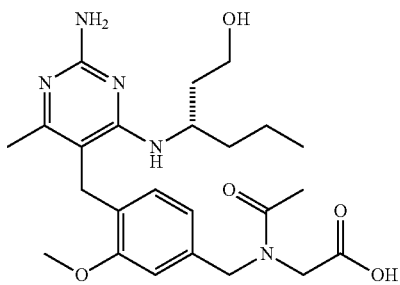 [SMILES: CCC[C@@H](CCO)Nc1nc(N)nc(C)c1Cc1ccc(CN(CC(=O)O)C(C)=O)cc1OC]

The sub-title compound was synthesized by the method of example 1 step (ix) from the product of step (iii) (330 mg). The sub-title compound (330 mg) was obtained as a colourless amorphous solid; $^1$H NMR (DMSO); 6.96-6.92 (4H, m), 6.81 (1H, d), 5.83 (1H, d), 4.73 (1H, d), 4.50 (1H, d), 4.21-4.10 (1H, m), 3.88 (3H, s), 3.80 (2H, s), 3.60 (2H, s), 3.21-3.06 (2H, m), 2.38 (3H, s), 2.14 (3H, s), 1.81-1.71 (1H, m), 1.43-1.37 (1H, m), 1.31-1.09 (4H, m), 0.82 (3H, t); LC-MS: m/z=474.

Example 8

(R)-1-(3-(4-((2-amino-4-((S)-1-hydroxyhexan-3-ylamino)-6-methylpyrimidin-5-yl)methyl)-3-methoxyphenoxy)propyl)pyrrolidine-2-carboxylic Acid

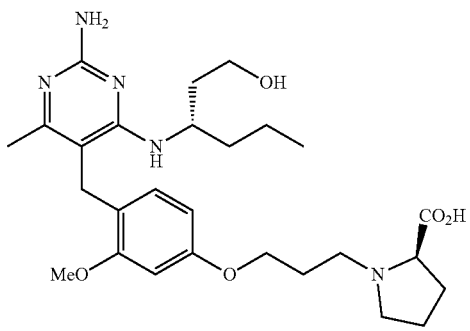 [SMILES: CCC[C@@H](CCO)Nc1nc(N)nc(C)c1Cc1ccc(OCCCN2CCC[C@@H]2C(=O)O)cc1OC]

The title compound may be prepared by the steps described below:

(i) 4-[3-(tert-Butyldimethylsilyloxy)propoxy]-2-methoxybenzaldehyde

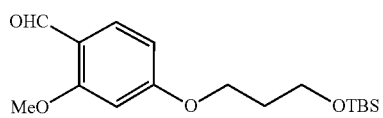 [SMILES: COc1cc(OCCCO[Si](C)(C)C(C)(C)C)ccc1C=O]

The mixture of 4-hydroxy-2-methoxybenzaldehyde (10.0 g), (3-bromopropoxy)-tert-butyldimethylsilane (25.0 g), and potassium dicarbonate (13.6 g) in DMF (100 mL) was stirred at RT for 5 h. The mixture was diluted with water and extracted with EtOAc. And the combined organic solutions were washed with water and brine, dried and concentrated. The residue was purified by silica gel chromatography eluting with hexane/EtOAc to give 21.3 g of the subtitle compound as a yellow oil [as a mixture with (3-bromopropoxy)-tert-butyldimethylsilane].

(ii) {4-[3-(tert-Butyldimethylsilyloxy)propoxy]-2-methoxyphenyl}methanol

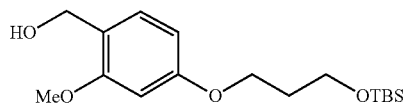 [SMILES: COc1cc(OCCCO[Si](C)(C)C(C)(C)C)ccc1CO]

Sodium borohydride (1.24 g) was added to a solution of the product from step (i) (21.3 g) in THF (100 mL), methanol (15 mL) and stirred at RT for 2.5 h. The mixture was diluted with water and brine, and extracted with EtOAc. And the combined organic solutions were dried and concentrated. The residue was purified by silica gel chromatography eluting with hexane/EtOAc to give the subtitle compound (18.5 g) as a colourless oil; $^1$H NMR: 7.14 (1H, d), 6.42-6.48 (2H, m), 4.61 (2H, d), 4.06 (2H, t), 3.84 (3H, s), 3.80 (2H, t), 2.15 (1H, t), 1.94-2.02 (2H, m), 0.89 (9H, s), 0.04 (6H, s).

(iii) tert-Butyl{3-[4-(chloromethyl)-3-methoxyphenoxy]propoxy}dimethylsilane

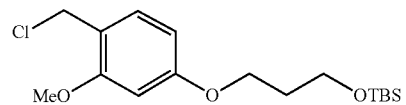 [SMILES: COc1cc(OCCCO[Si](C)(C)C(C)(C)C)ccc1CCl]

Methanesulfonyl chloride (4.02 mL) was added to the mixture of the product from step (ii) (8.47 g), diisopropylethylamine (13.4 mL) and lithium chloride (3.29 g) in THF (105 mL) at RT and stirred for 40 mins. The mixture was diluted with water and brine, and extracted with EtOAc. The combined organic solutions were washed with brine, dried and concentrated to give 10.0 g of the subtitle compound as a yellow oil; 1H NMR: 7.23 (1H, dd), 6.44-6.49 (2H, m), 4.63 (2H, s), 4.06 (2H, t), 3.85 (3H, s), 3.79 (2H, t), 1.94-2.02 (2H, m), 0.89 (9H, s), 0.04 (6H, s).

(iv) Methyl 2-{4-[3-(tert-butyldimethylsilyloxy)propoxy]-2-methoxybenzyl}-3-oxobutanoate

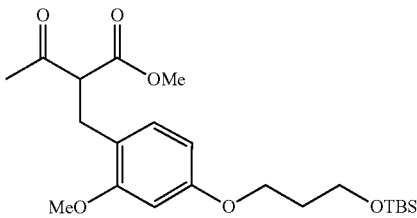 [SMILES: COC(=O)C(Cc1ccc(OCCCO[Si](C)(C)C(C)(C)C)cc1OC)C(C)=O]

Methyl acetoacetate (4.18 mL) was added to a suspension of NaH (55% oil dispersion, 1.70 g) in DMF (60 mL) at 0° C. and stirred at r.t. for 0.5 h. The product from step (iii) (10.0 g) in DMF (60 mL) and potassium iodide (4.73 g) were added to the mixture and stirred at 80° C. for 6 h. The mixture was cooled to RT and diluted with water and extracted with EtOAc. And the combined organic solutions were washed with water and brine, dried and concentrated. The residue was purified by silica gel chromatography to give 9.98 g of the subtitle compound as a yellow oil; 1H NMR: 6.99 (1H, d), 6.42 (1H, d), 6.37 (1H, dd), 4.02 (2H, t), 3.89 (1H, t), 3.80 (3H, s), 3.79 (2H, t), 3.67 (3H, s), 2.99-3.14 (2H, m), 2.17 (3H, s), 1.92-2.00 (2H, m), 0.88 (9H, s), 0.04 (6H, s).

(v) 2-Amino-5-{4-[3-(tert-butyldimethylsilyloxy)propoxy]-2-methoxybenzyl}-6-methylpyrimidin-4-ol

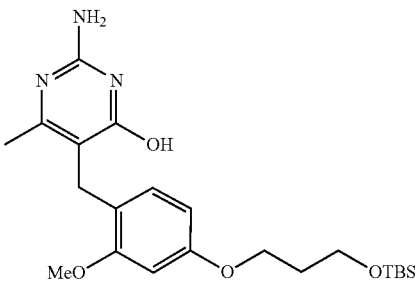 [SMILES: COc1cc(OCCCO[Si](C)(C)C(C)(C)C)ccc1Cc1c(C)nc(N)nc1O]

Guanidium carbonate (6.40 g) was added to a solution of the product from step (iv) (11.6 g) in methanol (116 mL) and heated at 75° C. for 8 h. The mixture was cooled to r.t. and concentrated. The residue was diluted with EtOAc (50 mL) and water (50 mL), and stirred for 5.5 h. The precipitate was collected and washed with water and EtOAc to afford 7.49 g of the subtitle compound as a white solid; $^1$H NMR: (d$^6$-DMSO) 10.75 (1H, br s), 6.71 (1H, d), 6.48 (1H, d), 6.36 (1H, dd), 6.30 (2H, br s), 3.97 (2H, t), 3.77 (3H, s), 3.73 (2H, t), 3.45 (2H, s), 1.92 (3H, s), 1.82-1.90 (2H, m), 0.85 (9H, s), 0.02 (6H, s).

(vi) 2-amino-5-(4-(3-hydroxypropoxy)-2-methoxybenzyl)-6-methylpyrimidin-4-ol hydrochloride

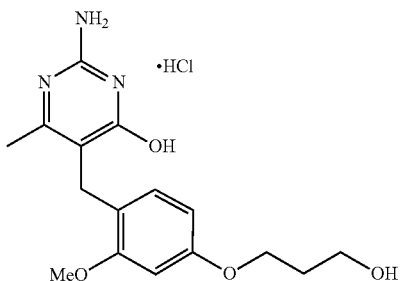 [SMILES: COc1cc(OCCCO)ccc1Cc1c(C)nc(N)nc1O ; Cl]

Concentrated hydrogen chloride (2.5 mL) was added dropwise to a solution of the product from step (v) (4.33 g) in methanol (43 mL) at RT and stirred for 14 h. The mixture was concentrated and diluted with methanol. The precipitate was collected by filtration, washed with methanol and dried to give 2.87 g of the sub-title compound as a white solid, which was used without further purification; 1H NMR (300 MHz, d$_6$-DMSO) 5=12.59 (2H, brs), 8.05 (2H, s), 6.89 (1H, d), 6.51 (1H, d), 6.36 (1H, dd), 3.97 (2H, t), 3.52 (2H, t), 3.46 (2H, s), 2.13 (3H, s), 1.78-1.86 (2H, m); LC-MS: m/z 320.

(vii) 2-amino-5-(4-(3-hydroxypropoxy)-2-methoxybenzyl)-6-methylpyrimidin-4-yl 2,4,6-trimethylbenzenesulfonate

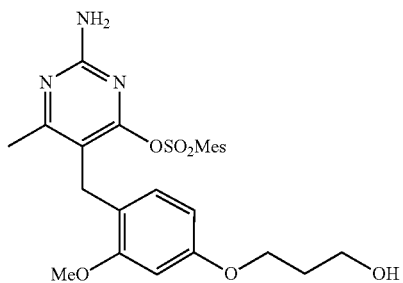

2-Mesitylenesulfonyl chloride (2.7 g) was added to a suspension of diisopropylethylamine (4.6 mL) and the product from step (vi) (2.9 g) in THF (200 mL) and the mixture was stirred under reflux for 18 h. The resulting mixture was diluted with water and extracted with EtOAc. The combined organic layer was washed with brine, dried and concentrated under reduced pressure. The residue was purified by flash column chromatography on amino silica gel to afford the sub-title compound (3.6 g) as a white solid; $^1$H NMR (300 MHz, CDCl$_3$); 6.92 (2H, s), 6.71 (1H, d), 6.40 (1H, d), 6.32 (1H, dd), 4.70 (2H, br s), 4.07 (2H, t), 3.88-3.82 (2H, m), 3.76 (3H, s), 3.73 (2H, s), 2.57 (6H, s), 2.29 (3H, s), 2.24 (3H, s), 2.06-1.98 (2H, m); LC-MS: m/z 502.

(viii) 2-amino-5-(2-methoxy-4-(3-(methylsulfonyloxy)propoxy)benzyl)-6-methylpyrimidin-4-yl 2,4,6-trimethylbenzenesulfonate

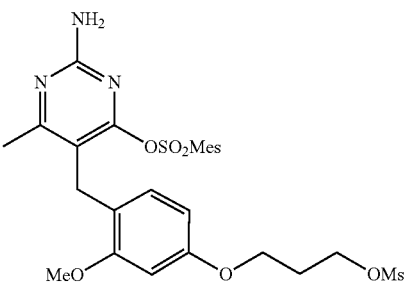

Methanesulfonyl chloride (0.293 mL) was added to a solution of diisopropylethylamine (0.988 mL) and the product from step (vii) (0.95 g) in THF (9.5 mL). The mixture was stirred at RT for 2 h, diluted with water and extracted with EtOAc. The combined organic layer was washed with brine, dried and concentrated under reduced pressure to afford the crude product as a pale yellow oil, which was used for next reaction without further purification; $^1$H NMR (300 MHz, CDCl$_3$); 6.93 (2H, s), 6.73 (1H, d), 6.39 (1H, d), 6.31 (1H, dd), 4.76 (2H, br s), 4.43 (2H, t), 4.03 (2H, t), 3.77 (3H, s), 3.73 (2H, s), 2.98 (3H, s), 2.57 (6H, s), 2.29 (3H, s), 2.25 (3H, s), 2.24-2.16 (2H, m); LC-MS: m/z 580.

(ix) (R)-tert-butyl 1-(3-(4-((2-amino-4-(mesitylsulfonyloxy)-6-methylpyrimidin-5-yl)methyl)-3-methoxyphenoxy)propyl)pyrrolidine-2-carboxylate

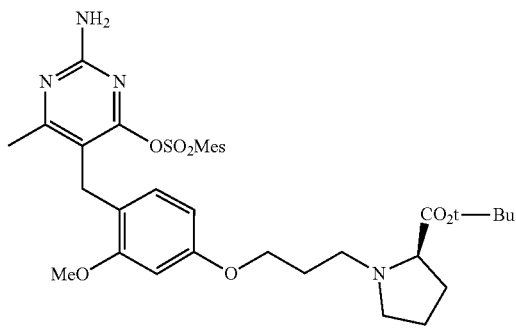

(R)-tert-butyl pyrrolidine-2-carboxylate (485 mg) was added to the mixture of potassium carbonate (393 mg), potassium iodide (31 mg) and the crude product from step (viii) in CH$_3$CN (20 mL). After the mixture was stirred at 70° C. for 16 h, the reaction mixture was cooled to RT, diluted with water and extracted with EtOAc. The combined organic layer was washed with water and brine, dried and concentrated under reduced pressure. The residue was purified by flash column chromatography on amino silica gel to afford the sub-title compound (975 mg) as a white amorphous solid; $^1$H NMR (300 MHz, CDCl$_3$); 6.92 (2H, s), 6.67 (1H, d), 6.39 (1H, d), 6.30 (1H, dd), 4.64 (2H, br s), 4.03-3.90 (2H, m), 3.76 (3H, s), 3.73 (2H, s), 3.20-3.00 (2H, m), 2.96-2.80 (1H, m), 2.66-2.50 (1H, m), 2.57 (6H, s), 2.46-2.30 (1H, m), 2.28 (3H, s), 2.22 (3H, s), 2.21-1.74 (6H, m), 1.43 (9H, s); LC-MS: m/z 655.

(x) (R)-tert-butyl 1-(3-(4-((2-amino-4-((S)-1-hydroxyhexan-3-ylamino)-6-methylpyrimidin-5-yl)methyl)-3-methoxyphenoxy)propyl)pyrrolidine-2-carboxylate

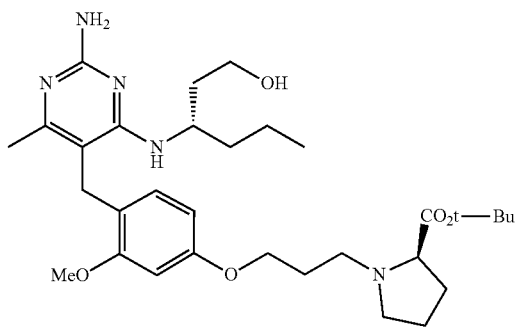

Trifluoroacetic acid (0.091 mL) was added to the mixture of (S)-3-aminohexan-1-ol (416 mg) and the product from step (ix) (775 mg) in propionitrile (8 mL). After the mixture was heated at 120° C. for 16 h, the reaction mixture was cooled to RT, diluted with sat. sodium hydrogen dicarbonate and extracted with EtOAc. The combined organic layer was dried and concentrated under reduced pressure. The residue was purified by flash column chromatography on amino silica gel to afford the sub-title compound (520 mg) as a white gum; $^1$H NMR (CDCl$_3$); 6.81 (1H, d), 6.44 (1H, d), 6.38 (1H, dd), 4.80 (2H, br s), 4.13-4.03 (1H, m), 4.03-3.90 (2H, m), 3.84 (3H, s), 3.59 (2H, s), 3.49-3.37 (1H, m), 3.34-3.22 (1H, m), 3.18-3.08 (1H, m), 3.08-3.00 (1H, m), 2.91-2.80 (1H, m), 2.62-2.49 (1H, m), 2.41-2.30 (1H, m), 2.35 (3H, s), 2.10-1.70 (8H, m), 1.44-1.34 (1H, m), 1.42 (9H, s), 1.28-0.89 (4H, m), 0.75 (3H, t); LC-MS: m/z 573.

(xi) (R)-1-(3-(4-((2-amino-4-((S)-1-hydroxyhexan-3-ylamino)-6-methylpyrimidin-5-yl)methyl)-3-methoxyphenoxy)propyl)pyrrolidine-2-carboxylic Acid Trifluoroacetic acid (6 mL) was added to the product from step (x) (505 mg) and the mixture was stirred at RT for 14 h. After the reaction mixture was concentrated, 1M-sodium hydroxide (20 mL) and methanol (10 mL) was added to the residue and the mixture was stirred in methanol for 30 mins. The reaction mixture was concentrated, diluted with water and washed with chloroform. The aqueous layer was neutralized with 6M-hydrogen chloride and sat. sodium hydrogen dicarbonate and extracted with chloroform/EtOH (3/1). The combined organic layer was dried and concentrated. The residue was diluted with chloroform, filtered, concentrated and diluted with chloroform/EtOAc. The precipitate was collected by filtration, washed with EtOAc and dried to give 450 mg of the sub-title compound as a white solid; $^1$H NMR (CDCl$_3$); 6.78 (1H, d), 6.48 (1H, d), 6.38 (1H, dd), 5.35-5.20 (1H, m), 4.20-3.97 (3H, m), 3.86 (3H, s), 3.55 (2H, s), 3.63-3.47 (1H, m), 3.40-3.09 (4H, m), 2.91-2.75 (1H, m), 2.60-2.45 (1H, m), 2.35 (3H, s), 2.30-2.02 (4H, m), 2.02-1.70 (3H, m), 1.50-1.33 (1H, m), 1.33-0.95 (5H, m), 0.77 (3H, t); LC-MS: m/z 516.

Example 9

(S)-1-(3-(4-((2-amino-4-((S)-1-hydroxyhexan-3-ylamino)-6-methylpyrimidin-5-yl)methyl)-3-methoxyphenoxy)propyl)pyrrolidine-2-carboxylic Acid

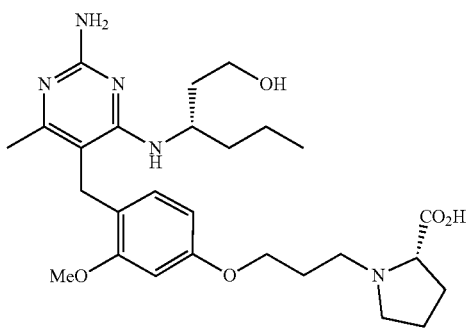 [SMILES: CCC[C@@H](CCO)Nc1nc(N)nc(C)c1Cc1ccc(OCCCN2CCC[C@H]2C(=O)O)cc1OC]

The title compound may be prepared by the steps described below:

(i) 2-Amino-5-{4-[3-(tert-butyldimethylsilyloxy)propoxy]-2-methoxybenzyl}-6-methylpyrimidin-4-yl 2,4,6-trimethylbenzenesulfonate

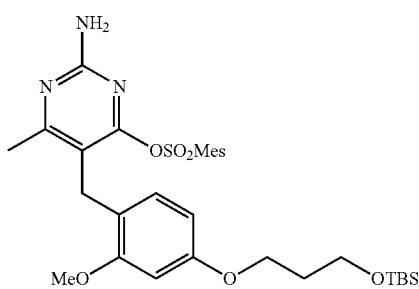

2-Mesitylenesulfonyl chloride (4.96 g, 22.7 mmol) was added to a solution of N,N,N',N'-tetramethyl-1,3-propanediamine (3.79 mL, 22.7 mmol) and the product of example 8 step (v) (6.55 g, 15.1 mmol) in THF (66 mL) and the mixture was stirred at RT for 3 h. The resulting mixture was diluted with water and extracted with EtOAc. And the combined organic solutions were washed with brine, dried and concentrated. The residue was purified via chromatography on silica to give 8.87 g of the subtitle compound as a white solid; 1H NMR (CDCl$_3$); 6.93 (2H, s), 6.71 (1H, d), 6.41 (1H, d), 6.33 (1H, dd), 4.66 (2H, br s), 4.02 (2H, t), 3.78 (3H, s), 3.77-3.82 (2H, m), 3.75 (2H, t), 2.59 (6H, s), 2.31 (3H, s), 2.25 (3H, s), 1.93-2.01 (2H, m), 0.89 (9H, s), 0.05 (6H, s); LC-MS: m/z 616.

(ii) (S)-3-(2-amino-5-(4-(3-(tert-butyldimethylsilyloxy)propoxy)-2-methoxybenzyl)-6-methylpyrimidin-4-ylamino)hexan-1-ol

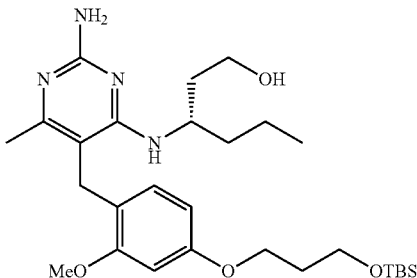 [SMILES: CCC[C@@H](CCO)Nc1nc(N)nc(C)c1Cc1ccc(OCCCO[Si](C)(C)C(C)(C)C)cc1OC]

Trifluoroacetic acid (0.154 mL) was added to the mixture of (S)-3-aminohexan-1-ol (586 mg) and the product from step (i) (616 mg) in propionitrile (6 mL). After the mixture was heated at 120° C. for 23 h, the reaction mixture was cooled to RT, diluted with sat. sodium hydrogen carbonate and extracted with EtOAc. The combined organic layer was dried and concentrated under reduced pressure. The residue was purified by flash column chromatography on amino silica gel to afford the sub-title compound (430 mg) as a colorless oil; 1H NMR (CDCl$_3$); 6.83 (1H, d), 6.44 (1H, d), 6.39 (1H, dd), 4.79 (2H, br s), 4.15-4.04 (1H, m), 4.00 (2H, t), 3.85 (3H, s), 3.77 (2H, t), 3.60 (2H, s), 3.50-3.40 (1H, m), 3.33-3.22 (1H, m), 2.36 (3H, s), 2.00-1.88 (2H, m), 1.86-1.71 (1H, m), 1.48-1.32 (1H, m), 1.30-0.95 (4H, m), 0.86 (9H, s), 0.75 (3H, t), 0.01 (6H, s); LC-MS: m/z 534.

(iii) (S)-3-(2-amino-5-(4-(3-(tert-butyldimethylsilyloxy)propoxy)-2-methoxybenzyl)-6-methylpyrimidin-4-ylamino)hexyl acetate

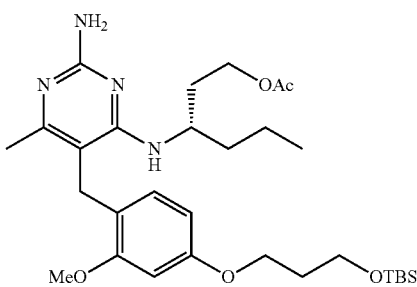 [SMILES: CCC[C@@H](CCOC(C)=O)Nc1nc(N)nc(C)c1Cc1ccc(OCCCO[Si](C)(C)C(C)(C)C)cc1OC]

4-Dimethylaminopyridine (cat. amount) was added to the mixture of acetic anhydride (0.162 mL), diisopropylethylamine (0.697 mL) and the product from step (ii) (760 mg) in THF (10 mL). After the mixture was stirred at RT for 3.5 h, the reaction mixture was diluted with water and sat. sodium hydrogen dicarbonate and extracted with EtOAc. The combined organic layer was washed with water and brine, dried and concentrated under reduced pressure to afford the crude product as pale yellow oil, which was used for next reaction without further purification; 1H NMR (CDCl$_3$); 6.81 (1H, d), 6.44 (1H, d), 6.38 (1H, dd), 4.79 (2H, br s), 4.25-4.15 (1H, m), 3.99 (2H, t), 3.96-3.88 (2H, m), 3.85 (3H, s), 3.76 (2H, t), 3.58 (2H, s), 2.33 (3H, s), 1.97 (3H, s), 2.00-1.88 (2H, m), 1.86-1.71 (1H, m), 1.64-1.50

(1H, m), 1.48-1.32 (1H, m), 1.30-0.95 (3H, m), 0.86 (9H, s), 0.76 (3H, t), 0.02 (6H, s); LC-MS: m/z 576.

(iv) (S)-3-(2-amino-5-(4-(3-hydroxypropoxy)-2-methoxybenzyl)-6-methylpyrimidin-4-yl-amino) hexyl acetate

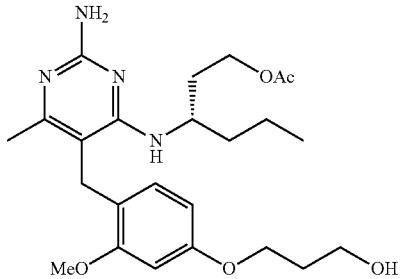 [SMILES: CCC[C@@H](CCOC(C)=O)Nc1nc(N)nc(C)c1Cc1ccc(OCCCO)cc1OC]

Tetra-n-butylammonium fluoride (561 mg) was added to the mixture of the product from step (iii) in THF (14 mL). After the mixture was stirred at RT for 1.5 h, the reaction mixture was diluted with water and sat. sodium hydrogen carbonate and extracted with EtOAc. The combined organic layer was washed with brine, dried and concentrated under reduced pressure. The residue was purified by flash column chromatography on amino silica gel to afford the sub-title compound (660 mg) as a colourless oil; $^1$H NMR (CDCl$_3$); 6.82 (1H, d), 6.45 (1H, d), 6.39 (1H, dd), 4.71 (2H, br s), 4.23-4.13 (1H, m), 4.07 (2H, t), 3.85 (3H, s), 3.85-3.74 (4H, m), 3.58 (2H, s), 2.33 (3H, s), 2.15 (1H, br s), 2.04-1.97 (2H, m), 1.97 (3H, s), 1.88-1.75 (1H, m), 1.60-1.47 (1H, m), 1.45-1.32 (1H, m), 1.31-1.19 (1H, m), 1.17-1.03 (2H, m), 0.79 (3H, t); LC-MS: m/z 461.

(v) (S)-3-(2-amino-5-(2-methoxy-4-(3-(methylsulfonyloxy)propoxy)benzyl)-6-methylpyrimidin-4-ylamino)hexyl acetate

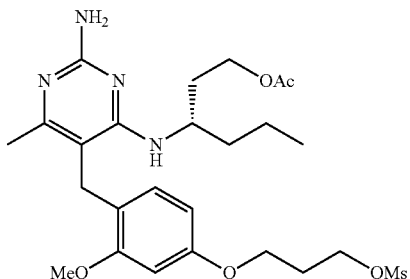 [SMILES: CCC[C@@H](CCOC(C)=O)Nc1nc(N)nc(C)c1Cc1ccc(OCCCOS(C)(=O)=O)cc1OC]

Methanesulfonyl chloride (0.083 mL) was added to a solution of diisopropylethylamine (0.279 mL) and the product from step (iv) (0.246 g) in THF (10 mL). The mixture was stirred at RT for 3 h and additional diisopropylethylamine (0.14 mL) and methanesulfonyl chloride (0.042 mL) was added. The mixture was stirred at RT for 2 h, diluted with water and sat. sodium hydrogen dicarbonate and extracted with EtOAc. The combined organic layer was dried and concentrated under reduced pressure to afford the crude product (300 mg) as a pale yellow oil, which was used for the next reaction without further purification; LC-MS: m/z 539.

(vi) (S)-methyl 1-(3-(4-((4-((S)-1-acetoxyhexan-3-ylamino)-2-amino-6-methylpyrimidin-5-yl)methyl)-3-methoxyphenoxy)propyl)pyrrolidine-2-carboxylate

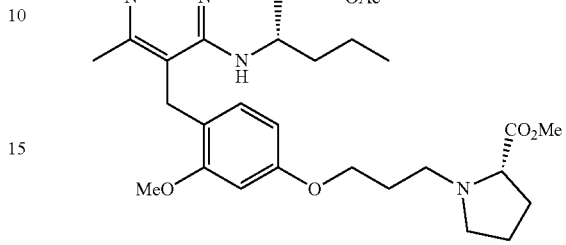

(S)-methyl pyrrolidine-2-carboxylate hydrochloride (44 mg) was added to the mixture of potassium carbonate (74 mg), potassium iodide (3 mg) and the crude product (75 mg) from step (v) in acetonitrile (2 mL). After the mixture was stirred at 70° C. for 16 h, the reaction mixture was cooled to RT, diluted with water and sat. sodium hydrogen dicarbonate and extracted with EtOAc. The combined organic layer was dried and concentrated under reduced pressure. The residue was purified by flash column chromatography on amino silica gel to afford the sub-title compound (60 mg) as a colourless oil; 1H NMR (CDCl$_3$); 6.80 (1H, d), 6.44 (1H, d), 6.37 (1H, dd), 4.85 (2H, br s), 4.24-4.15 (1H, m), 4.00-3.87 (4H, m), 3.85 (3H, s), 3.67 (3H, s), 3.57 (2H, s), 3.22-3.14 (2H, m), 2.89-2.78 (1H, m), 2.61-2.50 (1H, m), 2.42-2.30 (1H, m), 2.34 (3H, s), 2.16-2.05 (1H, s), 1.97 (3H, s), 1.97-1.70 (6H, m), 1.63-1.49 (1H, m), 1.46-1.32 (1H, m), 1.29-1.15 (1H, m), 1.12-0.98 (2H, m), 0.77 (3H, t); LC-MS: m/z 572.

(vii) (S)-1-(3-(4-((2-amino-4-((S)-1-hydroxyhexan-3-ylamino)-6-methylpyrimidin-5-yl)methyl)-3-methoxyphenoxy)propyl)pyrrolidine-2-carboxylic Acid

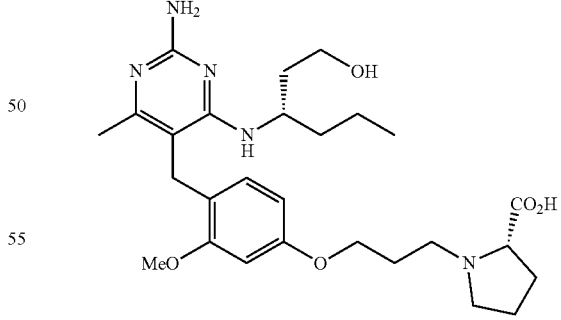

1M-sodium hydroxide (2 mL) was added to a solution of the product (60 mg) from step (vi) in methanol (2 mL) and the mixture was stirred at RT for 9 h. The reaction mixture was concentrated, diluted with water and washed with chloroform. The aqueous layer was neutralized with 2M-hydrogen chloride and extracted with chloroform/EtOH (3/1). The combined organic layer was dried and concentrated. The residue was diluted with chloroform, filtered, concentrated under reduced pressure to afford the sub-title compound (48 mg) as a white solid; 1H NMR (CDCl$_3$); 6.79 (1H, d), 6.48 (1H, d), 6.38 (1H, dd), 6.17 (1H, br s), 5.24 (1H, br s), 4.20-3.97 (3H, m), 3.85 (3H, s), 3.70-3.58 (1H, m), 3.55 (2H, s), 3.48-3.34 (2H, m), 3.32-3.15 (2H, m), 3.05-2.80 (1H, m), 2.75-2.55 (1H, m), 2.35 (3H, s), 2.30-2.07 (4H, m), 2.05-1.85 (2H, m), 1.85-1.70 (1H, m), 1.48-1.34 (1H, m), 1.33-0.98 (4H, m), 0.77 (3H, t); LC-MS: m/z 516.

Example 10

(S)-3-((3-(4-((2-amino-4-(1-hydroxyhexan-3-ylamino)-6-methylpyrimidin-5-yl)methyl)-3-methoxyphenoxy)propyl)(ethyl)amino)propanoic Acid

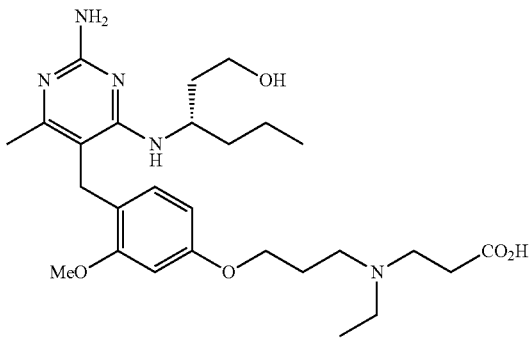 [SMILES: CCC[C@@H](CCO)Nc1nc(N)nc(C)c1Cc1ccc(OCCCN(CC)CCC(=O)O)cc1OC]

The title compound may be prepared by the steps described below:

(i) (S)-ethyl 3-((3-(4-((4-(1-acetoxyhexan-3-ylamino)-2-amino-6-methylpyrimidin-5-yl)methyl)-3-methoxyphenoxy)propyl)(ethyl)amino)propanoate

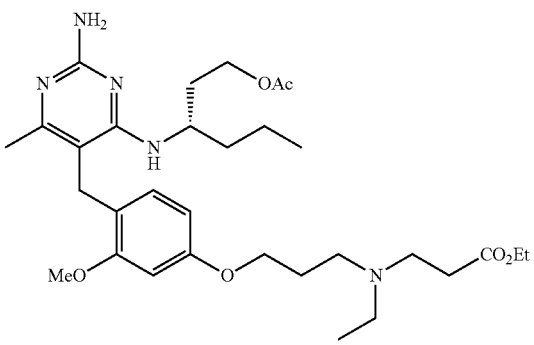 [SMILES: CCC[C@@H](CCOC(C)=O)Nc1nc(N)nc(C)c1Cc1ccc(OCCCN(CC)CCC(=O)OCC)cc1OC]

The sub-title compound was synthesized by the method of example 9 step (vi) from the product of example 9 step (v) (75 mg) and the product of example 5 step (i). The sub-title compound (60 mg) was obtained as a pale yellow oil; $^1$H NMR (300 MHz, CDCl$_3$); 6.81 (1H, d), 6.45 (1H, d), 6.37 (1H, dd), 4.95 (2H, br s), 4.28-4.13 (1H, m), 4.09 (2H, q), 3.97-3.86 (4H, m), 3.86 (3H, s), 3.57 (2H, s), 2.77 (2H, t), 2.56 (2H, t), 2.50 (2H, q), 2.41 (2H, t), 2.35 (3H, s), 1.97 (3H, s), 1.92-1.70 (3H, m), 1.63-1.50 (1H, m), 1.46-1.32 (1H, m), 1.30-1.15 (2H, m), 1.22 (3H, t), 1.13-0.95 (2H, m), 0.99 (3H, t), 0.77 (3H, t); LC-MS: m/z 588.

(ii) (S)-3-((3-(4-((2-amino-4-(1-hydroxyhexan-3-ylamino)-6-methylpyrimidin-5-yl)methyl)-3-methoxyphenoxy)propyl)(ethyl)amino)propanoic Acid

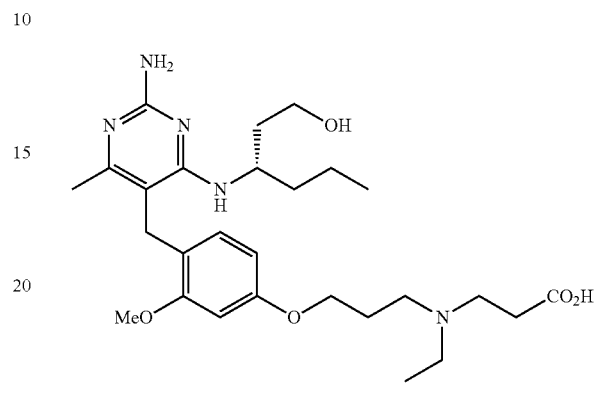

The sub-title compound was synthesized by the method of example 9 step (vii) from the product of step (i) (60 mg). The sub-title compound (47 mg) was obtained as a white amorphous solid; $^1$H NMR (300 MHz, CDCl$_3$); 6.81 (1H, d), 6.44 (1H, d), 6.37 (1H, dd), 5.61 (1H, br s), 5.06-4.92 (1H, m), 4.18-4.04 (1H, m), 3.98 (2H, t), 3.86 (3H, s), 3.58 (2H, s), 3.46-3.36 (1H, m), 3.30-3.19 (1H, m), 2.94-2.66 (6H, m), 2.47 (2H, t), 2.35 (3H, s), 2.08-1.93 (2H, m), 1.85-1.70 (1H, m), 1.48-1.35 (1H, m), 1.34-1.00 (7H, m), 0.77 (3H, t); LC-MS: m/z 518.

Example 11

(S)-2-((3-(4-((2-amino-4-(1-hydroxyhexan-3-ylamino)-6-methylpyrimidin-5-yl)methyl)-3-methoxyphenoxy)propyl)(ethyl)amino)acetic Acid

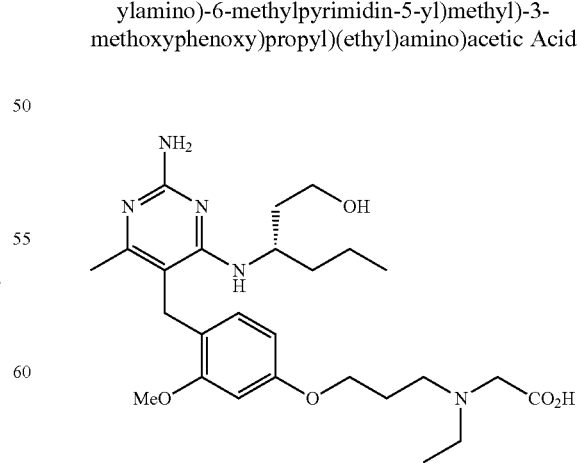

The title compound may be prepared by the steps described below:

(i) (S)-ethyl 2-((3-(4-((4-(1-acetoxyhexan-3-ylamino)-2-amino-6-methylpyrimidin-5-yl)methyl)-3-methoxyphenoxy)propyl)(ethyl)amino)acetate

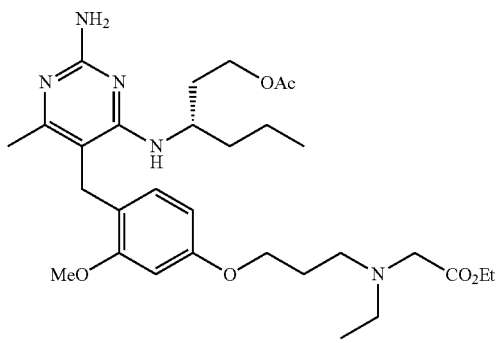 [SMILES: CCC[C@@H](CCO)Nc1nc(N)nc(C)c1Cc1ccc(OCCCN(CC)CC(=O)O)cc1OC]

The sub-title compound was synthesized by the method of example 9 step (vi) from the product of example 9 step (v) (75 mg) and the product of example 1 step (vi). The sub-title compound (60 mg) was obtained as a pale yellow oil; $^1$H NMR (300 MHz, CDCl$_3$); 6.81 (1H, d), 6.44 (1H, d), 6.38 (1H, dd), 4.95 (2H, br s), 4.28-4.05 (3H, m), 4.00-3.85 (4H, m), 3.85 (3H, s), 3.57 (2H, s), 3.32 (2H, s), 2.77-2.62 (4H, m), 2.36 (3H, s), 1.97 (3H, s), 1.95-1.72 (3H, m), 1.63-1.50 (1H, m), 1.48-1.33 (1H, m), 1.30-1.15 (2H, m), 1.24 (3H, t), 1.11-0.98 (2H, m), 1.03 (3H, t), 0.77 (3H, t); LC-MS: m/z 574.

(ii) (S)-2-((3-(4-((2-amino-4-(1-hydroxyhexan-3-ylamino)-6-methylpyrimidin-5-yl)methyl)-3-methoxyphenoxy)propyl)(ethyl)amino)acetic Acid

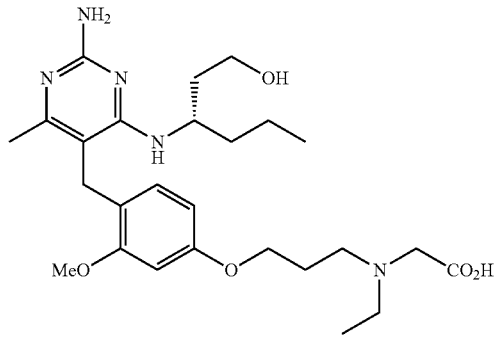 [SMILES: CCC[C@@H](CCO)Nc1nc(N)nc(C)c1Cc1ccc(OCCCN(CC)CC(=O)O)cc1OC]

The sub-title compound was synthesized by the method of example 9 step (vii) from the product of step (i) (52 mg). The sub-title compound (44 mg) was obtained as a white amorphous solid; $^1$H NMR (300 MHz, CDCl$_3$); 6.90-6.60 (1H, m), 6.79 (1H, d), 6.47 (1H, d), 6.40 (1H, dd), 5.40 (1H, d), 4.20-4.07 (1H, m), 4.03 (2H, t), 3.85 (3H, s), 3.55 (2H, s), 3.40-3.30 (1H, m), 3.32 (2H, s), 3.24-3.14 (1H, m), 3.02-2.87 (4H, m), 2.37 (3H, s), 2.10-1.98 (2H, m), 1.85-1.70 (1H, m), 1.49-1.36 (1H, m), 1.34-0.98 (7H, m), 0.78 (3H, t); LC-MS: m/z 504.

Example 12

(S)-2-((3-(4-((2-amino-4-(1-hydroxyhexan-3-ylamino)-6-methylpyrimidin-5-yl)methyl)-3-methoxyphenoxy)propyl)(2,2-difluoroethyl)amino) acetic Acid

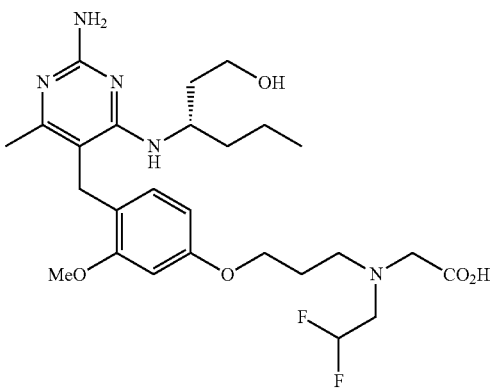 [SMILES: CCC[C@@H](CCO)Nc1nc(N)nc(C)c1Cc1ccc(OCCCN(CC(=O)O)CC(F)F)cc1OC]

The title compound may be prepared by the steps described below:

(i) (S)-ethyl 2-((3-(4-((4-(1-acetoxyhexan-3-ylamino)-2-amino-6-methylpyrimidin-5-yl)methyl)-3-methoxyphenoxy)propyl)(2,2-difluoroethyl)amino)acetate

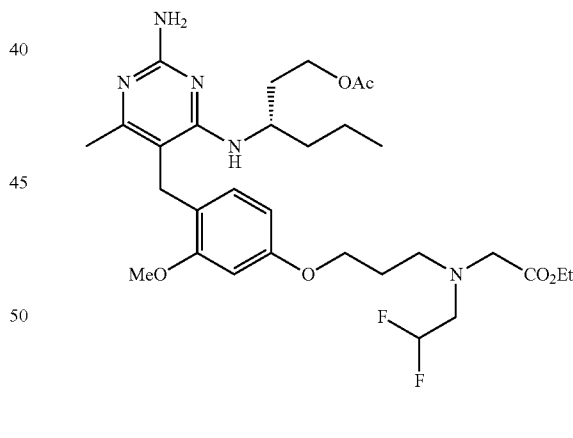

The sub-title compound was synthesized by the method of example 9 step (vi) from the product of example 9 step (v) (75 mg) and the product of example 3 step (i) (112 mg). The sub-title compound (44 mg) was obtained as a pale yellow oil; $^1$H NMR (300 MHz, CDCl$_3$); 6.81 (1H, d), 6.44 (1H, d), 6.37 (1H, dd), 5.77 (1H, tt), 4.97 (2H, br s), 4.28-4.09 (3H, m), 4.00-3.85 (4H, m), 3.86 (3H, s), 3.58 (2H, s), 3.45 (2H, s), 3.11-2.86 (4H, m), 2.36 (3H, s), 1.97 (3H, s), 1.95-1.74 (3H, m), 1.63-1.50 (1H, m), 1.46-1.33 (1H, m), 1.30-1.15 (5H, m), 1.12-0.98 (2H, m), 0.77 (3H, t); LC-MS: m/z 610.

(ii) (S)-2-((3-(4-((2-amino-4-(1-hydroxyhexan-3-ylamino)-6-methylpyrimidin-5-yl)methyl)-3-methoxyphenoxy)propyl)(2,2-difluoroethyl)amino)acetic Acid

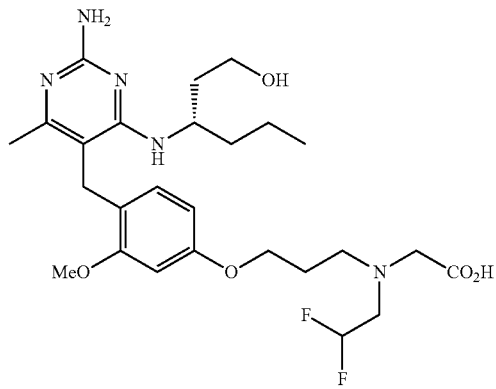 [SMILES: CCC[C@@H](CCO)Nc1nc(N)nc(C)c1Cc1ccc(OCCCN(CC(=O)O)CC(F)F)cc1OC]

The sub-title compound was synthesized by the method of example 9 step (vii) from the product of step (i) (44 mg). The sub-title compound (38 mg) was obtained as a white amorphous solid; $^1$H NMR (300 MHz, CDCl$_3$); 6.80 (1H, d), 6.48-6.40 (2H, m), 5.89 (1H, tt), 5.89-5.73 (1H, m), 4.28-4.13 (1H, m), 4.07-3.97 (2H, m), 3.86 (3H, s), 3.63-3.56 (1H, m), 3.56 (2H, s), 3.40-3.30 (1H, m), 3.33 (2H, s), 3.17-2.85 (5H, m), 2.44 (3H, s), 1.96-1.85 (2H, m), 1.85-1.71 (1H, m), 1.52-1.39 (1H, m), 1.39-1.00 (4H, m), 0.81 (3H, t); LC-MS: m/z 540.

Example 13

(R)-1-(4-((2-amino-4-((S)-1-hydroxyhexan-3-ylamino)-6-methylpyrimidin-5-yl)methyl)-3-methoxybenzyl)pyrrolidine-2-carboxylic Acid

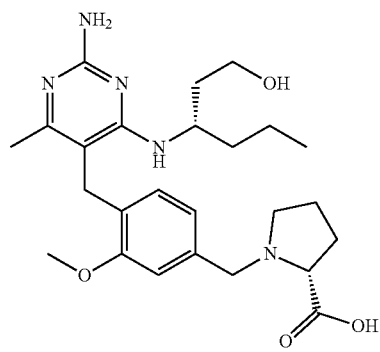 [SMILES: CCC[C@@H](CCO)Nc1nc(N)nc(C)c1Cc1ccc(CN2CCC[C@@H]2C(=O)O)cc1OC]

The title compound was prepared by the sequence of steps described below:

(i) (R)-tert-butyl 1-(4-((2-amino-4-(mesitylsulfonyloxy)-6-methylpyrimidin-5-yl)methyl)-3-methoxybenzyl)pyrrolidine-2-carboxylate

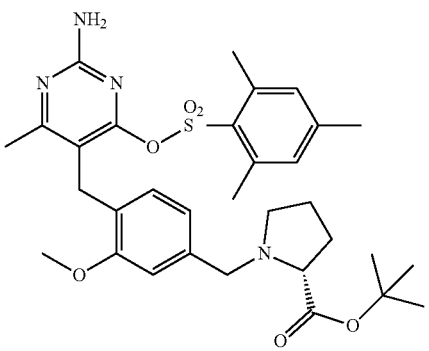 [SMILES: COc1cc(CN2CCC[C@@H]2C(=O)OC(C)(C)C)ccc1Cc1c(C)nc(N)nc1OS(=O)(=O)c1c(C)cc(C)cc1C]

The sub-title compound was synthesized by the method of example 1 step (vii) from the product of example 1 step (v) (200 mg) and (R)-tert-butyl pyrrolidine-2-carboxylate (108 mg). The sub-title compound (234 mg) was obtained as a colourless amorphous solid; LC-MS: m/z 611.

(ii) (R)-tert-butyl 1-(4-((2-amino-4-((S)-1-hydroxyhexan-3-ylamino)-6-methylpyrimidin-5-yl)methyl)-3-methoxybenzyl)pyrrolidine-2-carboxylate

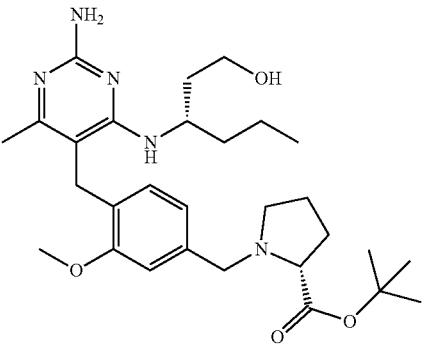 [SMILES: CCC[C@@H](CCO)Nc1nc(N)nc(C)c1Cc1ccc(CN2CCC[C@@H]2C(=O)OC(C)(C)C)cc1OC]

The sub-title compound was synthesized by the method of example 1 step (viii) from the product of step (i) (234 mg) and (S)-3-aminohexan-1-ol (X mg). The sub-title compound (70 mg) was obtained as a colourless amorphous solid; LC-MS: m/z 528.

(iii) (R)-1-(4-((2-amino-4-((S)-1-hydroxyhexan-3-ylamino)-6-methylpyrimidin-5-yl)methyl)-3-methoxybenzyl)pyrrolidine-2-carboxylic Acid

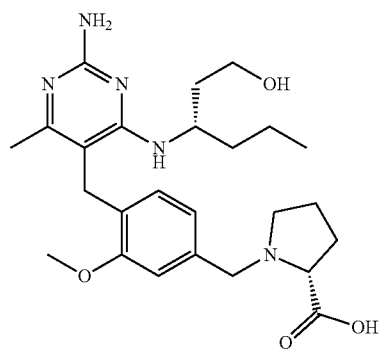 [SMILES: CCC[C@@H](CCO)Nc1nc(N)nc(C)c1Cc1ccc(CN2CCC[C@@H]2C(=O)O)cc1OC]

To a solution of the product of step (ii) (70 mg) in chloroform (1.5 mL) was added trifluoroacetic acid (1.5 mL) and the mixture was stirred at RT. After 12 h, methanol (10 mL) was stirred at room temperature. After 12 h, the mixture was concentrated under reduced pressure. 10% aqueous potassium dicarbonate was added and the resulting mixture was extracted with chloroform/EtOH (3/1). The combined organic layer was dried and concentrated under reduced pressure to afford the sub-title compound (50 mg) as a white solid; $^1$H NMR (methanol-d4); 7.23 (1H, d), 7.02-6.97 (2H, m), 4.47 (1H, m), 4.34 (2H, s), 3.97 (3H, s), 3.85-3.80 (3H, m), 3.64 (1H, m), 3.45-3.41 (2H, m), 2.44 (1H, m), 2.28 (3H, s), 2.11 (2H, m), 1.96 (1H, m), 1.74-1.20 (7H, m), 0.87 (3H, t); LC-MS: m/z 472.

Example 14

(S)-1-(4-((2-amino-4-(1-hydroxyhexan-3-ylamino)-6-methylpyrimidin-5-yl)methyl)-3-methoxybenzyl)-1H-imidazole-5-carboxylic Acid

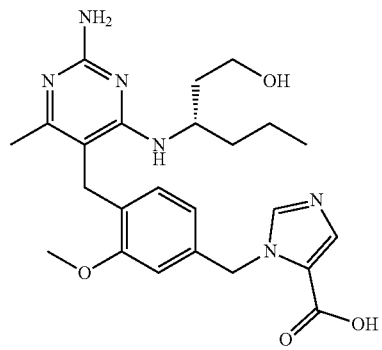 [SMILES: CCC[C@@H](CCO)Nc1nc(N)nc(C)c1Cc1ccc(Cn2cncc2C(=O)O)cc1OC]

The title compound was prepared by the sequence of steps described below:

(i) methyl 1-(4-((2-amino-4-(mesitylenesulfonyloxy)-6-methylpyrimidin-5-yl)methyl)-3-methoxybenzyl)-1H-imidazole-5-carboxylate

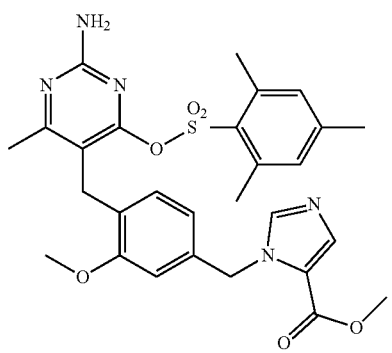

The sub-title compound was synthesized by the method of example 1 step (vii) from the product of example 1 step (v) (500 mg) and Methyl 1H-imidazole-5-carboxylate (199 mg). The sub-title compound (90 mg) was obtained as a white solid; 1H NMR (300 MHz, CDCl$_3$); 7.73 (1H, s), 7.61 (1H, s), 6.89 (2H, s), 6.83 (1H, d), 6.61 (1H, s), 6.55 (1H, d), 5.42 (2H, s), 3.78 (3H, s), 3.68 (5H, s), 2.46 (3H, s), 2.42 (6H, s), 2.26 (3H, s); LC-MS: m/z 566.

(ii) (S)-methyl 1-(4-((2-amino-4-(1-hydroxyhexan-3-ylamino)-6-methylpyrimidin-5-yl)methyl)-3-methoxybenzyl)-1H-imidazole-5-carboxylate

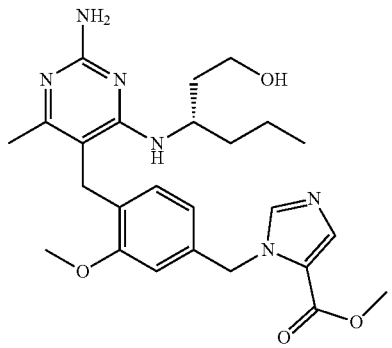

The sub-title compound was synthesized by the method of example 1 step (viii) from the product of step (i) (90 mg) and (S)-3-aminohexan-1-ol (56 mg). The sub-title compound (53 mg) was obtained as a colourless oil; LC-MS: m/z 483.

(iii) (S)-1-(4-((2-amino-4-(1-hydroxyhexan-3-ylamino)-6-methylpyrimidin-5-yl)methyl)-3-methoxybenzyl)-1H-imidazole-5-carboxylic Acid

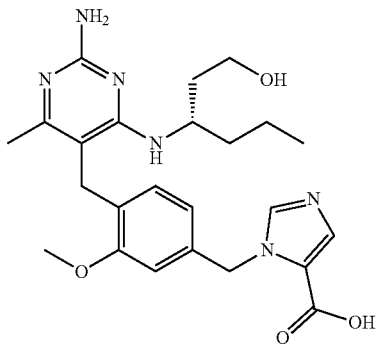 [SMILES: CCC[C@@H](CCO)Nc1nc(N)nc(C)c1Cc1ccc(Cn2cncc2C(=O)O)cc1OC]

The sub-title compound was synthesized by the method of example 1 step (ix) from the product of step (ii) (53 mg). The sub-title compound (16 mg) was obtained as a colourless amorphous solid; LC-MS: m/z 469.

Example 15: Alternative Procedure for (S)-2-((4-((2-amino-4-(1-hydroxyhexan-3-ylamino)-6-methylpyrimidin-5-yl)methyl)-3-methoxybenzyl)(2,2-difluoroethyl)amino)acetic Acid

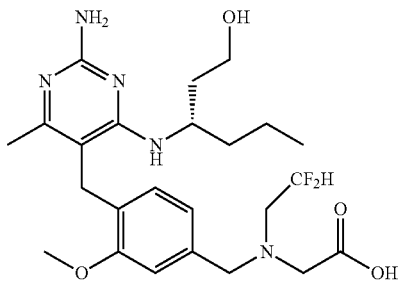 [SMILES: CCC[C@@H](CCO)Nc1nc(N)nc(C)c1Cc1ccc(CN(CC(=O)O)CC(F)F)cc1OC]

The title compound was prepared by the sequence of steps described below:

(i) tert-butyl 2-(2,2-difluoroethylamino)acetate

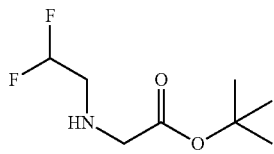

tert-Butyl bromoacetate (2.72 g) was added to a suspension of 2,2-difluoroethylamine (1.46 g) and potassium carbonate (2.48 g) in acetonitrile (5 mL) and the mixture was stirred at RT for 24 h. The mixture was diluted with EtOAc (10 mL) and hexane (10 mL). The suspension was washed with the mixture of aqueous NaHCO$_3$ (20 mL) and brine (10 mL). The organic extracts were dried and concentrated in vacuo to provide crude product. The crude product was purified by vacuum distillation (12 hPa, 78-80° C.) to afford sub-title compound (1.85 g) as a colourless oil; 1H NMR (300 MHz, CDCl$_3$); 5.82 (1H, tt, J=4.4, 56 Hz), 3.45 (2H, s), 2.98 (2H, dt, J=4.4, 15.1 Hz), 1.45 (9H, s).

(ii) 2-Amino-5-(4-chloromethyl-2-methoxybenzyl)-6-methylpyrimidin-4-yl 2,4,6-triisopropylbenzenesulfonate

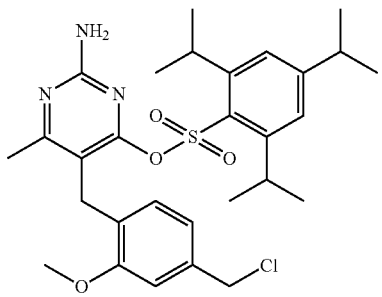 [SMILES: COc1cc(CCl)ccc1Cc1c(C)nc(N)nc1OS(=O)(=O)c1c(C(C)C)cc(C(C)C)cc1C(C)C]

To a solution of 2-amino-5-(4-hydroxymethyl-2-methoxybenzyl)-6-methylpyrimidin-4-ol (5.0 g) and N,N-diisopropylethylamine (11.7 g) in tetrahydrofuran (50 g), 2,4,6-triisopropylbenzenesulfonyl chloride (8.3 g) was added and refluxed for 10 h. After cooling to RT, lithium chloride (2.3 g) was added to the reaction mixture and stirred for 0.5 h, methanesulfonyl chloride (4.2 g) was added over 0.25 h dropwise and the reaction mixture was stirred for 4 h at RT. To the reaction mixture, water (25 g) was added and extracted with ethyl acetate (25 g). The organic layer was washed with water (25 mL) and concentrated in vacuo. To the residue, toluene (20 g) was added and concentrated on vacuo to obtain a light brown solid. The solid was precipitated with toluene (30 g) to obtain sub-title compound (6.8 g). 1H-NMR (300 MHz, CDCl$_3$) δ 7.17 (2H, s), 6.90-6.82 (3H, m), 5.16 (2H, brs), 4.55 (2H, s), 4.10 (2H, septet, J=6.8 Hz), 3.82 (3H, s), 3.81 (2H, s), 2.91 (1H, septet, J=6.8 Hz), 2.32 (3H, s), 1.25 (6H, d, J=7.2 Hz), 1.19 (12H, d, J=6.8 Hz)

(iii) tert-butyl 2-((4-((2-amino-4-methyl-6-(2,4,6-triisopropylphenylsulfonyloxy)pyrimidin-5-yl)methyl)-3-methoxybenzyl)(2,2-difluoroethyl)amino)acetate

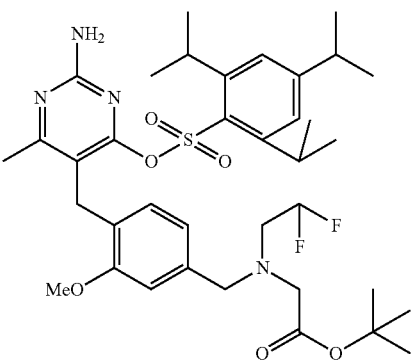 [SMILES: COc1cc(CN(CC(=O)OC(C)(C)C)CC(F)F)ccc1Cc1c(C)nc(N)nc1OS(=O)(=O)c1c(C(C)C)cc(C(C)C)cc1C(C)C]

The mixture of the product of step (i) (209 mg), step (ii) (500 mg), sodium carbonate (283 mg) and potassium iodide (44 mg) in acetonitrile (4.0 g) was refluxed for 7 h. After cooling to RT, water (7.5 mL) was added to the mixture and extracted with mixture of EtOAc (10 mL) and n-heptane (4 mL). The organic layer was dried with Na₂SO₄ and concentrated in vacuo. The residue was precipitated with n-heptane (18 g) to afford sub-title compound (537 mg).

¹H-NMR (300 MHz, CDCl₃) δ 7.24 (2H, s), 6.83 (1H, s), 6.78 (1H, d, J=7.6 Hz), 6.71 (1H, dd, J=7.6 Hz, 1.2 Hz), 5.74 (1H, tt, J=4.4, 56 Hz), 4.73 (2H, brs), 4.17-4.08 (2H, m), 3.85 (2H, s), 3.80-3.77 (5H, m), 3.33 (2H, s), 3.04 (2H, dt, J=4.4, Hz), 2.93-2.85 (1H, m), 2.23 (3H, s), 1.45 (9H, s), 1.18 (6H, d, J=6.8 Hz), 1.12 (12H, d, J=6.8 Hz)

(iv) (S)-tert-butyl 2-((4-((2-amino-4-(1-hydroxy-hexan-3-ylamino)-6-methylpyrimidin-5-yl)methyl)-3-methoxybenzyl)(2,2-difluoroethyl)amino)acetate

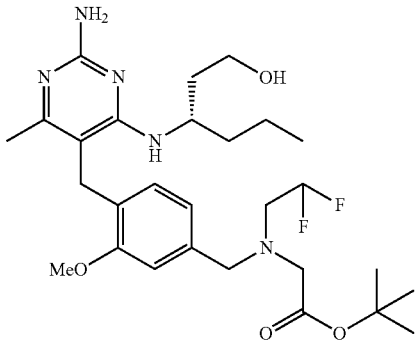 [SMILES: CCC[C@@H](CCO)Nc1nc(N)nc(C)c1Cc1ccc(CN(CC(=O)OC(C)(C)C)CC(F)F)cc1OC]

The mixture of the product of step (iii) (300 mg), (S)-3-amino-1-hexanol (98 mg) and trifluoro acetic acid (24 mg) in mono-chlorobenzene (1.5 mL) was refluxed for 8 h. The mixture was cooled to RT and diluted with toluene (4 mL) and THF (1 mL). The mixture was washed with 0.5% aqueous LiOH (10 mL) for three times and brine (5 mL). The organic layer was dried, concentrated in vacuo and purified by flash column chromatography on silica gel to afford the sub-title compound (210 mg) as a colourless oil. 1H NMR (300 MHz, CD₃Cl₃); 6.91-6.76 (2H, m), 6.78 (1H, d, J=7.6 Hz), 5.73 (1H, tt, J=4.4, 56 Hz), 4.87 (1H, brs), 4.69 (2H, brs), 4.15-4.05 (1H, m), 3.88 (3H, s), 3.85 (2H, s), 3.66 (1H, s), 3.48-3.42 (2H, m), 3.30-3.07 (3H, m), 3.03 (2H, dt, J=4.4, 15 Hz), 2.35 (3H, s), 1.83-1.75 (1H, m), 1.43-0.99 (15H, m), 0.74 (3H, t, J=7.6 Hz).

(v) (S)-2-((4-((2-amino-4-(1-hydroxyhexan-3-ylamino)-6-methylpyrimidin-5-yl)methyl)-3-methoxybenzyl)(2,2-difluoroethyl)amino)acetic Acid The mixture of the product of step (iv) (13 mg) in 3N HCl (1 mL) was stirred at 50° C. for 1.5 h. The mixture was cooled to RT and pH of the mixture was adjusted between pH 5 and pH 6 with 1N aqueous NaOH. The mixture was extracted with ethanol/chloroform (1/3) and the organic layer was dried and concentrated in vacuo to afford the sub-title compound (12 mg) as a colourless powder.

Example 16: Alternative Procedure of (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic Acid

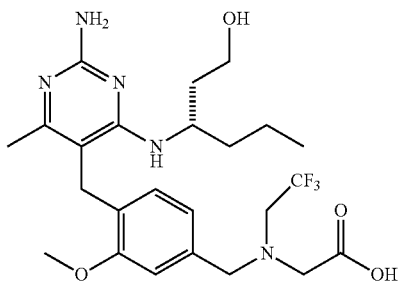 [SMILES: CCC[C@@H](CCO)Nc1nc(N)nc(C)c1Cc1ccc(CN(CC(=O)O)CC(F)(F)F)cc1OC]

The title compound was prepared by the sequence of steps described below:

(i) tert-butyl 2-(2,2,2-trifluoroethylamino)acetate

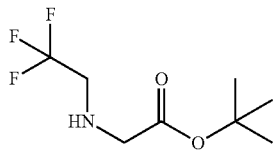

The subtitled compound was synthesized by the method of example 15 step (i) from tert-butyl bromoacetate (13.6 g) and 2,2,2-trifluoroethylamine (8.9 g). The sub-title compound (11 g) was obtained as a colourless oil; 1H NMR (300 MHz, CDCl₃); 3.39 (2H, s), 3.20 (2H, q, J=9.4 Hz), 1.44 (9H, S).

(ii) tert-butyl 2-((4-bromo-3-methoxybenzyl)(2,2,2-trifluoroethyl)amino)acetate

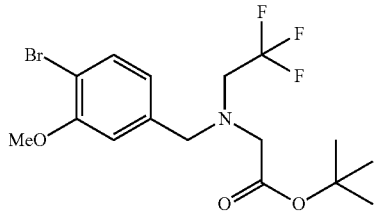 [SMILES: COc1cc(CN(CC(=O)OC(C)(C)C)CC(F)(F)F)ccc1Br]

The mixture of 1-bromo-4-(bromomethyl)-2-methoxybenzene (200 mg), the product of step (i) (228 mg), potassium carbonate (179 mg) and potassium iodide (35 mg) in N,N-dimethylacetamide (2 mL) was stirred at 75° C. for 2 h. The mixture was diluted with EtOAc (10 mL) and the mixture was washed with water (10 mL) and brine (10 mL). The organic layer was dried, concentrated in vacuo and purified by flash column chromatography on silica gel to afford the sub-title compound (166 mg) as a colourless oil; 1H NMR (300 MHz, DMSO-d₆); 7.51 (1H, d, J=8.0 Hz), 7.12 (1H, d, J=1.6 Hz), 6.82 (1H, dd, J=1.6, 8.0 Hz), 3.89 (2H, s), 3.81 (3H, s), 3.50 (2H, q, J=10 Hz), 3.35 (2H, s), 1.41 (9H, s).

(iii) methyl 2-(4-(((2-tert-butoxy-2-oxoethyl)(2,2,2-trifluoroethyl)amino)methyl)-2-methoxybenzyl)-3-oxobutanoate

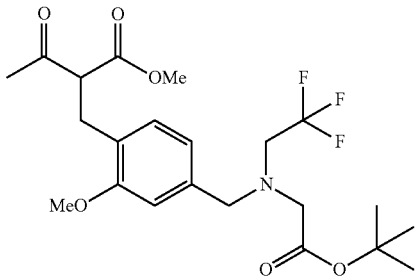 [SMILES: COC(=O)C(Cc1ccc(CN(CC(=O)OC(C)(C)C)CC(F)(F)F)cc1OC)C(C)=O]

The mixture of the product of step (ii) (110 mg), methyl 3-hydroxy-2-methylenebutanoate (70 mg), N-methyldicyclohexylamine (105 mg), tetrabutylammonium chloride (8 mg) and 1,1'-bis(di-tert-butylphosphino)ferrocene palladium dichloride (19 mg) in N,N-dimethylacetamide (1 mL) was stirred at 100° C. for 8 h. The mixture was diluted with EtOAc (10 mL) and washed with aqueous NaHCO$_3$ (10 mL). The organic layer was dried, concentrated in vacuo and purified by flash column chromatography on silica gel to afford the sub-title compound (81 mg) as a colourless oil; 1H NMR (300 MHz, DMSO-d$_6$); 7.01 (1H, d, J=7.6 Hz), 6.86 (1H, s), 6.75 (1H, d, J=7.6 Hz), 3.91-3.84 (3H, m), 3.75 (3H, s), 3.57 (3H, s), 3.48 (2H, q, J=10 Hz), 3.04-2.89 (2H, m), 2.13 (3H, s), 1.42 (9H, s). MS:APCI 462 (M+1).

(iv) tert-butyl 2-((4-((2-amino-4-hydroxy-6-methylpyrimidin-5-yl)methyl)-3-methoxybenzyl)(2,2,2-trifluoroethyl)amino)acetate

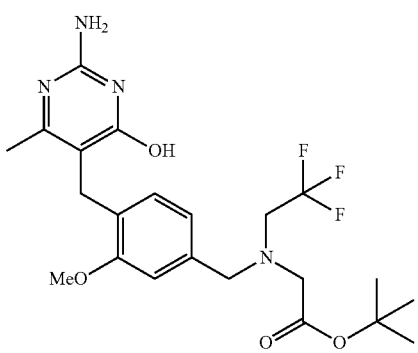 [SMILES: COc1cc(CN(CC(=O)OC(C)(C)C)CC(F)(F)F)ccc1Cc1c(C)nc(N)nc1O]

The mixture of the product of step (iii) (75 mg) and guanidine carbonate (50 mg) in MeOH (1 mL) was stirred at 65° C. for 12 h. The mixture was cooled to RT and pH of the mixture was adjusted around pH8 with acetic acid and stirred for 0.5 h. The residue was filtered and the filtrate was purified by flash column chromatography on silica gel to afford the sub-title compound (35 mg) as a colourless powder; 1H NMR (300 MHz, DMSO-d$_6$); 10.71 (1H, s), 6.87-6.84 (1H, m), 6.79-6.77 (1H, m), 6.71-6.68 (1H, m), 6.28 (2H, s), 3.85 (2H, s), 3.78 (3H, s), 3.52-3.45 (4H, m), 1.92 (3H, s), 1.41 (9H, S).

(v) tert-butyl 2-((4-((2-amino-4-methyl-6-(2,4,6-triisopropylphenylsulfonyloxy)pyrimidin-5-yl)methyl)-3-methoxybenzyl)(2,2,2-trifluoroethyl)amino)acetate

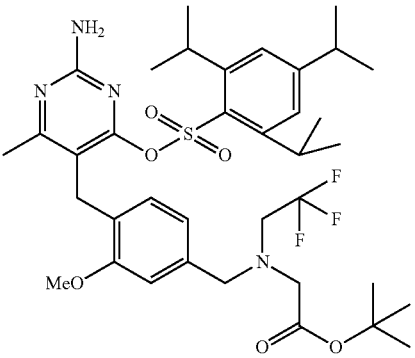 [SMILES: COc1cc(CN(CC(=O)OC(C)(C)C)CC(F)(F)F)ccc1Cc1c(C)nc(N)nc1OS(=O)(=O)c1c(C(C)C)cc(C(C)C)cc1C(C)C]

The mixture of the product of step (iv) (28 mg), 2,4,6-triisopropylbenzenesulfonylchloride (30 mg) and DABCO (5.5 mg) in THF (1 mL) was stirred at 40° C. for 3 hours. The mixture was cooled to RT and diluted with EtOAc (10 mL). The mixture was washed with aqueous NaHCO$_3$ (10 mL). The organic layer was dried, concentrated in vacuo and purified by flash column chromatography on silica gel to afford the sub-title compound (28 mg) as a colourless oil; 1H-NMR (300 MHz, CDCl$_3$) 7.16 (2H, s), 6.88 (1H, d, J=1.2 Hz), 6.79 (1H, d, J=7.6 Hz), 6.71 (1H, dd, J=7.6 Hz, 1.2 Hz), 4.73 (2H, brs), 4.15 (2H, septet, J=6.8 Hz), 3.92 (2H, s), 3.82 (2H, s), 3.80 (3H, s), 3.39-3.32 (4H, m), 2.91 (1H, septet, J=7.2 Hz), 2.25 (3H, s), 1.47 (9H, s), 1.25 (6H, d, J=6.8 Hz), 1.19 (12H, d, J=6.4 Hz)

(vi) (S)-tert-butyl 2-((4-((2-amino-4-(1-hydroxyhexan-3-ylamino)-6-methylpyrimidin-5-yl)methyl)-3-methoxybenzyl)(2,2,2-trifluoroethyl)amino)acetate

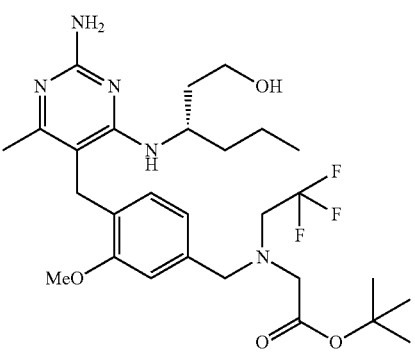 [SMILES: CCC[C@@H](CCO)Nc1nc(N)nc(C)c1Cc1ccc(CN(CC(=O)OC(C)(C)C)CC(F)(F)F)cc1OC]

The sub-title compound was synthesized by the method of example 15 step (iv) from the product of Example 16 step (v) (25 mg). The sub-title compound (12 mg) was obtained as a colourless oil; 1H NMR (300 MHz, CD$_3$OD); 7.01 (1H, s), 6.87-6.85 (1H, m), 6.81-6.78 (1H, m), 4.23-4.20 (1H, m), 3.92 (2H, s), 3.90 (3H, s), 3.72 (2H, s), 3.44-3.30 (6H, m), 2.24 (3H, s), 1.85-1.70 (1H, m), 1.46-1.30 (13H, m), 1.23-1.08 (2H, m), 0.81-0.77 (3H, m).

(vii) (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic Acid

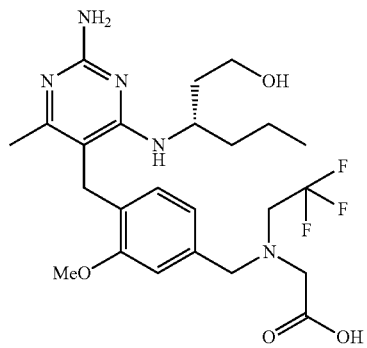 [SMILES: CCC[C@@H](CCO)Nc1nc(N)nc(C)c1Cc1ccc(CN(CC(=O)O)CC(F)(F)F)cc1OC]

The sub-title compound was synthesized by the method of example 15 step (v) from the product of step (vi) (12 mg). The sub-title compound (11 mg) was obtained as a colourless powder.

Example 17: Alternative Procedure for tert-butyl 2-((4-((2-amino-4-methyl-6-(2,4,6-triisopropylphenylsulfonyloxy)pyrimidin-5-yl)methyl)-3-methoxybenzyl)(2,2,2-trifluoroethyl)amino)acetate

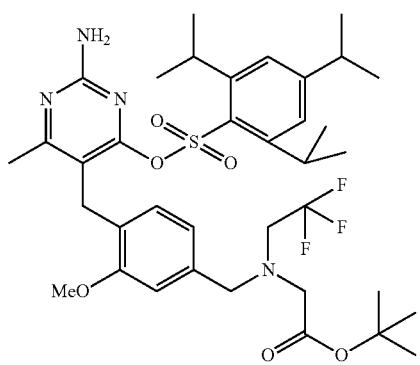 [SMILES: COc1cc(CN(CC(=O)OC(C)(C)C)CC(F)(F)F)ccc1Cc1c(C)nc(N)nc1OS(=O)(=O)c1c(C(C)C)cc(C(C)C)cc1C(C)C]

The mixture of 2-amino-5-(4-chloromethyl-2-methoxybenzyl)-6-methylpyrimidin-4-yl 2,4,6-triisopropylbenzenesulfonate (6.0 g), tert-butyl 2-(2,2,2-trifluoroethylamino)acetate (2.7 g), sodium carbonate (3.4 g) and potassium iodide (0.5 g) in acetonitrile (48 g) was refluxed for 8 h. After cooling to RT, water (30 g) was added to the mixture and extracted with toluene (48 g). The organic layer was washed with water (30 g) and concentrated in vacuo. The residue was precipitated with n-heptane (18 g) to afford the sub-title compound (12.2 g).

Example 18: Preparation of the form B of the Compound of Example 3

To a solution of the product of example 3 step (iii) (1.38 g) in MeOH (12.5 mL), 3 M NaOH aq. (4.2 mL) was added. The mixture was stirred for 3 h at room temperature, and neutralized with 4 M HCl aq. (5.0 mL) and sat. NaHCO$_3$ aq. (5.0 mL). The resulting suspension was concentrated to about half in volume. Then, the precipitation crystals were filtered and washed with cooled water (15 mL). After vacuum drying, Form B of example 3 (1.0 g) was obtained as a white solid.

Example 19: Preparation of the form A of the Compound of Example 3

The compound of Example 18 (45 mg) was mixed with water (1 mL) and acetone (0.2 mL) and stirred at 60° C. for 1 hr. Then water (0.5 mL) was added, and the mixture was cooled to ambient temperature. After 1 h, the precipitation crystals were filtered. After vacuum drying Form A of example 3 (38 mg) was obtained as a white solid.

Example 20: Preparation of the form E of the Compound of Example 3

The compound of Example 19 (5 mg) was dissolved by EtOH (50 ml) at 90° C. The solution was cooled to ambient temperature. After 1 h, the precipitation crystals were filtered and put in 93% RH condition for 3 days. Form E of example 3 (2 mg) was obtained as a white solid.

Example 21: Preparation of the form A of the Compound of Example 4

3N—NaOH (0.5 mL) was added to the solution of the product of example 4 step (iii) (170 mg) in MeOH (2 mL). The solution was stirred at room temperature for 1.5 h. The reaction mixture was acidified with 2N—HCl (1.4 mL), neutralized with saturated aqueous NaHCO$_3$ (0.3 mL) and extracted with CHCl$_3$/EtOH (v/v=3/1). The combined organic layer was dried over Na$_2$SO$_4$, filtered and concentrated under reduced pressure. EtOAc (20 mL) was added to the residue and sonicated. The mixture was stirred under reflux condition for 5 min then cooled to room temperature. The suspension was stirred at room temperature for 30 min. The precipitate was collected by filtration. Form A of compound example 4 (143 mg) was obtained as a white solid.

Example 22: Differential Scanning Calorimetry (DSC) of the Compound Obtained in Example 18-21

The calorimetric response of the test sample to increasing temperature was investigated using a TA Instruments Q1000 Differential Scanning Calorimeter (DSC). Measurements were performed from 10 to 250° C. with a ramp rate of 10° C. per minute. Approximately 0.5 to 5 mg of the test sample was placed in an aluminum pan with lid (crimped and pinholed) under a flow of nitrogen gas (50 mL/min).

The result is shown in FIG. 1-4. An endothermic peak and an exothermic peak appeared from 260° C.

Example 23: X-Ray Powder Diffraction Analyses of the Compound Obtained in Example 18-21

Panalytical X'pert Alpha 1 system with monochromatic CuKα radiation (45 kV and 40 mA) was used for the analysis. The primary optics contained metal mask and an automatic divergence slit. Flat samples were prepared on the zero background plates that were rotated during the measurements. The secondary optics contained soller slits, an automatic anti scatter slit and a monochromator. The diffracted signal was detected with a detector (X'Celerator).

Diffraction patterns were collected at 4°≤2θ (theta)≤30-40° in a continuous scan mode with 100-second exposure per 0.017°. Raw data were stored electronically.

The results are shown in FIG. 5-8 and Table 1-4

TABLE 1

XRD data of Example 18(From B)

| Pos. [°2θ] | d-spacing [Å] | relative intensity [%] |
|---|---|---|
| 6.5405 | 13.50317 | 100 |
| 9.5427 | 9.26071 | 6.19 |
| 10.1255 | 8.72892 | 75.35 |
| 10.9117 | 8.10168 | 58.65 |
| 13.0489 | 6.77919 | 10.92 |
| 13.9263 | 6.35398 | 16.1 |
| 15.2431 | 5.80793 | 15.96 |
| 16.4823 | 5.37392 | 8 |
| 16.777 | 5.28021 | 24.4 |
| 17.0169 | 5.2063 | 17.93 |
| 17.5125 | 5.06006 | 11.74 |
| 17.9973 | 4.92482 | 15.27 |
| 18.3734 | 4.82485 | 13.12 |
| 18.6586 | 4.75175 | 10.63 |
| 19.2222 | 4.61369 | 43.79 |
| 19.5965 | 4.52639 | 11.33 |
| 20.0458 | 4.42594 | 9.6 |
| 20.4279 | 4.34401 | 10.49 |
| 20.8812 | 4.25072 | 32.04 |
| 22.1453 | 4.01086 | 14.91 |
| 22.8051 | 3.89628 | 7.87 |
| 23.637 | 3.761 | 55.76 |
| 24.2084 | 3.67352 | 12.39 |
| 25.1576 | 3.53702 | 13.37 |
| 25.6668 | 3.46799 | 15.53 |
| 25.9557 | 3.43004 | 27.97 |
| 26.5107 | 3.35948 | 14.07 |
| 27.4235 | 3.24969 | 17.76 |
| 30.814 | 2.89941 | 5.88 |

TABLE 2

XRD data of Example 19 (Form A).

| Pos. [°2θ] | d-spacing [Å] | relative intensity [%] |
|---|---|---|
| 7.8835 | 11.20558 | 38.83 |
| 10.9385 | 8.08194 | 45.5 |
| 12.3678 | 7.15094 | 68.29 |
| 13.1016 | 6.75202 | 14.38 |
| 14.6608 | 6.03724 | 17.09 |
| 15.7499 | 5.62214 | 25.46 |
| 16.0343 | 5.52306 | 10.08 |
| 16.3252 | 5.4253 | 14.29 |
| 16.9925 | 5.21372 | 49.92 |
| 17.763 | 4.98927 | 43.88 |
| 18.3066 | 4.84233 | 10.49 |
| 18.588 | 4.76965 | 40.3 |
| 19.1668 | 4.62689 | 32.82 |
| 19.6059 | 4.52424 | 20.27 |
| 20.9633 | 4.23426 | 100 |
| 21.5335 | 4.12342 | 12.96 |
| 21.937 | 4.04846 | 31.4 |
| 22.5622 | 3.93768 | 20.21 |
| 23.3569 | 3.80547 | 19.35 |
| 23.8257 | 3.73164 | 44.83 |
| 24.4437 | 3.63867 | 57.1 |
| 25.787 | 3.45209 | 41.09 |
| 27.3243 | 3.26126 | 10.13 |
| 28.8489 | 3.09229 | 10.23 |
| 29.8528 | 2.99055 | 19.07 |
| 30.9551 | 2.88652 | 13.15 |
| 31.2064 | 2.86385 | 11.54 |
| 31.7293 | 2.81783 | 10.8 |

TABLE 2-continued

XRD data of Example 19 (Form A).

| Pos. [°2θ] | d-spacing [Å] | relative intensity [%] |
|---|---|---|
| 31.9519 | 2.79871 | 15.59 |
| 37.4073 | 2.40213 | 10.72 |

TABLE 3

XRD data of Example 20 (Form E)

| Pos. [°2θ] | d-spacing [Å] | relative intensity [%] |
|---|---|---|
| 8.1575 | 10.82981 | 100 |
| 11.2091 | 7.88743 | 5.81 |
| 11.5525 | 7.65373 | 6.57 |
| 11.9207 | 7.41815 | 26.96 |
| 12.8753 | 6.87017 | 48.08 |
| 14.6921 | 6.02448 | 9.64 |
| 15.0144 | 5.89585 | 5.33 |
| 15.5873 | 5.68043 | 8.02 |
| 15.8084 | 5.60147 | 8.22 |
| 16.3069 | 5.43135 | 12.71 |
| 17.4032 | 5.09159 | 7.27 |
| 18.2706 | 4.85179 | 16.74 |
| 19.2195 | 4.61433 | 5.18 |
| 19.853 | 4.4685 | 10.6 |
| 20.0704 | 4.42058 | 11.12 |
| 20.8876 | 4.24944 | 10.7 |
| 21.3279 | 4.16269 | 10.49 |
| 21.8003 | 4.07355 | 7.31 |
| 22.0481 | 4.02832 | 5.39 |
| 22.7843 | 3.89979 | 20.23 |
| 23.1742 | 3.83505 | 9.78 |
| 23.9179 | 3.71747 | 18.89 |
| 24.5882 | 3.61762 | 11.8 |
| 24.9957 | 3.55956 | 27.96 |
| 25.402 | 3.50353 | 13.89 |
| 25.9936 | 3.42513 | 6.99 |

TABLE 4

XRD data of Example 21 (Form A)

| Pos. [°2θ] | d-spacing [Å] | relative intensity [%] |
|---|---|---|
| 7.8637 | 11.23377 | 16.54 |
| 10.9314 | 8.08713 | 71.64 |
| 12.2995 | 7.1905 | 69.75 |
| 13.0374 | 6.78512 | 15.64 |
| 14.6241 | 6.05231 | 9.45 |
| 15.7034 | 5.63871 | 44.31 |
| 16.2899 | 5.43698 | 12.05 |
| 16.8872 | 5.24598 | 49.59 |
| 17.7791 | 4.98477 | 57.52 |
| 18.2426 | 4.85916 | 20.16 |
| 18.5466 | 4.7802 | 56.98 |
| 19.0971 | 4.64362 | 28.99 |
| 19.5228 | 4.54331 | 15.32 |
| 20.9586 | 4.23519 | 100 |
| 21.4725 | 4.13499 | 15.31 |
| 21.9023 | 4.0548 | 51.87 |
| 22.5885 | 3.93316 | 15.63 |
| 23.2747 | 3.81872 | 35.35 |
| 23.7843 | 3.73804 | 33.87 |
| 24.2659 | 3.66493 | 19.29 |
| 24.5021 | 3.63014 | 52.36 |
| 25.7954 | 3.45099 | 37.51 |
| 27.2366 | 3.27157 | 14.86 |
| 28.8434 | 3.09287 | 9.74 |
| 29.8817 | 2.98772 | 16.53 |
| 31.6801 | 2.8221 | 12.73 |
| 31.9161 | 2.80177 | 9.19 |

TABLE 4-continued

XRD data of Example 21 (Form A)

| Pos. [°2θ] | d-spacing [Å] | relative intensity [%] |
|---|---|---|
| 36.6275 | 2.45146 | 9.52 |
| 37.0775 | 2.42274 | 10.56 |

Example 24: Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound ($EC_{50}$). TLR7 activity for compounds of the present disclosure was assessed using the human TLR7 assay and the results are shown in Table 5 below wherein the degree of TLR7 activation for each compound is expressed as a $pEC_{50}$ value.

TABLE 5

| Compound of Ex. No. | TLR7 ($pEC_{50}$) |
|---|---|
| 1 | 6.8 |
| 2 | 6.1 |
| 3 | 7.1 |
| 4 | 7.0 |
| 5 | 7.3 |
| 6 | 6.6 |
| 7 | 6.6 |
| 8 | 6.9 |
| 9 | 6.7 |
| 10 | 6.6 |
| 11 | 6.7 |
| 12 | 7.0 |
| 13 | 6.7 |
| 14 | 5.7 |

Example 25: Human TLR8 Assay

TLR8/NF-kB/SEAPorter™ HEK 293 Cell Line (Imgenex Corporation) is a stably co-transfected cell line which expresses full-length human TLR8 and the secreted alkaline phosphatase (SEAP) reporter gene under the transcriptional control of an NF-κB response element. TLR8 expression in this cell line has been tested by flow cytometry. Transfectants with stable expression were selected using the antibiotic blasticidin and geneticin. TLR signaling leads to the translocation of NF-κB and activation of the promoter results in expression of the SEAP gene. TLR8-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound ($EC_{50}$). TLR8 activity for compounds of the present disclosure was assessed using the human TLR8 assay and the results are shown in Table 6 below wherein the degree of TLR8 activation for each compound is expressed as a $pEC_{50}$ value.

TABLE 6

| Compound of Ex. No. | TLR8 $pEC_{50}$ |
|---|---|
| 1 | <5 |
| 2 | <5 |
| 3 | <5 |
| 4 | <5 |
| 5 | <5 |
| 6 | <5 |
| 7 | <5 |
| 8 | <5 |
| 9 | <5 |
| 10 | <5 |
| 11 | <5 |
| 12 | <5 |
| 13 | <5 |
| 14 | <5 |

Example 26: hERG Analysis—Method 1

Cell Culture

The hERG-expressing Chinese hamster ovary K1 (CHO) cells described by (Persson, Carlsson, Duker, & Jacobson, 2005) were grown to semi-confluence at 37° C. in a humidified environment (5% $CO_2$) in F-12 Ham medium containing L-glutamine, 10% foetal calf serum (FCS) and 0.6 mg/mL hygromycin (all available from Sigma-Aldrich). Prior to use, the monolayer was washed using a pre-warmed (37° C.) 3 mL aliquot of Versene 1:5,000 (Invitrogen). After aspiration of this solution the flask was incubated at 37° C. in an incubator with a further 2 mL of Versene 1:5,000 for a period of 6 minutes. Cells were then detached from the bottom of the flask by gentle tapping and 10 mL of Dulbecco's Phosphate-Buffered Saline containing calcium (0.9 mM) and magnesium (0.5 mM) (PBS; Invitrogen) was then added to the flask and aspirated into a 15 mL centrifuge tube prior to centrifugation (50 g, for 4 mins). The resulting supernatant was discarded and the pellet gently re-suspended in 3 mL of PBS. A 0.5 mL aliquot of cell suspension was removed and the number of viable cells (based on trypan blue exclusion) was determined in an automated reader (Cedex; Innovatis) so that the cell re-suspension volume can be adjusted with PBS to give the desired final cell concentration. It is the cell concentration at this point in the assay that is quoted when referring to this parameter. CHO-Kv1.5 cells, which were used to adjust the voltage offset on IONWORKS™ HT, were maintained and prepared for use in the same way.

Electrophysiology

The principles and operation of this device have been described by (Schroeder, Neagle, Trezise, & Worley, 2003). Briefly, the technology is based on a 384-well plate (PATCHPLATE™) in which a recording was attempted in each well by using suction to position and hold a cell on a small hole separating two isolated fluid chambers. Once sealing had taken place, the solution on the underside of the PATCHPLATE™ was changed to one containing amphotericin B. This permeablises the patch of cell membrane covering the hole in each well and, in effect, allowed a perforated, whole-cell patch clamp recording to be made.

A β-test IONWORKS™ HT from Essen Instrument was used. There is no capability to warm solutions in this device hence it is operated at r.t. (21° C.), as follows. The reservoir in the "Buffer" position was loaded with 4 mL of PBS and that in the "Cells" position with the CHO-hERG cell suspension described above. A 96-well plate (V-bottom, Greiner Bio-one) containing the compounds to be tested (at 3-fold above their final test concentration) was placed in the "Plate 1" position and a PATCHPLATE™ was clamped into the PATCHPLATE™ station. Each compound plate was laid-out in 12 columns to enable ten, 8-point concentration-effect curves to be constructed; the remaining two columns on the plate were taken up with vehicle (final concentration 0.33% DMSO), to define the assay baseline, and a supra-maximal blocking concentration of cisapride (final concentration 10 μM) to define the 100% inhibition level. The fluidics-head (F-Head) of IONWORKS™ HT then added 3.5 μL of PBS to each well of the PATCHPLATE™ and its underside was perfused with "internal" solution that had the following composition (in mM): K-Gluconate (100 parts), KCl (40 parts), $MgCl_2$ (3.2 parts), EGTA (3 parts) and HEPES (5 parts), pH 7.25-7.30 using 10M KOH). After priming and de-bubbling, the electronics-head (E-head) then moved around the PATCHPLATE™ performing a hole test (i.e. applying a voltage pulse to determine whether the hole in each well is open). The F-head then dispensed 3.5 μL of the cell suspension described above into each well of the PATCHPLATE™ and the cells were given 200 seconds to reach and seal to the hole in each well. Following this, the E-head moved around the PATCHPLATE™ to determine the seal resistance obtained in each well. Next, the solution on the underside of the PATCHPLATE™ was changed to "access" solution that has the following composition (in mM): KCl (140 parts), EGTA (1 part), $MgCl_2$ (1 part), and HEPES (20 parts, pH 7.25-7.30 using 10M KOH) plus 100 μg/mL of amphotericin B (Sigma-Aldrich). After allowing 9 minutes for patch perforation to take place, the E-head moved around the PATCHPLATE™ 48 wells at a time to obtain pre-compound hERG current measurements. The F-head then added 3.5 μL of solution from each well of the compound plate to 4 wells on the PATCHPLATE™ (the final DMSO concentration is 0.33% in every well). This was achieved by moving from the most dilute to the most concentrated well of the compound plate to minimise the impact of any compound carry-over. After approximately 3.5 mins incubation, the E-head then moved around all 384-wells of the PATCHPLATE™ to obtain post-compound hERG current measurements. In this way, non-cumulative concentration-effect curves can be produced where, providing the acceptance criteria are achieved in a sufficient percentage of wells (see below), the effect of each concentration of test compound was based on recording from between 1 and 4 cells.

The pre- and post-compound hERG current was evoked by a single voltage pulse consisting of a 20 second period holding at −70 mV, a 160 millisecond step to −60 mV (to obtain an estimate of leak), a 100 millisecond step back to −70 mV, a 1 second step to +40 mV, a 2 second step to −30 mV and finally a 500 millisecond step to −70 mV. In between the pre- and post-compound voltage pulses there was no clamping of the membrane potential. Currents were leak-subtracted based on the estimate of current evoked during the +10 mV step at the start of the voltage pulse protocol. Any voltage offsets in IONWORKS™ HT were adjusted in one of two ways. When determining compound potency, a depolarising voltage ramp was applied to CHO-Kv1.5 cells and the voltage noted at which there was an inflection point in the current trace (i.e. the point at which channel activation is seen with a ramp protocol). The voltage at which this occurred has previously been determined using the same voltage command in conventional electrophysiology and found to be −15 mV (data not shown); thus an offset potential could be entered into the IONWORKS™ HT software using this value as a reference point. When determining the basic electrophysiological properties of hERG, any offset was adjusted by determining the hERG tail current reversal potential in IonWorks™ HT, comparing it with that found in conventional electrophysiology (−82 mV) and then making the necessary offset adjustment in the IONWORKS™ HT software. The current signal is sampled at 2.5 kHz.

Pre- and post-scan hERG current magnitude was measured automatically from the leak subtracted traces by the IonWorks' HT software by taking a 40 ms average of the current during the initial holding period at −70 mV (baseline current) and subtracting this from the peak of the tail current response. The acceptance criteria for the currents evoked in each well are: pre-scan seal resistance >60MΩ, pre-scan hERG tail current amplitude >150 pA; post-scan seal resistance >60MΩ. The degree of inhibition of the hERG current can be assessed by dividing the post-scan hERG current by the respective pre-scan hERG current for each well. References: Persson, F. et al, J Cardiovasc. Electrophysiol., 16, 329-341 (2005), and Schroeder, K., et al, J Biomol Screen., 8, 50-64, (2003).

Example 27: hERG Analysis—Method 2

The hERG potassium current was measured in a hERG-stably-expressing Chinese hamster ovary K1 (CHO) cells. The experiments were performed using an automated planar patch-clamp system QPATCH HT (Sophion Bioscience A/S). The application of pressure for forming gigaseals and whole-cell patch clamp configuration were established using the QPATCH assay software. Patch-clamp experiments were performed in voltage-clamp mode and whole-cell currents were recorded from individual cells. The following stimulation protocol was applied to investigate the effects of compounds on hERG potassium channel. The membrane potential was held at −80 mV and repetitively (every 15 s) depolarized to +20 mV for 5 s after the pulse to −50 mV for 20 ms served to define the baseline, followed by repolarizing step to −50 mV for 5 s to evaluate of the tail current amplitude. Experiments were conducted at room temperature (22±2° C.).

Effects of compounds were determined from cumulative applications of increasing 4 concentrations and calculated as percent of blocked current. The data points were fitted with Hill equation to calculate half-maximal inhibition concentrations. The test solution includes:

Extracellular solution (mM): 2 mM of $CaCl_2$, 1 mM of $MgCl_2$, 10 mM of HEPES, 4 mM of KCl, 145 mM of NaCl, and 10 mM of Glucose; and Intracellular solution (mM): 5.4 mM of $CaCl_2$, 1.8 mM of $MgCl_2$, 10 mM of HEPES, 31 mM of KOH, 10 mM of EGTA, 120 mM of KCl, and 4 mM of ATP.

The results of the hERG analysis are shown in Table 7:

TABLE 7

| Ex. No. | hERG (Method 1) μM | hERG (Method 2) μM |
| --- | --- | --- |
| 1 | >33 | >10 |
| 2 |  | >10 |
| 3 | >33 | >10 |
| 4 |  | >10 |
| 5 | >33 | >10 |
| 6 | >33 | >10 |
| 7 |  | >10 |
| 8 |  | >10 |
| 9 |  | >10 |

Example 28: Tumour Growth Studies in Renca, a Murine Syngeneic Renal Carcinoma Tumour Model Experiments were conducted on female mice (Balb/C genotype, at least 5 weeks old). Renca mouse tumour cells (Cancer Chemother Pharmacol. 1995; 36 (1): 7-12) were kindly provided by Dr. T. Fujioka at Department of Urology, Iwate Medical University School of Medicine. Renca mouse tumour cells (5×104) were implanted subcutaneously in the flank of mice on day 0. Mice were treated with either drug vehicle (0.5% methylcellulose), the compound of Example 3 (0.3 mg/kg once a week) or the compound of Example 4 (3 mg/kg once a week) administered orally (p. o.) on days 1, 8, and 15. Tumour volumes were assessed at least twice weekly by bilateral vernier caliper measurements.

Figure 9:
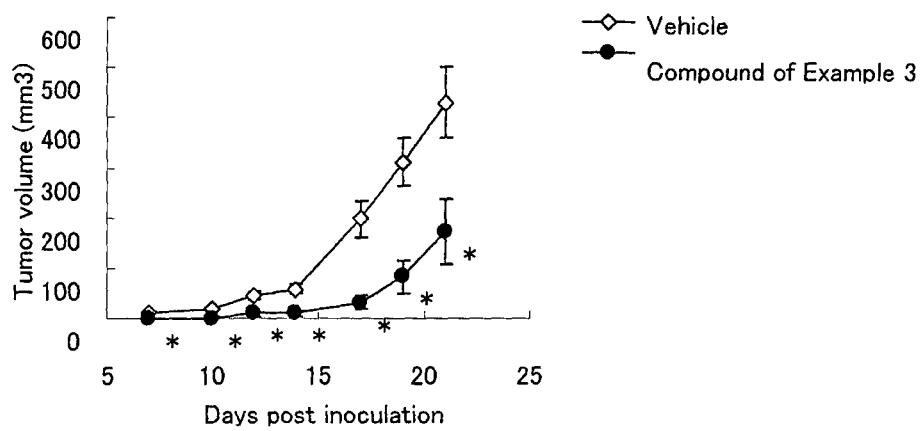
FIG. 9 shows the result of tumour growth inhibition activity to murine syngeneic renal carcinoma: Renca for the compound of Example 3 (mean and SD). X-axis: days post inoculation, Y-axis: Tumour volume, open diamond: 0.5% methylcellulose treated group, closed circle: compound of Example 3 treated group, *: p<0.05 vs. vehicle.

Tumour growth inhibition from the start of treatment was assessed by comparison of the differences in tumour growth rate between control and the compound of Example 3 treated groups, as shown in FIG. 9.

Figure 10:
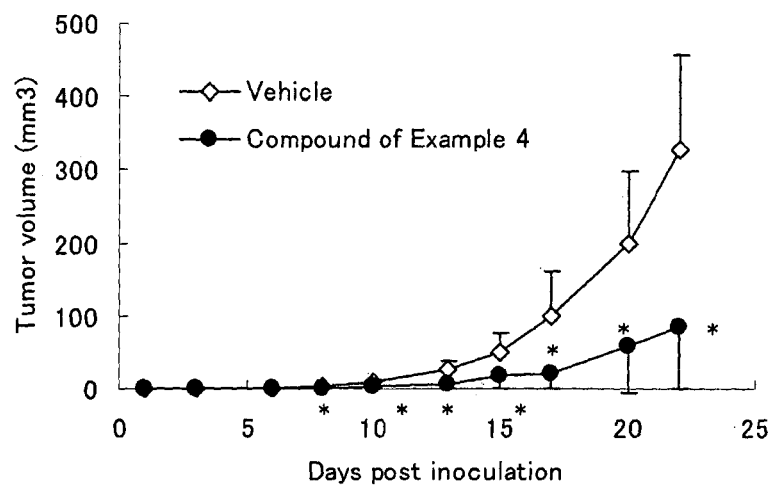
FIG. 10 shows the result of tumour growth inhibition activity to murine syngeneic renal carcinoma: Renca for the compound of Example 4 (mean and SD). X-axis: days post inoculation, Y-axis: Tumour volume, open diamond: 0.5% methylcellulose treated group, closed circle: compound of Example 4 treated group, *: p<0.05 vs. vehicle.

Tumour growth inhibition from the start of treatment was assessed by comparison of the differences in tumour growth rate between control and the compound of the Example 4 treated groups, as shown in FIG. 10.

FIG. 9 and FIG. 10 show that compound of Example 3 and 4 inhibited tumour growth via oral administration.

Example 29: Metastasis Studies in LM8, a Murine Osteosarcoma Tumour Model

Experiments were conducted on female mice (C3H genotype, at least 5 weeks old). LM8 mouse tumour cells (RCB1450) were purchased from RIKEN. LM8 mouse tumour cells ($3\times10^6$) were implanted subcutaneously in the flank of mice on day 0. Mice in radiotherapy alone (RT) group and combination group were anesthetized and received radiation therapy (2Gy) at days 11, 12, 13, 14, and 15. Mice in combination group were also treated with either drug: a compound of Example 3 (10 mg/kg once a week) or a compound of Example 4 (5 mg/kg once a week) administered intravenously (i.v.) on days 11, 18, 25, and 32. Mice were euthanized at day 36, and lungs were isolated. Each lung were weighed, and observed metastasis.

Figure 11:
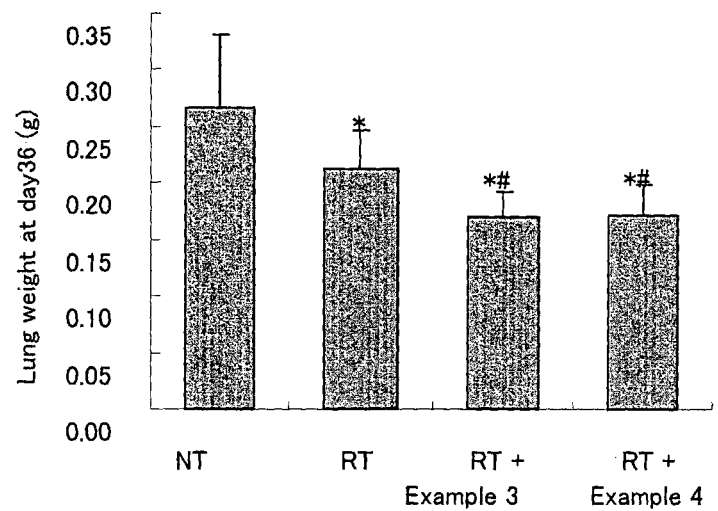
FIG. 11 shows the result of metastasis studies in LM8 tumour growth inhibition activity (mean and SD). X-axis: NT means no treatment and RT means radiation (2Gy×5 consecutive days), Y-axis: lung weight at day 36, *: p<0.05 vs. vehicle, #: p<0.05 vs. RT

Compared to control group, lung metastasis was significantly inhibited in RT treated group and combination group. Compared to RT group, lung metastasis was significantly inhibited in combination group, as shown in FIG. 11.

Example 30: Survival Studies in CT26, a Murine Syngeneic Colon Carcinoma Tumour Model Experiments were conducted on female mice (Balb/C genotype, at least 5 weeks old). CT26 mouse tumour cells (CRL-2638) were purchased from ATCC. CT26 mouse tumour cells ($1\times10^6$) were implanted subcutaneously in the flank of mice on day 0. Mice in radiotherapy alone (RT) group and combination group were anesthetized and received radiation therapy (2Gy) at days 7, 8, 9, 10, and 11. Mice in combination group were also treated with a compound of Example 3 (30 mg/kg once a week) administered orally (p.o.) or Example 4 (5 mg/kg once a week) administered intravenously (i. v.) on days 7, 14, 22, and 27. Tumour volumes were assessed at least twice weekly by bilateral vernier caliper measurements. Survival period was determined by the time taken for tumours to reach 4 times the volume at the time of treatment.

Figure 12:
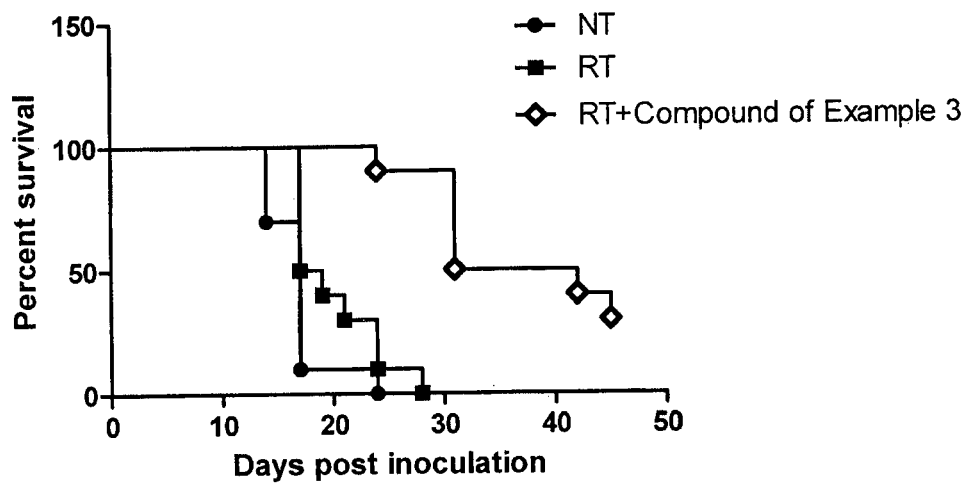
FIG. 12 shows the result of survival studies in CT26. NT means no treatment and RT means radiation (2Gy×5 consecutive days). Closed circle: NT, closed square: RT, closed triangle: combination of RT and compound of Example 3.
Figure 13:
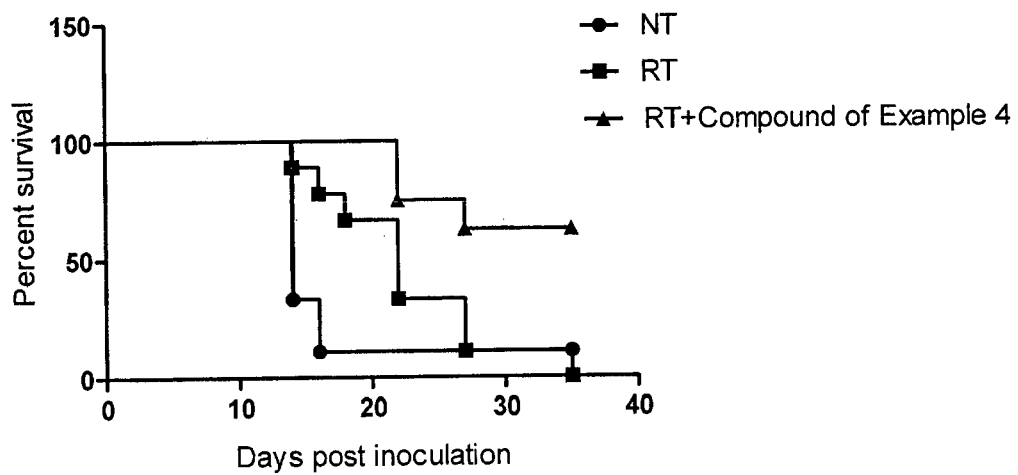
FIG. 13 shows the result of survival studies in CT26. NT means no treatment and RT means radiation (2Gy×5 consecutive days). Closed circle: NT, closed square: RT, closed triangle: combination of RT and compound of Example 4.

Mice in combination treat group survived significantly longer than control or RT treatment group, FIGS. 12 and 13.

The invention claimed is:
1. A method of treating cancer in a subject in need thereof comprising:
administering to said subject a therapeutically effective amount of at least one compound selected from a group consisting of:
2-((4-((2-amino-4-(1-hydroxyhexan-3-ylamino)-6-methylpyrimidin-5-yl)methyl)-3-methoxybenzyl)(2,2-difluoroethyl)amino)acetic acid,
2-((4-((2-amino-4-(1-hydroxyhexan-3-ylamino)-6-methylpyrimidin-5-yl)methyl)-3-methoxybenzyl)(2,2,2-triflooroethyl)amino)acetic acid,
(S)-2-((4-((2-amino-4-(1-hydroxyhexan-3-ylamino)-6-methylpyrimidin-5-yl)methyl)-3-methoxybenzyl)(2,2-diflooroethyl)amio)acetic acid, and
(S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, and
pharmaceutically acceptable salts of any on the foregoing,
wherein the cancer is chosen from bladder cancer, head and neck cancer, prostate cancer, breast cancer, lung cancer, renal carcinoma, ovarian cancer, colon carcinoma, skin cancer, osteosarcoma, and a lymphoproliferative tumor.
2. The method according to claim 1, wherein the at least one compound is selected from the group consisting of:
(S)-2-((4-((2-amino-4-(1-hydroxyhexan-3-ylamino)-6-methylpyrimidin-5-yl)methyl)-3-methoxybenzyl)(2,2-diflooroethyl)amio)acetic acid,
(S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, and
pharmaceutically acceptable salts of any of the foregoing.
3. The method according to claim 1, wherein the at least one compound is selected from the group consisting of:
(S)-2-((4-((2-amino-4-(1-hydroxyhexan-3-ylamino)-6-methylpyrimidin-5-yl)methyl)-3-methoxybenzyl)(2,2-diflooroethyl)amio)acetic acid and pharmaceutically acceptable salts thereof.
4. The method according to claim 1, wherein the at least one compound is selected from the group consisting of:
(S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid and pharmaceutically acceptable salts thereof.
5. The method according to claim 1, wherein the cancer is chosen from bladder cancer, head and neck cancer, lung cancer, renal carcinoma, skin cancer, and a lymphoproliferative tumor.
6. The method according to claim 5, wherein the at least one compound is selected from the group consisting of:

(S)-2-((4-((2-amino-4-(1-hydroxyhexan-3-ylamino)-6-methylpyrimidin-5-yl)methyl)-3-methoxybenzyl)(2,2-diflooroethyl)amino)acetic acid, (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, and pharmaceutically acceptable salts of any of the foregoing.

7. The method according to claim 5, wherein the at least one compound is selected from the group consisting of:

(S)-2-((4-((2-amino-4-(1-hydroxyhexan-3-ylamino)-6-methylpyrimidin-5-yl)methyl)-3-methoxybenzyl)(2,2-diflooroethyl)amio)acetic acid and pharmaceutically acceptable salts thereof.

8. The method according to claim 5, wherein the at least one compound is selected from the group consisting of:

(S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid and pharmaceutically acceptable salts thereof.

9. A method of treating asthma, COPD, allergic rhinitis, allergic conjunctivitis, atopic dermatitis, hepatitis B, hepatitis C, HIV, HPV, *Mycobacterium avium*, leishmaniasis, or dermatosis in a subject in need thereof comprising:

administering to said subject a therapeutically effective amount of at least one compound selected from:

2-((4-((2-amino-4-(1-hydroxyhexan-3-ylamino)-6-methylpyrimidin-5-yl)methyl)-3-methoxybenzyl)(2,2-difluoroethyl)amino)acetic acid, 2-((4-((2-amino-4-(1-hydroxyhexan-3-ylamino)-6-methylpyrimidin-5-yl)methyl)-3-methoxybenzyl)(2,2,2-triflooroethyl)amino)acetic acid, (S)-2-((4-((2-amino-4-(1-hydroxyhexan-3-ylamino)-6-methylpyrimidin-5-yl)methyl)-3-methoxybenzyl)(2,2-diflooroethyl)amio)acetic acid, (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, and pharmaceutically acceptable salts of any of the foregoing.

10. The method according to claim 9, wherein the at least one compound is selected from (S)-2-((4-((2-amino-4-(1-hydroxyhexan-3-ylamino)-6-methylpyrimidin-5-yl)methyl)-3-methoxybenzyl)(2,2-diflooroethyl)amio)acetic acid, (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid, and pharmaceutically acceptable salts of any of the foregoing.

11. The method according to claim 9, wherein the at least one compound is selected from (S)-2-((4-((2-amino-4-(1-hydroxyhexan-3-ylamino)-6-methylpyrimidin-5-yl)methyl)-3-methoxybenzyl)(2,2-diflooroethyl)amio)acetic acid and pharmaceutically acceptable salts thereof.

12. The method according to claim 9, wherein the at least one compound is selected from (S)-2-((4-((2-amino-4-(1-hydroxyhexan-3-ylamino)-6-methylpyrimidin-5-yl)methyl)-3-methoxybenzyl)(2,2,2-trifluoroethyl)amino)acetic acid and pharmaceutically acceptable salts thereof.

13. The method according to claim 5, wherein the cancer is bladder cancer.

14. The method according to claim 5, wherein the cancer is head and neck cancer.

15. The method according to claim 5, wherein the cancer is lung cancer.

16. The method according to claim 5, wherein the cancer is renal carcinoma.

17. The method according to claim 5, wherein the cancer is skin cancer.

18. The method according to claim 5, wherein the cancer is a lymphoproliferative tumor.

* * * * *

UNITED STATES PATENT AND TRADEMARK OFFICE
CERTIFICATE OF CORRECTION

PATENT NO. : 11,299,465 B2
APPLICATION NO. : 16/736660
DATED : April 12, 2022
INVENTOR(S) : Seiji Hori et al.

Page 1 of 2

It is certified that error appears in the above-identified patent and that said Letters Patent is hereby corrected as shown below:

In the Claims

Claim 1, Column 92, Lines 27-28, "(2,2,2-triflooroethyl)" should read --(2,2,2-trifluoroethyl)--.

Claim 1, Column 92, Line 31, "diflooroethyl)amio)acetic acid" should read --difluoroethyl)amino)acetic acid--.

Claim 1, Column 92, Line 35, "any on the foregoing" should read --any of the foregoing--.

Claim 2, Column 92, Line 45, "diflooroethyl)amio)acetic acid" should read --difluoroethyl)amino)acetic acid--.

Claim 3, Column 92, Line 54, "diflooroethyl)amio)acetic acid" should read --difluoroethyl)amino)acetic acid--.

Claim 6, Column 93, Line 3, "diflooroethyl)amio)acetic acid" should read --difluoroethyl)amino)acetic acid--.

Claim 7, Column 93, Line 12, "diflooroethyl)amio)acetic acid" should read --difluoroethyl)amino)acetic acid--.

Claim 9, Column 93, Lines 29-30, "(2,2,2-triflooroethyl)" should read --(2,2,2-trifluoroethyl)--.

Claim 9, Column 93, Line 33, "diflooroethyl)amio)acetic acid" should read --difluoroethyl)amino)acetic acid--.

Claim 10, Column 94, Line 5, "diflooroethyl)amio)acetic acid" should read --difluoroethyl)amino)acetic acid--.

Signed and Sealed this
Twenty-eighth Day of June, 2022

Katherine Kelly Vidal
*Director of the United States Patent and Trademark Office*

Claim 11, Column 94, Line 15, diflooroethyl)amio)acetic acid" should read --difluoroethyl)amino)acetic acid--.